United States Patent
Maher et al.

(10) Patent No.: US 12,024,707 B2
(45) Date of Patent: Jul. 2, 2024

(54) METHODS AND COMPOSITIONS FOR MODULATING LNCRNAS AND METHODS OF TREATMENT BASED ON LNCRNA EXPRESSION

(71) Applicants: Christopher Maher, St. Louis, MO (US); Jessica Silva-Fisher, St. Louis, MO (US); Ryan Fields, St. Louis, MO (US)

(72) Inventors: Christopher Maher, St. Louis, MO (US); Jessica Silva-Fisher, St. Louis, MO (US); Ryan Fields, St. Louis, MO (US)

(73) Assignee: Washington University, St. Louis, MO (US)

( * ) Notice: Subject to any disclaimer, the term of this patent is extended or adjusted under 35 U.S.C. 154(b) by 348 days.

(21) Appl. No.: 17/158,845

(22) Filed: Jan. 26, 2021

(65) Prior Publication Data

US 2021/0277395 A1 Sep. 9, 2021

Related U.S. Application Data

(60) Provisional application No. 62/965,984, filed on Jan. 26, 2020.

(51) Int. Cl.
*C07H 21/04* (2006.01)
*A61K 45/06* (2006.01)
*C12N 15/10* (2006.01)
*C12N 15/113* (2010.01)
*C12Q 1/6886* (2018.01)

(52) U.S. Cl.
CPC ............ *C12N 15/113* (2013.01); *A61K 45/06* (2013.01); *C12N 15/102* (2013.01); *C12Q 1/6886* (2013.01); *C12N 2310/11* (2013.01); *C12N 2320/30* (2013.01); *C12Q 2600/106* (2013.01); *C12Q 2600/178* (2013.01)

(58) Field of Classification Search
CPC ........................... C12N 15/113; C12N 2310/11
See application file for complete search history.

(56) References Cited

PUBLICATIONS

Alekseyenko, A.A. et al. (2014) Reciprocal interactions of human C10orf12 and C17orf96 with PRC2 revealed by BioTAP-XL cross-linking and affinity purification. Proc Natl Acad Sci U S A, vol. 111, No. 7, pp. 2488-2493.
Andrea, C. et al. (2014) Which strategy after first-line therapy in advanced colorectal cancer? World J Gastroenterol., vol. 20, No. 27, pp. 8921-8927.
Arriaga-Canon, C. et al. (2018) The use of long non-coding RNAs as prognostic biomarkers and therapeutic targets in prostate cancer. Oncotarget, vol. 9, No. 29, pp. 20872-20890.
Bailly, C. (2012) Contemporary challenges in the design of topoisomerase II inhibitors for cancer chemotherapy. Chem Rev., vol. 112, No. 7., pp. 3611-3640.
Bernstein, E. et al. (2006) Mouse polycomb proteins bind differentially to methylated histone H3 and RNA and are enriched in facultative heterochromatin. Mol Cell Biol., vol. 26, No. 7, pp. 2560-2569.
Bertino, J.R. (1997) Chemotherapy of colorectal cancer: history and new themes. Semin Oncol, vol. 24, No. 5, Suppl 18, pp. S18-3-S18-7.
Cabanski, C.R. et al. (2015) Pan-cancer transcriptome analysis reveals long noncoding RNAs with conserved function. RNA Biol, vol. 12, No. 6, pp. 628-642.
Cabili, M.N. et al. (2011) Integrative annotation of human large intergenic noncoding RNAs reveals global properties and specific subclasses. Genes Dev., vol. 25, No. 18, pp. 1915-1927.
Cancer Genome Atlas Research Network et al. (2013) The Cancer Genome Atlas Pan-Cancer analysis project. Nature Genetics, vol. 45, pp. 1113-1120.
Chen, S.W. et al. (2017) Overexpression of long non-637 coding RNA H19 is associated with unfavorable prognosis in patients with colorectal cancer and increased proliferation and migration in colon cancer cells. Oncol Lett., vol. 14, No. 2, pp. 2446-2452.
Chen, X. et al. (2016) Integrated analysis of long non-coding RNAs in human colorectal cancer. Oncotarget, vol. 7, No. 17, pp. 23897-23908.
Cortes, F. & Pastor, N. (2001) DNA topoisomerases in cancer chemotherapy: basic and applied aspects. Cytobios, vol. 106, Suppl 2, pp. 217-227.
Diaz-Rubio, E. (2004) New chemotherapeutic advances in pancreatic, colorectal, and gastric cancers. The oncologist, vol. 9, No. 3, pp. 282-294.
El-Deiry, W.S. et al. (2015) Molecular profiling of 6,892 colorectal cancer samples suggests different possible treatment options specific to metastatic sites. Cancer Biol Ther., vol. 16, No. 12, pp. 1726-1737.
Exiqon (2016) In vivo Guidelines. accessed from https://web.archive.org/web/20171011212632/https://www.exiqon.com/ls/Documents/Scientific/ExiqonInVivoGuidelines.pdf on Oct. 21, 2021.
Fellner, C. (2017) Promising Drugs in Clinical Development To Treat Advanced Colorectal Cancer. P T, vol. 42, No. 4, pp. 262-265.
Fernandes, G.D.S. et al. (2018) Combination of Irinotecan, Oxaliplatin and 5-Fluorouracil as a Rechallenge Regimen for Heavily Pretreated Metastatic Colorectal Cancer Patients. J Gastrointest Cancer, vol. 49, No. 4, pp. 470-475.
Foubert, F., Matysiak-Budnik, T. & Touchefeu, Y. (2014) Options for metastatic colorectal cancer beyond the second line of treatment. Dig Liver Dis., vol. 46, No. 2, pp. 105-112.

(Continued)

*Primary Examiner* — Amy Rose Hudson

(57) ABSTRACT

Among the various aspects of the present disclosure is the provision of a methods and compositions for modulating lncRNAs and methods of treatment based on lncRNA expression.

13 Claims, 29 Drawing Sheets

Specification includes a Sequence Listing.

(56) References Cited

PUBLICATIONS

Fountzilas, G. et al. (2012) Topoisomerase II alpha gene amplification is a favorable prognostic factor in patients with HER2-positive metastatic breast cancer treated with trastuzumab. Journal of translational medicine, vol. 10, No. 212, 13 pages.

Garajova, I. et al. (2017) Non-Coding RNAs as Predictive Biomarkers to Current Treatment in Metastatic Colorectal Cancer. Int J Mol Sci., vol. 18, No. 7, 1547, 10 pages.

Gil, J. & O'Loghlen, A. (2014) PRC1 complex diversity: where is it taking US? Trends Cell Biol., vol. 24, No. 11, pp. 632-641.

Gooding, A.J. et al. (2017) The lncRNA BORG Drives Breast Cancer Metastasis and Disease Recurrence. Scientific reports, vol. 7, 12698, 18 pages.

Groot Koerkamp, B. et al. (2017) Perioperative Hepatic Arterial Infusion Pump Chemotherapy Is Associated With Longer Survival After Resection of Colorectal Liver Metastases: A Propensity Score Analysis. J Clin Oncol., vol. 35, No. 17, pp. 1938-1944.

Grossman, J.G. et al. (2018) Recruitment of CCR2(+) tumor associated macrophage to sites of liver metastasis confers a poor prognosis in human colorectal cancer. Oncoimmunology, vol. 7, No. 9, e1470729, 11 pages.

Grothey, A. & Clark, J. (2016) Colorectal Cancer Treatment; Metastatic Cancer (Beyond the Basics). Obtained from https://web.archive.org/web/20160317003117/https://www.uptodate.com/contents/colorectal-cancer-treatment-metastatic-cancer-beyond-the-basics on Oct. 21, 2021. 9 pages.

Harrow, J. et al. (2012) Gencode: the reference human genome annotation for The Encode Project. Genome Res., vol. 22, No. 9, pp. 1760-1774.

Hon, K.W. et al. (2018) miRNAs and lncRNAs as Predictive Biomarkers of Response to Folfox Therapy in Colorectal Cancer. Front Pharmacol., vol. 9, 846, 10 pages.

Hur, K. (2015) MicroRNAs: promising biomarkers for diagnosis and therapeutic targets in human colorectal cancer metastasis. BMB Rep., vol. 48, No. 4, pp. 217-222.

Jimenez-Fonseca, P. et al. (2015) Gemcitabine plus capecitabine (Gem-Cape) biweekly in chemorefractory metastatic colorectal cancer. Clin Transl Oncol., vol. 17, No. 5, pp. 384-392.

Kavuri, S.M. et al. (2011) Cellular FLICE-inhibitory protein (cFLIP) isoforms block CD95- and TRAIL death receptor-induced gene induction irrespective of processing of caspase-8 or cFLIP in the death-inducing signaling complex. J Biol Chem, vol. 286, No. 19, pp. 16631-16646.

Khayat, D. et al. (2001) The role of irinotecan and oxaliplatin in the treatment of advanced colorectal cancer. Oncology, vol. 15, No. 4, 4 pages.

Kim, S.K. et al. (2014) A nineteen gene-based risk score classifier predicts prognosis of colorectal cancer patients. Mol. Oncol., vol. 8, No. 8, pp. 1653-1666.

Kim, T. et al. (2015) Role of MYC-regulated long noncoding RNAs in cell cycle regulation and tumorigenesis. J Natl Cancer Inst., vol. 107, No. 4, dju505, 11 pages.

Kuppusamy, P. et al. (2017) Proteins are potent biomarkers to detect colon cancer progression. Saudi J Biol Sci., vol. 24, No. 6, pp. 1212-1221.

Lee, B. et al. (2014) Long Noncoding RNAs as Putative Biomarkers for Prostate Cancer Detection, J Mol Diagn., vol. 16, No. 6, pp. 615-626.

Lee, J.J. & Sun, W. (2016) Options for Second-Line Treatment in Metastatic Colorectal Cancer. Clin Adv Hematol Oncol., vol. 14, No. 1, pp. 46-54.

Li, X. et al. (2014) TOP2Ahigh is the phenotype of recurrence and metastasis whereas TOP2Aneg cells represent cancer stem cells in prostate cancer. *Oncotarget*, vol. 5, No. 19, pp. 9498-9513.

Li, H. et al. (2017) Roles of long noncoding RNAs in colorectal cancer metastasis. Oncotarget, vol. 8, No. 24, pp. 39859-39876.

Liao, Y., Smyth, G.K. & Shi, W. (2014) featureCounts: an efficient general purpose program for assigning sequence reads to genomic features. Bioinformatics, vol. 30, No. 7, pp. 923-930.

Ling, H. et al. (2013) CCAT2, a novel noncoding RNA mapping to 8q24, underlies metastatic progression and chromosomal instability in colon cancer. Genome Res, vol. 23, No. 9, pp. 1446-1461.

Ling, H., Fabbri, M. & Calin, G.A. (2013) MicroRNAs and other non-coding RNAs as targets for anticancer drug development. Nat Rev Drug Discov, vol. 12, No. 11, pp. 847-865.

Litvak, D.A. et al. (2002) Systemic irinotecan and regional floxuridine after hepatic cytoreduction in 185 patients with unresectable colorectal cancer metastases. Ann Surg Oncol., vol. 9, No. 2, pp. 148-155.

Liu, Y. et al. (2015) Over-expression of lncRNA DANCR is associated with advanced tumor progression and poor prognosis in patients with colorectal cancer. Int J Clin Exp Pathol, vol. 8, No. 9, pp. 11480-11484.

Liu, L. et al. (2016) Relevance between TOP2A, EGFR gene 719 expression and efficacy of docetaxel plus epirubicin as neoadjuvant chemotherapy in triple negative breast cancer patients. Zhonghua yi xue za zhi, vol. 96, No. 12, pp. 940-943.

Ma, L. (2016) MicroRNA and Metastasis, Advances in Cancer Research, vol. 132, pp. 165-207.

Matouk, I.J. et al. (2009) Highly upregulated in liver cancer noncoding RNA is overexpressed in hepatic colorectal metastasis. Eur J Gastroenterol Hepatol, vol. 21, No. 6, pp. 688-692.

Miura, J.T. et al. (2015) Tumor profiling of gastric and esophageal carcinoma reveal different treatment options. Cancer Biol Ther., vol. 16, No. 5, pp. 764-769.

Moranova, L. & Bartosik M. (2019) Long Non-Coding RNAs—Current Methods of Detection and Clinical Applications, Klin Onkol., vol. 32, Supplementum 3, pp. 65-71.

NCBI (2019). Blast Results. Obtained from https://blast.ncbi.nlm.nih.gov/Blast.cgi#alnHdr_674274967 on Feb. 22, 2019. 9 pages.

Nitiss, J.L. (2002) DNA topoisomerases in cancer chemotherapy: using enzymes to generate selective DNA damage. Current opinion in investigational drugs, vol. 3, No. 10, pp. 1512-1516.

Nygard, S.B. et al. (2013) Underpinning the repurposing of anthracyclines towards colorectal cancer: assessment of topoisomerase II alpha gene copy No. alterations in colorectal cancer. Scand J Gastroenterol., vol. 48, pp. 1436-1443.

Ouyang, S. et al. (2019) LncRNA BCAR4, targeting to miR-665/STAT3 signaling, maintains cancer stem cells stemness and promotes tumorigenicity in colorectal cancer. Cancer cell international, vol. 19, 72, 12 pages.

Paschos, K.A. & Bird, N. (2008) Current diagnostic and therapeutic approaches for colorectal cancer liver metastasis. Hippokratia, vol. 12, No. 3, pp. 132-138.

Pei, Y.F., Yin, X.M. & Liu, X.Q. (2012) TOP2A induces malignant character of pancreatic cancer through activating beta-catenin signaling pathway. Biochimica et biophysica acta, vol. 1864, No. 1, pp. 197-207.

Pommier, Y. (2013) Drugging topoisomerases: lessons and challenges. ACS Chem Biol., vol. 8, No. 1, pp. 82-95.

Power, D.G. & Kemeny, N.E. (2009) The role of floxuridine in metastatic liver disease. Mol Cancer Ther., vol. 8, No. 5, pp. 1015-1025.

Rinn, J.L. & Chang, H.Y. (2012) Genome regulation by long noncoding RNAs. Annu Rev Biochem, vol. 81, No. 10, pp. 145-166.

Robinson, M.D., Mccarthy, D.J. & Smyth, G.K. (2010) edgeR: a Bioconductor package for differential expression analysis of digital gene expression data. Bioinformatics, vol. 26, No. 1, pp. 139-140.

Saif, M.W. et al. (2011) The efficacy of gemcitabine as salvage treatment in patients with refractory advanced colorectal cancer (CRC): a single institution experience. Anticancer Res., vol. 31, No. 9, pp. 2971-2974.

Sanchez, Y. & Huarte, M. (2013) Long non-coding RNAs: challenges for diagnosis and therapies. Nucleic Acid Ther., vol. 23, No. 1, pp. 15-20.

Schwarzenbach, H. (2016) Biological and Clinical Relevance of H19 in Colorectal Cancer Patients. EBioMedicine, vol. 13, pp. 9-10.

Shi, D. et al. (2017) Prognostic value of long non-coding RNA CCAT1 expression in patients with cancer: A meta-analysis. PLoS One, vol. 12, e0179346, 20 pages.

(56) References Cited

PUBLICATIONS

Shuai, P. (2016) Expressions of HER2 and Topo IIalpha in breast cancer and its clinical significance. Zhong nan da xue xue bao. Yi xue ban, vol. 41, No. 11, 1143-1147.

Siegel, R., Naishadham, D. & Jemal, A. (2012) Cancer statistics, 2012. CA Cancer J Clin., vol. 62, No. 1, pp. 10-29.

Siegel, R.L. et al. (2017) Colorectal cancer statistics, 2017. CA Cancer J Clin., vol. 67, No. 3, pp. 177-193.

Silva, J.M. et al. (2010) Identification of long stress-induced non-coding transcripts that have altered expression in cancer. Genomics, vol. 95, No. 6, pp. 355-362.

Silva, J.M. et al. (2011) LSINCT5 is over expressed in breast and ovarian cancer and affects cellular proliferation. RNA Biol, vol. 8, No. 3, pp. 496-505.

Silva, J. & Smith, D. (2012) Long non-coding RNAs and Cancer, Caister Academic Press, La Jolla, California. pp. 141-154.

Sonderstrup, I.M. et al. (2015) Topoisomerase-1 and -2A gene copy numbers are elevated in mismatch repair-proficient colorectal cancers. Mol. Oncol., vol. 9, No. 6, pp. 1207-1217.

Speir, M.L. et al. (2016) The UCSC Genome Browser database: 2016 update. Nucleic Acids Res, vol. 44, pp. D717-D725.

Stouffer, S.A. (1949) A study of attitudes. Sci Am., vol. 180, No. 5, pp. 11-15.

Sveen, A. et al. (2011) Transcriptome instability in colorectal cancer identified by exon microarray analyses: Associations with splicing factor expression levels and patient survival. Genome Med, vol. 3, No. 5, 32, 13 pages.

Swiderska, M. et al. (2014) The diagnostics of colorectal cancer. Contemp Oncol, vol. 18, No. 1, pp. 1-6.

Tang, X. et al. (2019) Regulation Mechanism of Long Noncoding RNAs in Colon Cancer Development and Progression. Yonsei Med J, vol. 60, No. 4, pp. 319-325.

Tarpgaard, L.S. et al. (2016) A phase II study of Epirubicin in oxaliplatin-resistant patients with metastatic colorectal cancer and TOP2A gene amplification. BMC cancer, vol. 16, 91, 5 pages.

Thorn, C. F. et al. (2011) Doxorubicin pathways: pharmacodynamics and adverse effects. Pharmacogenet Genomics, vol. 21, No. 7, pp. 440-446.

Trapnell, C., Pachter, L. & Salzberg, S.L. (2009) TopHat: discovering splice junctions with RNA-Seq. Bioinformatics, vol. 25, No. 9, pp. 1105-1111.

Trapnell, C. et al. (2010) Transcript assembly and quantification by RNA-Seq reveals unannotated transcripts and isoform switching during cell differentiation. Nat Biotechnol, vol. 28, No. 5, pp. 511-515.

Tsavaris, N. et al. (2009) Topoisomerase I and IIalpha protein expression in primary colorectal cancer and recurrences following 5-fluorouracil-based adjuvant chemotherapy. Cancer Chemother Pharmacol, vol. 64, No. 2, pp. 391-398.

Weidle, U.H. et al. (2017) Long Non-coding RNAs and their Role in Metastasis. Cancer Genomics Proteomics, vol. 14, No. 3, pp. 143-160.

White, N.M. et al. (2014) Transcriptome sequencing reveals altered long intergenic non- coding RNAs in lung cancer. Genome Biol, vol. 15, No. 8, 429, 16 pages.

Yang, L. et al. (2011) ncRNA- and Pc2 methylation-dependent gene relocation between nuclear structures mediates gene activation programs. Cell, vol. 147, No. 4, pp. 773-788.

Yang, Y. et al. (2017) Long non-coding RNAs in Colorectal Cancer: Progression and Future Directions, J Cancer, vol. 8, No. 16, pp. 3212-3225.

Yiu, A.J. & Yiu, C.Y. (2016) Biomarkers in Colorectal Cancer. Anticancer Res., vol. 36, No. 3, pp. 1093-1102.

Zhou, T., Kim, Y., & Macleod, A.R. (2016) Targeting Long Noncoding RNA with Antisense Oligonucleotide Technology as Cancer Therapeutics. Methods Mol Bio, vol. 1402, pp. 199-213.

c d m n

SEQUENCE LISTING

```
<160> NUMBER OF SEQ ID NOS: 42

<210> SEQ ID NO 1
<211> LENGTH: 16130
<212> TYPE: DNA
<213> ORGANISM: homo sapiens

<400> SEQUENCE: 1
```

```
actacctgct tctgctgtgc actcgctctc tccctctttg cttctagcat aacaaatacg      60
ttcccctgca ttgaacgtgt tttcctaaca acagtggcga gatgtgacaa ggaaacttgt     120
ttggagcaac gtctgagtca caatagaatt agtatcaggt acaaatgacc acaaagtaca     180
ggtgctgagt cacagtgatt tgggattctc tagtaaaaag gacatgtgga gaacttaact     240
tttatttcct ctcttttgct ggtgtaagtt tggaggtatc gtcacacaat cacctttcat     300
tcactaacgc tcacatttta ggtgcttttc cttcttacat aataaaatag caaagcacat     360
aggcctgggg tccctgggga aagccaagtc tgcctggctg ccttgagaac tctggactgg     420
atttgacatg gaggagttgg ggattgttgc tcagggatca gaacagtgaa actcaggtta     480
atgagtaaag agtgagaata tgtgtttgta tgtttcttaa tcccatctac taggtgatta     540
caaaactcat tcaaagttga acacagtaga ggtatttcaa gttgctttag agagagaatt     600
acacacacac aaaaaatctt taggagccag acaaccactg tggacaccaa taagagagct     660
ccaacattgg tgaggtatag acccgtcaaa gttgttggta ataacagcaa ggtccatctg     720
gcaagattgg tcacctgtgg tggaagtggt ggtgacagca gggatgcaac tgcagcaatc     780
aatgatgatg atctcactag ggtgggggagg tgttaaaggc atcttcacag cagcacagtg     840
cccagaatgc caaagagcag caggatggat ccagcatcct ctcctgataa agagggcta      900 gaagacggga ggctccggga agtctactgg gtgagtatta gtccactctc acattgctat     960
caagaaatac ctgatactgg gtaatttata gagaaaaaag gtttaattga ctcacggttc    1020
tgcaagctgt ccaggaagca tagcggcttc tgactctggg gtggcctcag gaagcttcca    1080
atcatggaag aaggcaaagt aggggcaggt atctcacatg gcagtagcag gaggaagaga    1140
gcgaggggga ggtgccacac actctttaac taccagatct gacagataac tcattgttcc    1200
aagggcagga caaaggggat gctgctaaac cattcatgag aaatctgccc gcatgatcca    1260
atcacctccc accaggctcc acctccaaca ccggatatta caattcaaca caaaatttgg    1320
acaggaacac agatccaaac tatatcaggg tggagcccta catctaatgt ttcttgccct    1380
tgctcttggt agctagtgtc tcattggact ctagtgtctg cttgttctat tggatcagga    1440
gctccttgag gggaggagcc atattaaatt catctctgta cccctagtgt ttagcagtgt    1500
tttattgagt tagtaaataa atccatctct attctttatc aaaactctga gctgtgatga    1560
aaaagtcact gtctccacct gtgctttgga tctgtcagta gggcctttgc ttctacagta    1620
acatcatcct acacagagta aacacctact gagtgctgat tatgcctgct gtggttacta    1680
caatctctta agtttgcctt taagctttgt atgtaaaatt tttaattgct ttgctatttt    1740
aatctgatca cattccnctg gttcctccct tttaacttta agcatatgca atgtgcccgt    1800
ttgcacaaca gtctgaagtt ttatttctat gattcctcct tttctgcaca aatgttcatg    1860
tttctcatac ttcctattac ttctgaacat tttcctaatg acagaagtca tagaagcact    1920
ccttaaaagt tgattttttg tttgtttgtt tgtttgtttg ttttgagaca ttctgccacc    1980
caggttggag tgcagtggca tgatcatggc tcactgcagc ctcgacctcc tgggctcagg    2040
tgatcctccc accgaagcct cctgagtagc cgggactaca ggcacctgcc accacaccca    2100
gctatttttt gtattttttg tagagatgag gtttcactat gttgccaagg ctggtctaga    2160
gcttctgggc tcaagcaatc tgcccacctc agcctcccaa aatgttagaa ttataagcaa    2220
gagccactgt acccagccga gagctgattt tatattaata tctacagctc tggttagaca    2280
cagtctcagg gaatttgtgg ccagtctgta gtgttgtctc cttacttaaa aaatactcct    2340
```

```
tccttgacct cacttcagtg tctaattata atttcatttt ctacatctat ccatgaaaaa    2400
aatgtataga gtgggggaa atctacctt ccacctccat ttcctcatca tccacttcca     2460
cctgaacttg ctgccacctg acttcagctt caccacctgt gaacacatca ctttctctaa   2520
agcctcccac gctttccttc tgaccttgag ccagtgggct gttttcatac ttctctttca   2580
tagttactta gttgcgttaa cattgtcaaa agtaaaaca aaactcccaa gcctaaagcc    2640
tcccctgctt tgagacagtc tccccatcct gacacctgtg accctgagtt catctgcatt   2700
attccaaccc atctggtgaa tgagttaatg ctgattttg atcatccaac atggtgtcag   2760
cctccttcag ccttccaagg tgagcctatg aatttcctcc cttctaagtc cacatacgtt   2820
tgtttcctcc cactctgcat ctttaccca ttcatggcac tcttaactcc acatagcccc    2880
ttagttttct aaaccattt aaaaccttac accatcaagg agaagcatag cttcttaaac    2940
tttccctact gtaatggctt ctcagggttt gtgtgaacag tggggttttt taattttttg   3000
gtataatact aatttatcaa cacatgtata cttcttggtg aatatgctta aggttatttt   3060
tttcatgagt gtatattgct ccccgagatc ctttcttgca tttgggtttt ttccaaaatg   3120
cttaatatgg tcctccatat gcagaggaca ctagctaaat attggttaaa gtgggtaaca   3180
attaaaaatg taatactcct gccagctgag taaatactta acttgcttaa tatgaccgtg   3240
acaatttgtc cagacactgc catttcctgc tttcagggca ctgttgtctg ttgctaactt   3300
attgctcctc tgggtctcct tttcctacct ggttcagatg tagaatgtgg ggcttacaaa   3360
gttagaggag gacattttct tatgggtttt gttacctata ccagtaagtt agaaggaaaa   3420
actcactaag gaaaaccaa acctaaccat tttttacaca gccaacacag agcatttcac   3480
ctctagtctc caaatatat agggatttct ccccaccagc aaccaataaa ttccctagca    3540
gatatcagct atgtgtacta taatttaatt caattctgac actatctatc tggagatagc   3600
atcagatccc acagaataag ggttctaccc cacaggactg cccccacttc agaggccgat   3660
cacgagttac aggttgtcac ctctgcttct gctgatcagc tataagtcaa gattcccact   3720
actgtctcct tgggttcaat taatttgcta ggatgactta cacaactcag aggaacacct   3780
attttgttt actggtttat tataaaggat actaaaaaag atacagatga acagccagga   3840
ggaagagatg cataggcaag gcatgtggga aggggcatgg agcttccatg ccctctctgc   3900
atgtgccacc ctccaggact ttccacacgt tcagctatcc agaagctcct gaacctggtc   3960
attttgagtt tttatgaagg cttcatcatg taggcatgat tgattaagtc atgagccatt   4020
ggtcagcccc tgtttcttcc ctggaggtga aggttgattg gtgggacttt aagtcccaac   4080
cgtctaatca tgccttggtc tttctggtga ccagccccca tacggaagct acttagggt    4140
ccctaggcat cagtaatctc cacagcatat caaagacact catcactttg agattccca   4200
agggttttag aagctgtatg tcaagaaaca ggagcaagcc caaatacata tttcataata   4260
tcataaccat gtgacaactt atcataaaga ccaggtactc acttaccaga ctgaatgcct   4320
gtaagagttg atgaagttta cttgagcgga gaaggaactg atggaagcct ctcgtgccag   4380
acaggttgaa gttcaggttt gccatactct agtagtatga ttttggcaaa gttacttaac   4440
ttctctgtgc ctcagtttct tgtgccaatg aaaggagatt gagaaagtga atggggcaaa   4500
atactaacat ttgatgaatc tgggtaaagg gtatacaggc ttctatctac tatttttgta   4560
acttttctat aaatttgaaa ttatttcaaa ataaaaagta aaaaaatac tcttgtgact    4620
tggagactca attttccat ttgcaagata gttgagtttt cacatatagt cttaaagaat    4680
gatgctaaca ttttccgagt ggcaaactgg gacattttgt ctgaggaatc tctttaaatt   4740
```

```
ttttaaagat aaaagtctttt caaagattat aagttaaagc acattaataa acagactttt    4800
taaagaagac taaatatat  gacaagaaat aaaaatgtaa taaactacct ttattggtta     4860
ataaaagact tgaattttaa agtcagcagt atattgatcc actagtattg tttgaagaac    4920
tcagtttgct caataacgaa ttttttttccc caaatttcat tgcaaatctt cattgaaatt   4980
gaattatcat tgttgacacc tccaattcat ccaaagttct taacctaaca atattgcttc   5040
tcaatgtgcc cagaagtgaa aagacaaaat catgtgtttt tattaggtat gaaatattca   5100
cattcacaga ataaaatct gtaagtaaat tttatcatct ctaatacaag gagattttat    5160
catctccttt tgtgtgttac actcagctag taagttctct ttaaaataca gttttgtgat   5220
acaaagttaa ttttaaaacc atattaccaa atagcagaga atgtcaaaaa catgataagt   5280 tggcttttcag tttaaaatgg aaatgtactc cattgcaact tttcctaatt ttatacagag  5340
tcatgaagac actgaaaagt gatgaatcca cataaccatg acactggaaa tgaagtttga   5400
gtggcagtca gaatctggga ggaagcattg ctaagtgaaa atcttatgga gcttgactaa   5460
aaatccctgt caggaaccgt caaaagctgt gtccctgaca tgaaaaatct tgctggaagt   5520
tgagagaggt ttatgcctac tccgtgatcc gggaacacaa gacctttacc aaccaaaaaa   5580
gtggatagct gttcttctgc tgtgaaggtt aataaaggta acattataa  tggccagggc    5640 tgggttgag  gcagaaagaa ggaagaagga aagaaagaaa gagacaaagg taataatatt   5700
agtaaaggta aataatgtta gtgtctctca aacaaaaat  aatttgacag aaaaaagaat   5760
cattttatat tgataaaaga tgtaatccat aaaatagatg taaaattcat gagcttctat   5820
agtattacaa tctttaaatg gaaaattgac agaaatataa ttgttataaa agacattaaa   5880
atatttttct caagatttgg gaaagactaa aaagtaaaac aagattgaat gagtaggcag   5940
atcttgaatt ttgtattta  aaagtggaga atataccttt tcatgcaacc atggatcatt   6000
tgcagtagct gatcatacca ctgggacaca gagaaaattt tactatgtaa taaaaatgag   6060
aacatgtaga agccacattc atatgatcaa aactaacata cactaagaaa agtttaaaca   6120
aagtcttcaa tccatgagtt atctaacaat ttctaaaatg aagtcagagt atttgttttt   6180
gaaactttaa agtttatatg taatctataa gacaatattc ataacaacac tttataacaa   6240
caaaatggtg gaaataaccc aaatgtttgt tggtagaaca tacctatcaa tggagaactg   6300
tgcaactata aatgaggagt ctccaaatat gtttctatttt ttatatactc tgcagaatgc  6360
attgttatat gaaaaagca  aaaatggagg taaatataca atgtgctacc atttatccaa   6420
aacaggtaac aagaatatga atatacatat attaaaaatc acaacagtcc aggagtggtg   6480
gcttatgcct gaaatcccag cactttggga gatggaggtg gaggatcatt taagcccagg   6540
agtttgagac taggctaagc aacagagtga gacattgtct ctacaaaaaa aaaaaaaaaa   6600
aaaaagttag ctgggcatgg tggcatgcac ctgtggtcct agctatttgg gaggctgagg   6660
tgggagaatc acttgagccc aggaggtcat ggctgcagtg agctgggatc atgccactac   6720
actccagcct gggtgacaga gcaagaccct gtctcaaaac aacaaaaaca acaaaacaag   6780
ggtataacaa aacaaacaaa actgaacaaa aattaaaaat tgtttaccta tatgggaacg   6840 gagtagaaa  aacatggatt aaaaacaaaa cttcctgatt ataccttgtt ttgtaagttt    6900
gactttggaa tggtgcaaag attttacata attatcaaat caaattaaca aaaaatttct   6960
aaaaactgaa aggaaaataa aaattactgt attgaactag ttgcttaact acacagagag   7020
gaactatatt aagtaactt  aaaaaaacaa cagagattta acatacaaac ctagtgggat   7080
```

```
atacccctaag aataaaaaaa aatgcaaata cactttatgc cactttcaat tatcatgctg    7140
tttataataa tactggcact gctattctga aactatggta tatattacag gatatggcaa    7200
ataagtactt atattgttaa gaactaagtt gtaagtatga gaaaaaaata taaaagcgaa    7260
gaagcgcaaa ccctataatc ctaaacttga attgaaaaca tcagtatgag ctcatgatat    7320
gttttctctt aacaaaacaa aataacaact tatttcctaa ctctgcctgc taaaaaggcc    7380
tagaaacagt gaccagctca gcagcaatga gttcccataa cacccagact gtagtttcta    7440
atacaatttt tcactaaaag gaatccatat tcttggaaag tcagctaatt tgaagactgg    7500
ggagcaaaaa attcaagaag gcctttatct tggttctttt gtgctgttat aacaaagtac    7560
ctgagactgg gcaattttata aaaatcacaa ctttatttct cacaattctg gaggctaaaa    7620
gttcaagaat aaggcaccag caagttcagt gtctagaaag gacccagcgt ttgcttcgaa    7680
gatggcgcct ttctgctgca ttctctgaag aggatggatg ctgtgtcctc acattgcaga    7740
agtcagaagg ggaaaaaggg cctaagctag ttccctgtag cctttttgca aggtactaat    7800
ccatgtctcg tggctgaatc acttccccaa aagtcttaac tcccaacatc accacaatag    7860
agattaaatt tcaacacatg aattttgtga gaacacattg aaaccacagc agtcttggaa    7920
cacattgtca caccacaaag caagaacatt tcattgacca ctaaagtcgt gtcagaaagg    7980
actcagaatc caatttgaat atctggccaa acttcagtgg ccaaaaaaga gacaatttga    8040
atcagggatt gagacatggc agctttgttt aaatccatgc attcataaaa gaactcttgg    8100
tcacctatag agggttctgg gaaatgagct cattattttg agaactggta aatacaagga    8160
aaggatcaaa tgtgaatcct acctttcctg tactaactgt accacagagt aaccaaatag    8220
ttgacaaagg aagtttctct attatgaagt attcttgcta atacatgatt aaggaatgag    8280
aattcgagta tttgcacatt cgaatgaaat agtggattta ggctaaatgt ctaacatcac    8340
actaagagaa acaactgggc gcctgctaac aaaagtcctg tcactatcac caatggtgtc    8400
ttcttgcaaa aaattccaat tataagtgat caaattaccct attagggagt gagggcacag    8460
gtaatgcaga agacagcaaa catatgaaca atagacacca catggatgca attagcaaaa    8520
tccacaattc tggaaattct gcagggcaaa ctgacctagt ttcttcacca tatacatggc    8580
aaggagggac taggggagg aagtggcaga tgctcttggt gcccacccat atcctctgtg    8640 ccettcactg tgctcagcct tgctcccaac tgtcagtagc tgccttttgg tgcctaagag    8700
cttttttttt ttttctcct gaactgcaga acgccagaag tgccaagcaa ttaacaaccc    8760
cagaagcaac ccttaaccaa tgattaaaata aagtggatga ttacataccc aagctccttc    8820
aactcccagg gacataattc tgaggtgggt gtatgtttat cccttttttca agaacttccc    8880 cgaaggatta agcttcagtc acccactggt aaattgctta acagctcaac ctctatgggt    8940
ttgggttgct ttttcttgta tcacatgctg tctcctttat ggtgtacact gcactttcca    9000
aattgactac ctatacttga atcctgtctt agatgtattt ctggaggaac tcaaactaag    9060
gcagatgggg aactatagat taaatgaaac ttaagagatg tcaaccaact gcaaagtgtg    9120
gagctgagca aaaacaaaa caaacaaaa caaacaaaaa aactgttcaa aaagtttatg    9180
agacaatcag ggatatttaa atactgactg aatattttat aacatttaga aattattggg    9240 gttttaggt ggcataatac tgataggctt atctctaaac ccatgatcaa atattggata    9300
tttatagatg aaatgttagg atgtctggga tttgctttca aattaatatg gagtggagtt    9360
gtgattggtg atgagttgac aattattaaa actgggcact agtatgtgag actttatgat    9420
accattctgt ccacttttgt agatgttgga aattttccct aattagatac aaaaatgaaa    9480
```

```
aaagctgaaa gctctatggg gattgttaat aactatgttc ttagtgctta acagtgttca    9540
gtacatagtc aacaaagaag cactcaaaac actattcatt gaacaactgt tttgtcttat    9600
gttggggata ccaaggcaaa tattgttgac attgacattt ttagctgaca tactggaaat    9660
cttaccaaga gttttataca gactagagga aaaaaatcat tttatcaatt agtacaatgt    9720
cgggttcaaa aatgttata ctaggtctac ttctaactaa agtattttc agcttgtgat    9780 tcatcaccgt ctgtgtcttg aaggtatatt tgagttaaca tatattttat tagaatgtgc    9840
tgttttttgc caaaatgctg gaatttctgg gatactttga tgattcagtt ggacagaata    9900
tgacactgaa tatttgaaag caggacttgg ttagaaaatc taagattgtg agtgccgaat    9960
ttacctagta gatatatgtt tctgaaattt acaaggtaac tgcttttgtt gggaccaaaa   10020
ccacacagcc aataaaacta aaactgtact gggaaaatca tttaaataaa agaatagtat   10080
attaagttgg agggtagggt atatttgaag tcttagaggc atgtaaacag gaacttgcaa   10140
gaaattccag cagaaatttt ccactttaaa aaatatagat aaagctgggc acagtagggc   10200
atgtctgtag tcccagctac ttgggaggct atggcaggag gatcacttga ggccaggagt   10260
tcaaggctgt aatacgccta gattgtacct gtgaatagcc actgcactcc agcctgggca   10320
acatagcaag attccatctc taaaaaaata taaatttgat atagatgtat ctatatatct   10380
gtctctaaaa aattctgtca cttccatgag ttcacattat tgctgagatt tattttcttg   10440
caagattttc taataacatg atagtccttg ttttcaagct gtcaggtagt aaaacagtaa   10500
tttaatttgg caataacata tgacattcta agaagacgca ttagaaggtt tttaagaagt   10560
gtactgaaat attttttggaa tgtccttcaa acaggcaaag tttaaactgg aaagagcaaa   10620
aagttaaata ttatatattt ataaaaagtc aaactatttt ttccttacct ggttaaaaag   10680
gtgttaccaa ggtcgcaaaa tagctttgta tattaaaaat ttttttttatt ggattaattc   10740 ctagttgtag tttagctact tattttttgtt tttcatttat cttttcacc tctatgtagc   10800 ttatgttatt aagttatgtt attaagtttt taaataaaac ctaggaggct tcttaattct   10860
ttatgaaaaa ttctgtgaga ataactagct aaatttttaaa actacaacca aataagattg   10920
acataataat atgcatatac attgctcttc tcacattaac aataatagat ttgtatcttc   10980
taagatatct ctgagaataa aatttccagc catatcatca gctaaattaa ctcaaattta   11040
ctatctggat ttggctgttt cacttgtagg ttaaaagtta aaaggtttgc tatttcttgg   11100
aatcaaaggt tatttaatga aagaagatta atttcaataa atgatgcatt taaagttttt   11160
tccaacaaag agtgtaagag atttatcaca ggttctaaat aacaaattta atttccctaa   11220
catgttaagg agaattttgg ttcccgcaga ggactgagtg gactaatcat ttataataag   11280
actgacttta aacttccttt taacttgaca gtagttaatt ctaactttat taaattagaa   11340
tccccattaa ttcacccatt tttctttcac caattttgtt ttacaattaa ggtttatctg   11400
cagagttctg ttttgaccat tatgctgaaa gtgctgagtt ctgctgtttg ccttccttca   11460
gcctttctgg ctgaatggct tcctgaatct tctcagaggt ttccctctga gcccatgatg   11520
gggttctaaa agcacattct gttcatgtac tgggatagtg ggatgtgagg gcagagaagt   11580
tcttcctgag catgagtcct tcatcctcta cccactgttt tataaacctg tctcaaattc   11640
catgcacttt tggacccagt tacttgaact ctcaggagca ggtactttgt cacctccaga   11700
gggaaggcca gcatcctcct agcgggtact gctgtgtgct tgcccctgag ccaggagctt   11760
tgcatttgct ctctcatttg atccccctcaa caaccctagt agtgaggaaa tatctatttc   11820
```

```
atacatgagg aaattgaggc ccagagaagg cactggctgc ttagctgtgt gctgtcaccc   11880
tgttgaaacc aacgcctcct gcctacactg ccactgcctg tataaactgg tgccacccac   11940
ggttatatgg cagaaagcag tgcttcgaga aaatggacca gcaaccgcca tgtgttgaac   12000
aggctatggg caggaggaaa taaagcagtt ataggcacctg ggggtggaag tcaaggcagt   12060
aaccaaaata aagtgggagc acggaaaaaa gctggggaaa taaaaaggtt caaatttcac   12120
atttcctcat gaagtccaga tcaagttgga gcttgtttaa tagcagaaat taggcagcca   12180
gacctgtctg tagggcaaag aaattttgt tgaaaagccc agcaagtatt tactccgctg    12240
taacagagtc ttttctaac tccaggatct tttctttgtg tgctctgtag aatgaagtgt    12300
gcttgttttg gtggggatac atttacacag ttctccatgt tttgtttcat ctttcctctc   12360
cgtgttgttg ctctcttttt cctttgctct atccaaagat atcagccaaa gaagccaaga   12420
aaaatgttat ctttactta gaattaggga tttcagatat gggtagatgg ctctgttagg    12480
cagaagtgtc agagctggtt ataggaaaac caggcggcac atacatgatc ccagacaccg   12540
aagtaacctc tgtctcactc ctccacttcc agcaaggtat tgtgctctga ggggctgatg   12600
agagaaggta gattatgggt ctgccaaggc ttttactgg tctctgttta tcttttctg     12660 agtgccaatt cagcatgatc tagaccagga tcatttgttt gcagggatgg aaaacaaact   12720
gaaactggct caagtgaatg ctcactggaa ggcttactgg aaaacttact ggaaggatgt   12780
gaggacatgt tcgggaatct atttgcagaa aacatattca ggtatactgg gagctctccc   12840
tctctcacat tgtctccctc actgaaacca ggattgctgt ctatttcctt ggggctgttg   12900
ctgtcatgct gtcttactaa ctgtagtgtt gtgttagcta cacgactgct caagtttatt   12960
tttttgaaaa attgtgttcc atttagccag gatgatgcaa gttgtttcaa gaaaggctat   13020
aaaatgcttg caataaaagt catgttcatt cacattcatt aggaaaaaat gaaataaatc   13080
tatgctgcat aacttttttc atgccaagtg cgggagtgga ggttgtcaaa tcaagactgg   13140
atcatcaagt acataatgat agggtgccaa aattccaagg aggttgggag tcactgttgt   13200
tgagggtggt caaagaattt gtttccccac aaggcatgtg gctttgggcc agcacacctc   13260
ataattcgtt ctcttctatt tcccacatcc gtcttataat gtctcaattt aaccagggga   13320
atatggagcg tgaactcttt ctatttaccc ttttaacatc caggtagata tttctgagat   13380
acatggcaat gtatcagggt tgagtttgct gctctggttc ttatcctttt tttttgagac   13440
aggttcttgc tctgttgccc aggctggaat gcagtggtgc aatctcagct cactgcagac   13500
tctgcctctg cctcttaagt ttaagtgatc ctcgtgcctc agcctcctga gtagctgaga   13560
ttaccggcac ctgccattgt gcccagctaa tttttgtatt tttaataatg gtgaggtttc   13620
accatgttgc ccaggctggt ctcgaactcc tggcctcaag tgatccactt gctttggcct   13680
cccaaagtgc cgggattaca ggtatgagcc accatgccta gcctctggtt cttatccttt   13740
tgaaagtctt aaagtctcct cttcattcat gtatcaaata tttgatgaaa tatttgacca   13800
gatgtcagag tctagaacat cagaccgaga tagtaaacca gtgggtcgta aatagctaca   13860
tgaagggcat agaatctaaa cagatccaga gtgagagatt aaggtcaagg aactggaagg   13920
catatctgga tttatttatt ttttttaaaa aaatacagta tttgtttgga tggagaatgg   13980
aaatagaact tgcagttttg gttctctgca atgcaggttg gccactgcta ttgctgtaac   14040
tctgtcctat tgtcctaccc atactactgt tgtaacttcc ataaggtggg acctgatgaa   14100
tcacgcacac ttccagagtg tttggtcagg gtgaccctgg gtgcagcaag gatggccaat   14160
gctgttggca tcaaaaggcc aagagatgac tttggtcaga ttagataaag accatttagg   14220
```

```
gccatggaga tatggaagca attttcttct ttcctagaag atgatgcaat agatgacaat    14280
aagcatttgg gtgaatctct ccagccaggt ttgaaggcag tttgtgtcac gtagtgggtg    14340
ggtggatggg gaaagttagt tctaattact attccagggc cctacatcca gaacctttcc    14400
attttaagac aagaggggga ctaacattcc cagctcattc gcaaatgact caagagaatg    14460
ggacagagga aagggagata ccattttttaa ttcccctgg aggagtccta atgtcccatt     14520
agtgtttcaa ctgtttggtc taattcaggt atgaagtaca gtggtttgtt tgtttgtttg    14580
tttgttttgt ttttgtttt tcataaaatt ggttgattga ttaataaatt gcttgctggg     14640
cattggggaa ctatacatga aaattatatg actttaaccc tgaaggagct cagaatctaa    14700
tgcggaagat ggatatttat gatatataac aagggcaaca ataaatctag tacaagatat    14760
gaggaatctt ccaggctttg tattggacaa aatgtctctg ggatgtcctt tacctggagg    14820
catatatggg cccaatgcca gcttcagcta ttctaaaaga gacctgagtc taaagatcac    14880
acattatctc atatcaggag ccatgctcac tgactgaaat ttcccagtgg ccaccaagct    14940
atcattatgg tccctatagt cccactaatt attatccatc ccactttgct acttctggat    15000
cggacacttg acagataatg tcagggacag tatagcgtgt gttttgccca aatgatcttt    15060
aagacagcct cgttcccagt ctggcggttg tgtgggaatc agcatcttca cttcctgatt    15120
tctattacac tccttcctac agccctgtcc accacagcca gctggctgaa gagctcaaaa    15180
ggcaagaaat cagcaagaga gagagatgaa gcatgagaaa tgagcaaaaa acacccagca    15240
catcataatc ttggacagtt tagcagtaca tgaaaataga tggtcctcgc cccaagggac    15300
tgcagtaacc ctgaataaac aggatgtctc tcacttttag cagttctttc tgtgctagta    15360
ttggggaaat atattttgg ctgcatgcaa aatggtaaaa gacatctatt aagaaaatga     15420
aaacaatgct tctgttttag acgaagcttt tgaaggttta aggatcacct atttattgac    15480
aaaattgttt ccgtggctta aaaataaaat acaaacaaat actacaggta ttcttgcctt    15540
ctcattctac ttaaaatcac atttccaaag actttcttct ctacttaaaa acaggaatta    15600
agaaatactc aaaagagatc ctagacaaaa ctaacatttc agcaaccaaa gataaatcat    15660
gcttttagag gaagatgcta ggttctagaa tctctctgaa caccgtgtag cactaagaaa    15720
ctacaatcac tggctgagac cttgatcaaa taatggctaa catataagat gcttattcta    15780
gtcaggcaca cttctaagag ctgtatatct gctaattcat ttattctcct aggatataaa    15840
ggatcagcag atccttcagg ctctggtatg ttctgagatg agttaaccca gaaattgtca    15900
tcaaaagaca gattcagcaa aacgaaaaca gccaccattt tatgtagatg tccctgtggt    15960
ttagtgctac agaccggaca tttgtgccct taggggaaaa atgatgaggt cagagcagac    16020
tgggatagat caggtctggt gctttttattg tagatcctgg aaccaaagat gatcttatgg    16080
aaagccaggt agacagttca gctgaggtat tcatccatag agactggcca                16130

<210> SEQ ID NO 2
<211> LENGTH: 87
<212> TYPE: DNA
<213> ORGANISM: Homo sapiens

<400> SEQUENCE: 2
agaatgccaa agagcagcag gatggatcca gcatcctctc ctgataaaag agggctagaa       60
gacgggaggc tccgggaagt ctactgg                                          87

<210> SEQ ID NO 3
```

```
<211> LENGTH: 279
<212> TYPE: DNA
<213> ORGANISM: Homo sapiens

<400> SEQUENCE: 3
agtcatgaag acactgaaaa gtgatgaatc cacataacca tgacactgga aatgaagttt      60
gagtggcagt cagaatctgg gaggaagcat tgctaagtga aaatcttatg gagcttgact     120
aaaaatccct gtcaggaacc gtcaaaagct gtgtccctga catgaaaaat cttgctggaa     180
gttgagagag gtttatgcct actccgtgat ccgggaacac aagacctta  ccaaccaaaa     240 aagtggatag ctgttcttct gctgtgaagg ttaataaag                            279

<210> SEQ ID NO 4
<211> LENGTH: 115
<212> TYPE: DNA
<213> ORGANISM: Homo sapiens

<400> SEQUENCE: 4
aacgccagaa gtgccaagca attaacaacc ccagaagcaa cccttaacca atgattaaat      60
aaagtggatg attacatacc caagctcctt caactcccag ggacataatt ctgag          115

<210> SEQ ID NO 5
<211> LENGTH: 117
<212> TYPE: DNA
<213> ORGANISM: Homo sapiens

<400> SEQUENCE: 5
ggatggaaaa caaactgaaa ctggctcaag tgaatgctca ctggaaggct tactggaaaa      60
cttactggaa ggatgtgagg acatgttcgg gaatctattt gcagaaaaca tattcag       117

<210> SEQ ID NO 6
<211> LENGTH: 148
<212> TYPE: DNA
<213> ORGANISM: Homo sapiens

<400> SEQUENCE: 6
ccctgtccac cacagccagc tggctgaaga gctcaaaagg caagaaatca gcaagagaga      60
gagatgaagc atgagaaatg agcaaaaaac acccagcaca tcataatctt ggacagttta    120
gcagtacatg aaaatagatg gtcctcgc                                       148

<210> SEQ ID NO 7
<211> LENGTH: 20
<212> TYPE: DNA
<213> ORGANISM: Artificial sequence
<220> FEATURE:
<223> OTHER INFORMATION: synthetic primer

<400> SEQUENCE: 7
aggcattgac aacagggttc                                                 20

<210> SEQ ID NO 8
<211> LENGTH: 20
<212> TYPE: DNA
<213> ORGANISM: Artificial sequence
<220> FEATURE:
<223> OTHER INFORMATION: synthetic primer

<400> SEQUENCE: 8
gttgcacatc agcagcactt                                                 20
```

```
<210> SEQ ID NO 9
<211> LENGTH: 20
<212> TYPE: DNA
<213> ORGANISM: Artificial sequence
<220> FEATURE:
<223> OTHER INFORMATION: synthetic primer

<400> SEQUENCE: 9
aagagggcta gaagacggga                                              20

<210> SEQ ID NO 10
<211> LENGTH: 21
<212> TYPE: DNA
<213> ORGANISM: Artificial sequence
<220> FEATURE:
<223> OTHER INFORMATION: synthetic primer

<400> SEQUENCE: 10
ggacacagct tttgacggtt c                                            21

<210> SEQ ID NO 11
<211> LENGTH: 20
<212> TYPE: DNA
<213> ORGANISM: Artificial sequence
<220> FEATURE:
<223> OTHER INFORMATION: synthetic primer

<400> SEQUENCE: 11
actttgtcaa gctcatttcc                                              20

<210> SEQ ID NO 12
<211> LENGTH: 20
<212> TYPE: DNA
<213> ORGANISM: Artificial sequence
<220> FEATURE:
<223> OTHER INFORMATION: synthetic primer

<400> SEQUENCE: 12
cacagggtac tttattgatg                                              20

<210> SEQ ID NO 13
<211> LENGTH: 20
<212> TYPE: DNA
<213> ORGANISM: Artificial sequence
<220> FEATURE:
<223> OTHER INFORMATION: synthetic primer

<400> SEQUENCE: 13
tagccctaaa cctcaacagt                                              20

<210> SEQ ID NO 14
<211> LENGTH: 23
<212> TYPE: DNA
<213> ORGANISM: Artificial sequence
<220> FEATURE:
<223> OTHER INFORMATION: synthetic primer

<400> SEQUENCE: 14
tgcgcttact ttgtagcctt cat                                          23

<210> SEQ ID NO 15
<211> LENGTH: 24
<212> TYPE: DNA
<213> ORGANISM: Artificial sequence
<220> FEATURE:
<223> OTHER INFORMATION: synthetic primer
```

```
<400> SEQUENCE: 15
gggagatacc atgatcacga aggt                                          24

<210> SEQ ID NO 16
<211> LENGTH: 26
<212> TYPE: DNA
<213> ORGANISM: Artificial sequence
<220> FEATURE:
<223> OTHER INFORMATION: synthetic primer

<400> SEQUENCE: 16
ccacaaatta tgcagtcgag tttccc                                        26

<210> SEQ ID NO 17
<211> LENGTH: 20
<212> TYPE: DNA
<213> ORGANISM: Artificial sequence
<220> FEATURE:
<223> OTHER INFORMATION: synthetic primer

<400> SEQUENCE: 17
gacggaggtt gagatgaagc                                               20

<210> SEQ ID NO 18
<211> LENGTH: 20
<212> TYPE: DNA
<213> ORGANISM: Artificial sequence
<220> FEATURE:
<223> OTHER INFORMATION: synthetic primer

<400> SEQUENCE: 18
attcggggct ctgtagtcct                                               20

<210> SEQ ID NO 19
<211> LENGTH: 20
<212> TYPE: DNA
<213> ORGANISM: Artificial sequence
<220> FEATURE:
<223> OTHER INFORMATION: synthetic primer

<400> SEQUENCE: 19
gacttgagct gctccggaat                                               20

<210> SEQ ID NO 20
<211> LENGTH: 20
<212> TYPE: DNA
<213> ORGANISM: Artificial sequence
<220> FEATURE:
<223> OTHER INFORMATION: synthetic primer

<400> SEQUENCE: 20
ggctagggct ggtttcactt                                               20

<210> SEQ ID NO 21
<211> LENGTH: 20
<212> TYPE: DNA
<213> ORGANISM: Artificial sequence
<220> FEATURE:
<223> OTHER INFORMATION: synthetic primer

<400> SEQUENCE: 21
gcgaagtgaa attgcattga                                               20

<210> SEQ ID NO 22
<211> LENGTH: 22
```

<212> TYPE: DNA
<213> ORGANISM: Artificial sequence
<220> FEATURE:
<223> OTHER INFORMATION: synthetic primer

<400> SEQUENCE: 22
cgaccaaaca cagaaaagac aa                                      22

<210> SEQ ID NO 23
<211> LENGTH: 22
<212> TYPE: DNA
<213> ORGANISM: Artificial sequence
<220> FEATURE:
<223> OTHER INFORMATION: synthetic primer

<400> SEQUENCE: 23
cctctcttcc gatatcccat ca                                      22

<210> SEQ ID NO 24
<211> LENGTH: 17
<212> TYPE: DNA
<213> ORGANISM: Artificial sequence
<220> FEATURE:
<223> OTHER INFORMATION: synthetic primer

<400> SEQUENCE: 24
gggaaccgga gaacatc                                            17

<210> SEQ ID NO 25
<211> LENGTH: 20
<212> TYPE: DNA
<213> ORGANISM: Artificial sequence
<220> FEATURE:
<223> OTHER INFORMATION: synthetic primer

<400> SEQUENCE: 25
gccctcaaga agatggtgtg                                         20

<210> SEQ ID NO 26
<211> LENGTH: 21
<212> TYPE: DNA
<213> ORGANISM: Artificial sequence
<220> FEATURE:
<223> OTHER INFORMATION: synthetic primer

<400> SEQUENCE: 26
ccagggattt ctcttctttc c                                       21

<210> SEQ ID NO 27
<211> LENGTH: 18
<212> TYPE: DNA
<213> ORGANISM: Artificial sequence
<220> FEATURE:
<223> OTHER INFORMATION: synthetic primer

<400> SEQUENCE: 27
cctgtgagct ggaggcac                                           18

<210> SEQ ID NO 28
<211> LENGTH: 18
<212> TYPE: DNA
<213> ORGANISM: Artificial sequence
<220> FEATURE:
<223> OTHER INFORMATION: synthetic primer

<400> SEQUENCE: 28
caggtcagtg ccccgttg                                                    18

<210> SEQ ID NO 29
<211> LENGTH: 20
<212> TYPE: DNA
<213> ORGANISM: Artificial sequence
<220> FEATURE:
<223> OTHER INFORMATION: synthetic primer

<400> SEQUENCE: 29
tgcttccgtt tcctctccta                                                  20

<210> SEQ ID NO 30
<211> LENGTH: 21
<212> TYPE: DNA
<213> ORGANISM: Artificial sequence
<220> FEATURE:
<223> OTHER INFORMATION: synthetic primer

<400> SEQUENCE: 30
tgtcagccca ctgtttacct t                                                21

<210> SEQ ID NO 31
<211> LENGTH: 21
<212> TYPE: DNA
<213> ORGANISM: Artificial sequence
<220> FEATURE:
<223> OTHER INFORMATION: synthetic primer

<400> SEQUENCE: 31
uuauggagcu ugacuaaaat t                                                21

<210> SEQ ID NO 32
<211> LENGTH: 21
<212> TYPE: DNA
<213> ORGANISM: Artificial sequence
<220> FEATURE:
<223> OTHER INFORMATION: synthetic primer

<400> SEQUENCE: 32
uuuuagucaa gcuccauaag a                                                21

<210> SEQ ID NO 33
<211> LENGTH: 21
<212> TYPE: DNA
<213> ORGANISM: Artificial sequence
<220> FEATURE:
<223> OTHER INFORMATION: synthetic primer

<400> SEQUENCE: 33
caguaacccu gaauaaacat t                                                21

<210> SEQ ID NO 34
<211> LENGTH: 21
<212> TYPE: DNA
<213> ORGANISM: Artificial sequence
<220> FEATURE:
<223> OTHER INFORMATION: synthetic primer

<400> SEQUENCE: 34
uguuuauuca ggguuacugc a                                                21

<210> SEQ ID NO 35
<211> LENGTH: 21
<212> TYPE: DNA
<213> ORGANISM: Artificial sequence

```
<220> FEATURE:
<223> OTHER INFORMATION: synthetic primer

<400> SEQUENCE: 35
uauggguuca uccaggucug a                                              21

<210> SEQ ID NO 36
<211> LENGTH: 21
<212> TYPE: DNA
<213> ORGANISM: Artificial sequence
<220> FEATURE:
<223> OTHER INFORMATION: synthetic primer

<400> SEQUENCE: 36
agaccuggau gaacccauat t                                              21

<210> SEQ ID NO 37
<211> LENGTH: 21
<212> TYPE: DNA
<213> ORGANISM: Artificial sequence
<220> FEATURE:
<223> OTHER INFORMATION: synthetic primer

<400> SEQUENCE: 37
ucguggacua gcagaaucct t                                              21

<210> SEQ ID NO 38
<211> LENGTH: 21
<212> TYPE: DNA
<213> ORGANISM: Artificial sequence
<220> FEATURE:
<223> OTHER INFORMATION: synthetic primer

<400> SEQUENCE: 38
ggauucugcu aguccacgat t                                              21

<210> SEQ ID NO 39
<211> LENGTH: 23
<212> TYPE: DNA
<213> ORGANISM: Artificial sequence
<220> FEATURE:
<223> OTHER INFORMATION: synthetic primer

<400> SEQUENCE: 39
gttcccggat cacggagtag gca                                            23

<210> SEQ ID NO 40
<211> LENGTH: 21
<212> TYPE: DNA
<213> ORGANISM: Artificial sequence
<220> FEATURE:
<223> OTHER INFORMATION: synthetic primer

<400> SEQUENCE: 40
ggacacagct tttgacggtt c                                              21

<210> SEQ ID NO 41
<211> LENGTH: 16
<212> TYPE: DNA
<213> ORGANISM: Artificial sequence
<220> FEATURE:
<223> OTHER INFORMATION: Antisense oligonucleotide

<400> SEQUENCE: 41
caacttccag caagat                                                    16
```

<210> SEQ ID NO 42
<211> LENGTH: 16
<212> TYPE: DNA
<213> ORGANISM: Artificial sequence
<220> FEATURE:
<223> OTHER INFORMATION: Antisense oligonucleotide

<400> SEQUENCE: 42
agaactgcta aaagtg                                                    16

METHODS AND COMPOSITIONS FOR MODULATING LNCRNAS AND METHODS OF TREATMENT BASED ON LNCRNA EXPRESSION

CROSS-REFERENCE TO RELATED APPLICATIONS

This application claims priority from U.S. Provisional Application Ser. No. 62/965,984 filed on 26 Jan. 2020, which is incorporated herein by reference in its entirety.

STATEMENT REGARDING FEDERALLY SPONSORED RESEARCH OR DEVELOPMENT

This invention was made with government support under CA091842 awarded by the National Institutes of Health. The government has certain rights in the invention.

Material Incorporated-by-Reference

The Sequence Listing, which is a part of the present disclosure, includes a computer readable form comprising nucleotide and/or amino acid sequences of the present invention. The subject matter of the Sequence Listing is incorporated herein by reference in its entirety.

FIELD OF THE INVENTION

The present disclosure generally relates to therapies for cancer and metastatic cancer.

SUMMARY OF THE INVENTION

Among the various aspects of the present disclosure is the provision of a methods and compositions for modulating lncRNAs and methods of treatment based on lncRNA expression. An aspect of the present disclosure provides for a method of treating a subject, modulating RAMS, or increasing drug sensitivity in a subject having cancer or suspected of having cancer, comprising: detecting long noncoding RNAs (lncRNAs) associated with metastasis (RAMS) in a biological sample comprising lncRNA. In some embodiments, a level of at least one of RAMS1 to RAMS148 are measured, or the subject is treated according to the levels of the at least one of RAMS1 to RAMS 148. Another aspect of the present disclosure provides for a method of inhibiting an upregulated RAMS associated with a bad outcome or increasing drug sensitivity, comprising: reducing expression of an upregulated RAMS associated with a bad outcome comprising genomic editing a cell or a subject; or reducing expression, signaling, activity, or function an upregulated of a RAMS comprising administering a RAMS modulating agent to a cell or a subject. Yet another aspect of the present disclosure provides for a method of predicting treatment response or outcome in a subject having or suspected of having cancer comprising: detecting RAMS levels in a biological sample comprising lncRNA; determining the levels of the RAMS in the sample; (i) if RAMS RAMS11, RAMS16, RAMS22, RAMS35, RAMS39, RAMS46, RAMS50, RAMS71, or RAMS74 are elevated, then the subject is predicted to have a bad outcome; or (ii) if RAMS RAMS17, RAMS18, RAMS26, RAMS62, or RAMS64 are elevated then the subject is predicted to have a good outcome.

Yet another aspect of the present disclosure provides for a method of predicting response to a cancer treatment and/or development of resistance, comprising: (i) obtaining a first biological sample from the subject; (ii) measuring or detecting levels of RAMS expression in the first biological sample; (iii) administering the cancer treatment to the subject; (iv) obtaining a second biological sample from the subject at a later time; (v) measuring or detecting levels of RAMS in the second biological sample; and/or (vi) comparing levels of RAMS expression in the second biological sample to the first biological sample. In some embodiments, reduced levels of upregulated RAMS associated with bad outcomes in the second biological sample indicates that the subject is responding to the cancer treatment; greater than or equal levels of upregulated RAMS associated with bad outcomes in the second biological sample indicates that the subject is not responding to the cancer treatment; enhanced levels of upregulated RAMS associated with good outcomes in the second biological sample indicates that the subject is responding to the cancer treatment; or less than or equal levels of RAMS associated with good outcomes in the second biological sample indicates that the subject is not responding to the cancer treatment. In some embodiments, the methods further comprise modulating RAMS expression via genomic editing or inhibiting RAMS11 comprising genomically deleting one or more exons in RAMS11. In some embodiments, the methods further comprise modulating RAMS expression comprising administering a RAMS modulating agent to the subject. In some embodiments, if elevated RAMS 11 is detected, the subject is not treated with a topoisomerase inhibitor. In some embodiments, if elevated RAMS11 is not detected, the subject is treated with a topoisomerase inhibitor. In some embodiments, the topoisomerase inhibitor is a TOP1 inhibitor or a TOP2α inhibitor. In some embodiments, if elevated levels of RAMS11 are detected, the subject is administered a therapeutically effective amount of: a kinase inhibitor, an alkylating agent, an antineoplastic antibiotic, an anthracycline antibiotic, or an antineoplastic agent (e.g., a topoisomerase inhibitor). In some embodiments, if RAMS11 is not elevated, the subject is administered a therapeutically effective amount of Gemcitabine, Floxuridine (FUDR), Doxorubicin HCL, Epirubicin HCL, Daunorubicin HCL, or Idarubicin. In some embodiments, RAMS11 is upregulated and the RAMS modulating agent is a RAMS11 inhibiting agent. In some embodiments, the methods further comprise administering an antisense oligonucleotide (ASO), wherein the ASO is against an exon of RAMS11 if elevated RAMS11 is detected. In some embodiments, the ASO is capable of silencing at least one exon of RAMS11. In some embodiments, the ASO is capable of silencing at least two exons of RAMS11. In some embodiments, the ASO targets one or more RAMS11 exons selected from the group consisting of:

(SEQ ID NO: 2)
AGAATGCCAAAGAGCAGCAGGATGGATCCAGCATCCTCTCCTGATAAAAG

AGGGCTAGAAGACGGGAGGCTCCGGGAAGTCTACTGG;

(SEQ ID NO: 3)
AGTCATGAAGACACTGAAAAGTGATGAATCCACATAACCATGACACTGGA

AATGAAGTTTGAGTGGCAGTCAGAATCTGGGAGGAAGCATTGCTAAGTGA

AAATCTTATGGAGCTTGACTAAAAATCCCTGTCAGGAACCGTCAAAAGCT

GTGTCCCTGACATGAAAAATCTTGCTGGAAGTTGAGAGAGGTTTATGCCT

ACTCCGTGATCCGGGAACACAAGACCTTTACCAACCAAAAAAGTGGATAG

CTGTTCTTCTGCTGTGAAGGTTAATAAAG;

-continued (SEQ ID NO: 4)
AACGCCAGAAGTGCCAAGCAATTAACAACCCCAGAAGCAACCCTTAACCA

ATGATTAAATAAAGTGGATGATTACATACCCAAGCTCCTTCAACTCCCAG

GGACATAATTCTGAG;

(SEQ ID NO: 5)
GGATGGAAAACAAACTGAAACTGGCTCAAGTGAATGCTCACTGGAAGGCT

TACTGGAAAACTTACTGGAAGGATGTGAGGACATGTTCGGGAATCTATTT

GCAGAAAACATATTCAG;

(SEQ ID NO: 6)
CCCTGTCCACCACAGCCAGCTGGCTGAAGAGCTCAAAAGGCAAGAAATCA

GCAAGAGAGAGATGAAGCATGAGAAATGAGCAAAAAACACCCAGCACA

TCATAATCTTGGACAGTTTAGCAGTACATGAAAATAGATGGTCCTCGCCC

CAAGGGACTGCAGTAACCCTGAATAAACAGGATGTCTCTCACTTTTAGCA

GTTCTTTCTGTGCTAGTATTGGGGAAATATATTTTTGGCTGCATGCAAAA

TGGTAAAAGACATCTATTAAGAAAATGAAAACAATGCTTCTGTTTTAGAC

GAAGCTTTTGAAGGTTTAAGGATCACCTATTTATTGACAAAATTGTTTCC

GTGGCTTAAAA;

or a functional fragment or variant thereof, and combinations thereof. In some embodiments, a functional fragment or a functional variant thereof is any insertion, deletion, substitution, or addition that allows the ASO to retain RAMS11 inhibiting activity. In some embodiments, if elevated RAMS11 is detected, the subject is treated with a siRNA against RAMS11. In some embodiments, the siRNA comprises the sequences selected from SEQ ID NO: 31 and 32 or SEQ ID NO: 33 and 34, a functional fragment or a functional variant thereof, and combinations thereof. In some embodiments, the methods further comprise upregulating any one of RAMS78 to RAMS148, wherein the any one of RAMS78 to RAMS148 are downregulated. In some embodiments, the subject is treated with a drug associated with a good outcome, wherein the good outcome is associated with a level of any one of RAMS1 to RAMS148. In some embodiments, the subject is treated with any one or more of a RAMS1 to RAMS148 modulating agent. In some embodiments, the biological sample comprises tumor cells, circulating tumor cells (CTCs), or formalin-fixed paraffin-embedded (FFPE) tissue, or frozen tissue. In some embodiments, the biological sample comprises tumor long noncoding RNAs (lncRNAs). In some embodiments, the biological sample is tumor tissue. In some embodiments, the biological sample is a biopsy sample. In some embodiments, the subject has or is suspected of having colorectal cancer (CRC), lung cancer, prostate cancer, head or neck cancer, kidney cancer. In some embodiments, the subject has or is suspected of having colorectal adenocarcinoma, lung adenocarcinoma, lung squamous cell carcinoma, head and neck squamous cell carcinoma (HNSC), or kidney renal papillary cell carcinoma (KIRP). In some embodiments, a level of RAMS11, RAMS16, RAMS22, RAMS35, RAMS39, RAMS46, RAMS50, RAMS71, or RAMS74 are measured. In some embodiments, a level of RAMS11 is measured. In some embodiments, a level of RAMS17, RAMS18, RAMS26, RAMS62, or RAMS64 is measured. In some embodiments, if elevated levels of any one of RAMS11, RAMS16, RAMS22, RAMS35, RAMS39, RAMS46, RAMS50, RAMS71, or RAMS74 are detected, the subject is determined to be at risk for a bad outcome. In some embodiments, if elevated levels of any one of RAMS11, RAMS16, RAMS22, RAMS35, RAMS39, RAMS46, RAMS50, RAMS71, or RAMS74 are detected, it is determined that a RAMS11, RAMS16, RAMS22, RAMS35, RAMS39, RAMS46, RAMS50, RAMS71, or RAMS74 inhibiting agent is predicted to be beneficial. In some embodiments, if elevated levels of any one of RAMS17, RAMS18, RAMS26, RAMS62, or RAMS64 are detected, the subject is predicted to have a good outcome. In some embodiments, if elevated levels of any one of RAMS17, RAMS18, RAMS26, RAMS62, or RAMS64 are detected, it is determined that re-introduction or upregulation of RAMS17, RAMS18, RAMS26, RAMS62, or RAMS64 expression, signals, or activity are predicted to be beneficial. In some embodiments, elevated or upregulated levels of RAMS11 indicates aggressive CRC. In some embodiments, elevated or upregulated levels of RAMS11 indicate a poor prognosis. In some embodiments, RAMS are detected by transcriptome sequencing. In some embodiments, RAMS are detected by qPCR. In some embodiments, RAMS are detected by RNA in situ hybridization (ISH).

Other objects and features will be in part apparent and in part pointed out hereinafter.

DESCRIPTION OF THE DRAWINGS

Those of skill in the art will understand that the drawings, described below, are for illustrative purposes only. The drawings are not intended to limit the scope of the present teachings in any way.

DETAILED DESCRIPTION OF THE INVENTION

Figure 1:
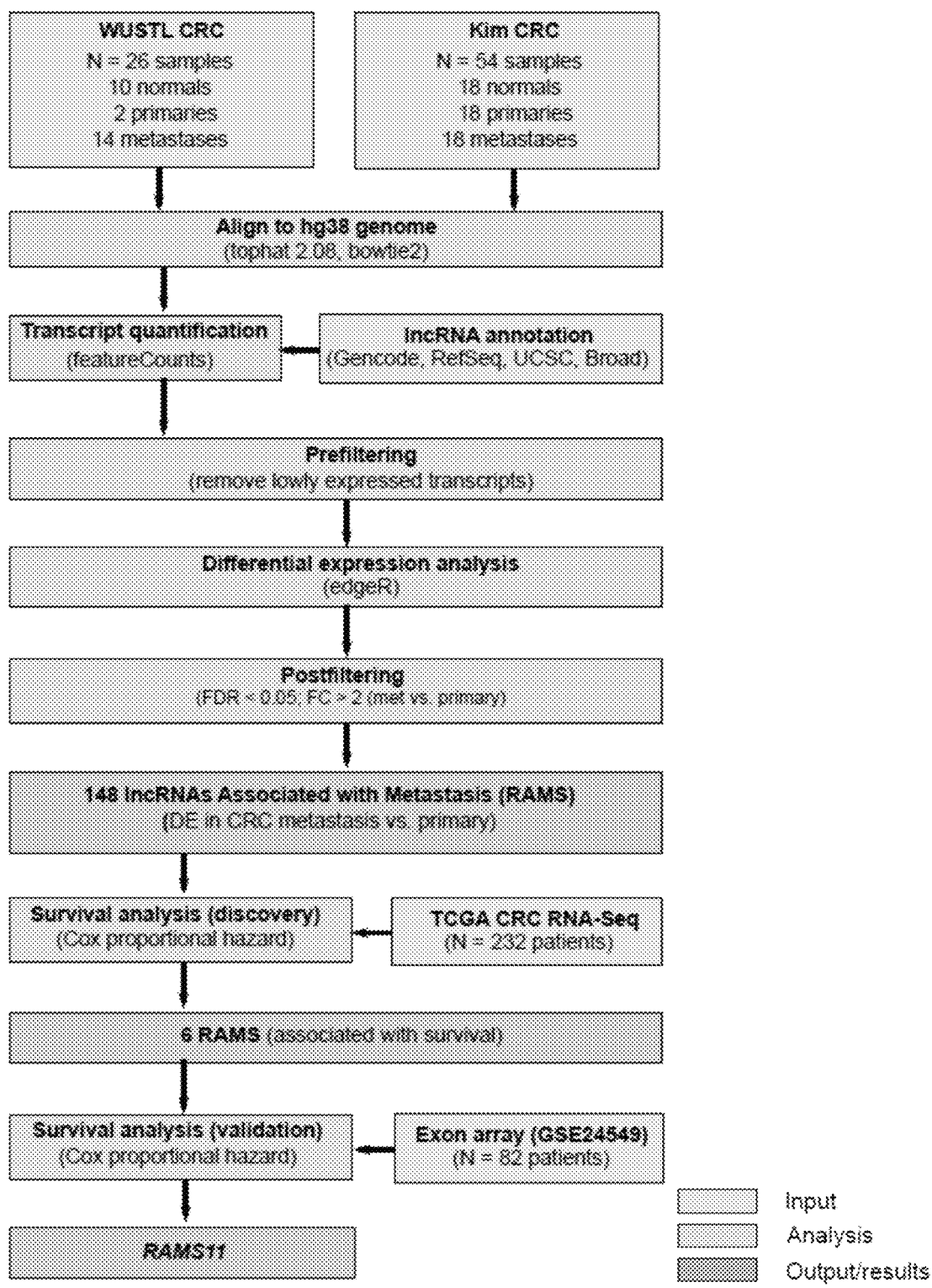
FIG. 1. RNAs associated with metastasis (RAMS). (a) Analysis pipeline for discovery of metastatic CRC lncRNAs. Shaded gray color boxes (input), orange color boxes (analysis), and blue color boxes (output/results). (b) Heatmap of lncRNAs differentially expressed in metastasis compared with primary. Patient samples are indicated on top row shown as normal (green), primary (orange), and liver metastasis (pink). Heatmap color is scaled by row expression Z-score. (c) Kaplan-Meir plots showing RAMS11 association with poor disease-free survival in The Cancer Genome Atlas (TCGA) RNA-Seq and exon array (GSE24549) datasets. Numbers above x-axis are patients at risk at the intervals. p values are inferred from a two-sided logrank test. (d) Average normalized RNA-Seq coverage across WUSTL and Kim cohorts. Normal samples are green boxes, primary samples are orange boxes, and metastatic samples are pink boxes. 5'3' RACE validated five-exon sequence is shown below in blue. RAMS11 expression is significantly higher in (e) MSS patients and (f) CMS2 and CMS4 subtypes. Expression measured as log 2(FPKM+0.01).
Figure 1:
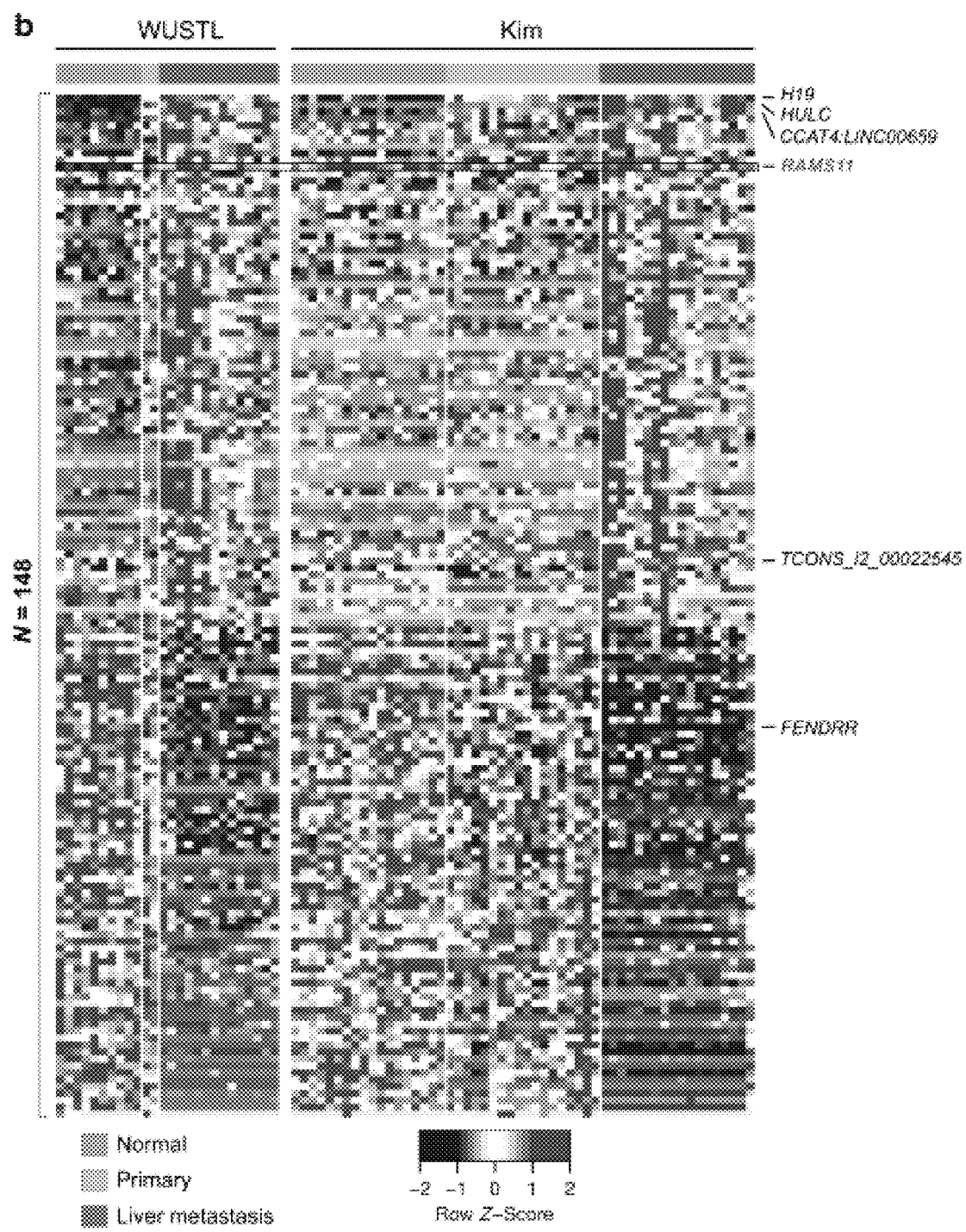
Figure 1:
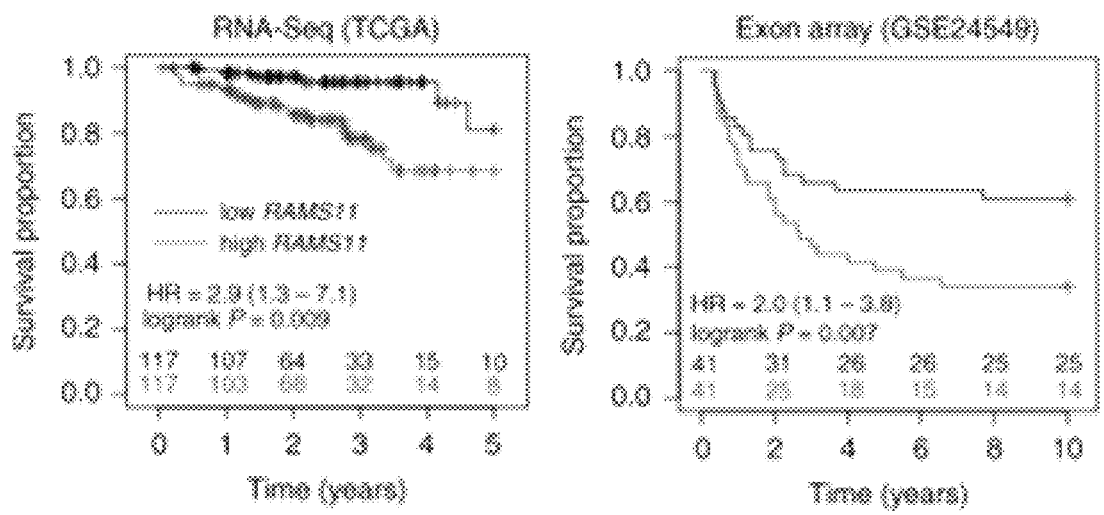
Figure 1:
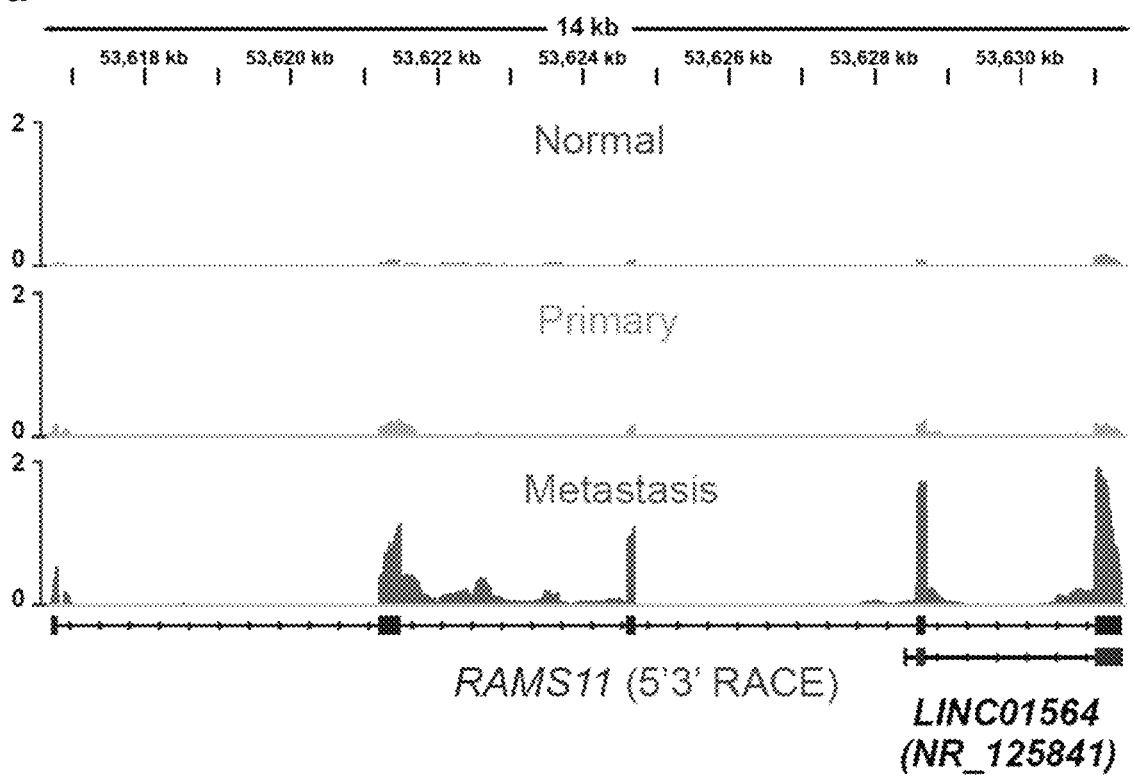
Figure 1:
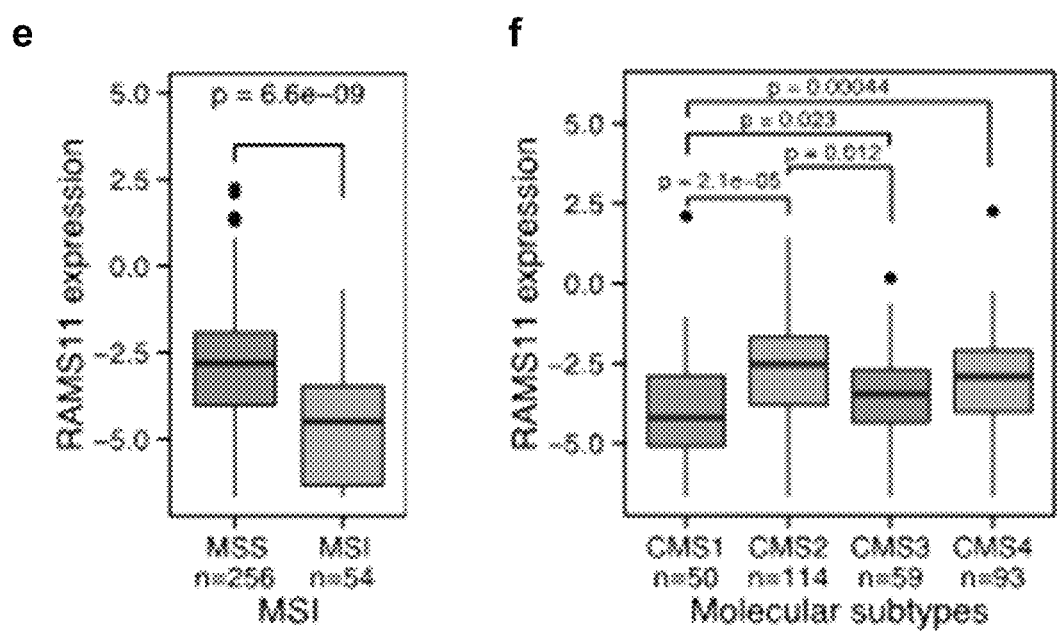

The present disclosure is based, at least in part, on the discovery that lncRNA levels or lncRNA expression are correlated to tumor or cancer invasiveness and drug resistance.

The present disclosure provides for compositions and methods for cancer diagnosis, research, or therapy (e.g., antisense oligonucleotide therapies for long non-coding RNAs), including but not limited to, cancer markers. In particular, the present invention relates to the use of a novel lncRNA as a diagnostic marker and clinical target for cancer (e.g., colon cancer). Furthermore, the present disclosure provides for data demonstrating the utility of a novel lncRNA as a diagnostic marker and clinical target in multiple solid tumors.

The data shown in Example 1 demonstrates the ability of RAMS11 to promote aggressive phenotypes in vitro and in vivo; support RAMS11-dependent CBX4 binding to the TOP2α promoter; high expression of RAMS11 promoted resistance to treatment with 5FU; and the therapeutic potential of target RAMS11 directly with antisense oligonucleotides (ASOs).

While transcriptome sequencing has provided an unbiased method for discovering lncRNAs, existing large-scale sequencing projects such as The Cancer Genome Atlas Network (TCGA)[25] are comprised of predominantly primary tumors lacking matched metastatic samples. This disclosure represents a critical barrier to discovering novel lncRNAs throughout the progression of primary to metastatic disease correlated to treatment response and resistance. To address this, we have conducted a meta-analysis of normal, primary, and distant metastatic tissues from CRC patients across two independent patient cohorts to discover differentially expressed (DE) lncRNAs in metastatic tumors compared with primary tumors, termed RNAs Associated with Metastasis (RAMS).

Long Noncoding RNAs (LNCRNAs) and RNAs Associated with Metastasis (Rams)

LncRNAs are typically greater than 200 nucleotides in length, lack coding potential, are transcribed by RNA polymerase II, spliced, 5' capped, and polyadenylated. LncRNAs are also known to have a role in a diverse range of biological functions, including serving as critical regulators in tumorigenesis and metastasis. Furthermore, their prognostic, diagnostic, and therapeutic potential exemplify their clinical significance. Therefore, the characterization of lncRNAs, elucidating their function, and assessing their clinical applicability could significantly impact metastatic colorectal cancer (mCRC) diagnosis and treatment.

Various RAMS were identified (see e.g., TABLE 1), but RAMS11 was prioritized due to its association with poor disease-free survival across independent patient cohorts and promotion of aggressive phenotypes, tumor growth, and metastasis in vitro and in vivo.

It was discovered that elevated RAMS11 expression increased resistance to topoisomerase inhibitors (e.g., TOP2α inhibitors). As such, detection of RAMS can provide pre-treatment data that can predict response to treatment and development of resistance.

It was also discovered that expression of RAMS11 correlates with resistance of currently used chemotherapies in colorectal cancer. It is presently thought that expression of RAMS11 can correlate with or predict a subject's response to any number of treatments for cancer, such as colorectal cancer. For example, a treatment can be chemotherapy, immunotherapy, radiation therapy, surgery, cryosurgery, targeted therapy (e.g., monoclonal antibody therapy, angiogenesis inhibitors), or radiofrequency ablation.

RAMS11 can comprise any one of, or a combination of, the sequences in TABLE 2 or corresponding RNA sequences thereof.

Detection of RAMS11 can comprise the detection of any one or one or more of the sequences in TABLE 2 or corresponding RNA sequences thereof.

Proliferative Diseases, Disorders, and Conditions (e.g., Cancer)

Figure 12:
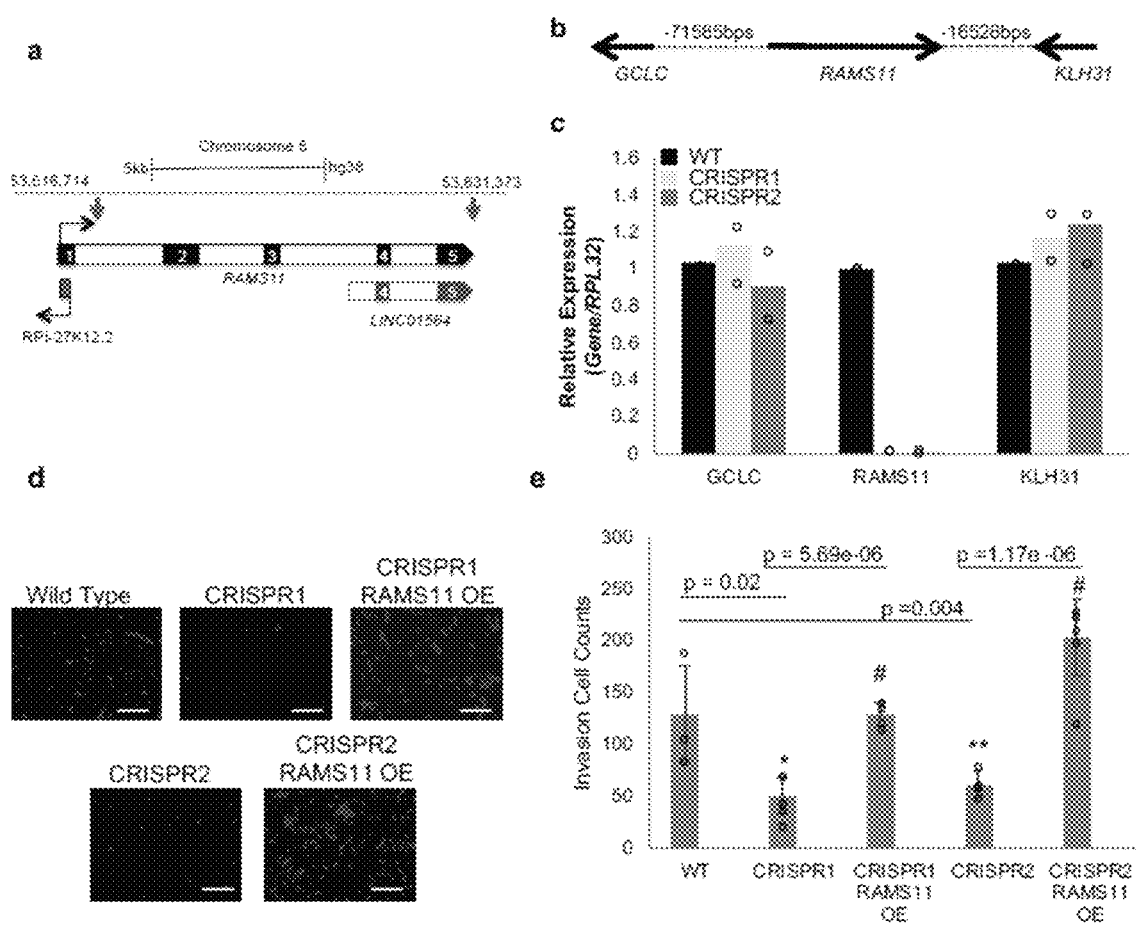
FIG. 12. RAMS11 CRISPR characterization. (a) Region of interest for gDNA deletion. Primers shown by red arrows. Exon 1 (red) overlapped RPI-27K12.2 and was avoided. (b) Schematic showing distance of nearby surrounding genes and (c) qPCR indicating decrease only of RAMS11 expression and not nearby genes in CRISPR cell lines. Experiment repeated two times, n=2 samples for all. (d and e) Transwell images of DAPI stained LoVo Wild Type, CRISPR1 and CRISPR2 cells show decreased invasion, and CRISPR cells with RAMS11 overexpression plasmid (OE) increased invasion. Experiment repeated three times. WT n=4, CRISPR1 n=7, CRISPR1 RAMS11 OE n=5, CRISPR2 n=7, CRISPR1 RAMS11 OE n=6, Bars=25 μM (f and g) Flow cytometry detecting EdU (5-ethynyl-2'-deoxyuridine) incorporation in RAMS11 CRISPR KO cells. Experiment repeated two times with all data n=3. Data is presented as mean values ±s.d and analyzed by two-tailed paired t-test. *p<0.05, **p<0.005, #p<0.0005.
Figure 12:
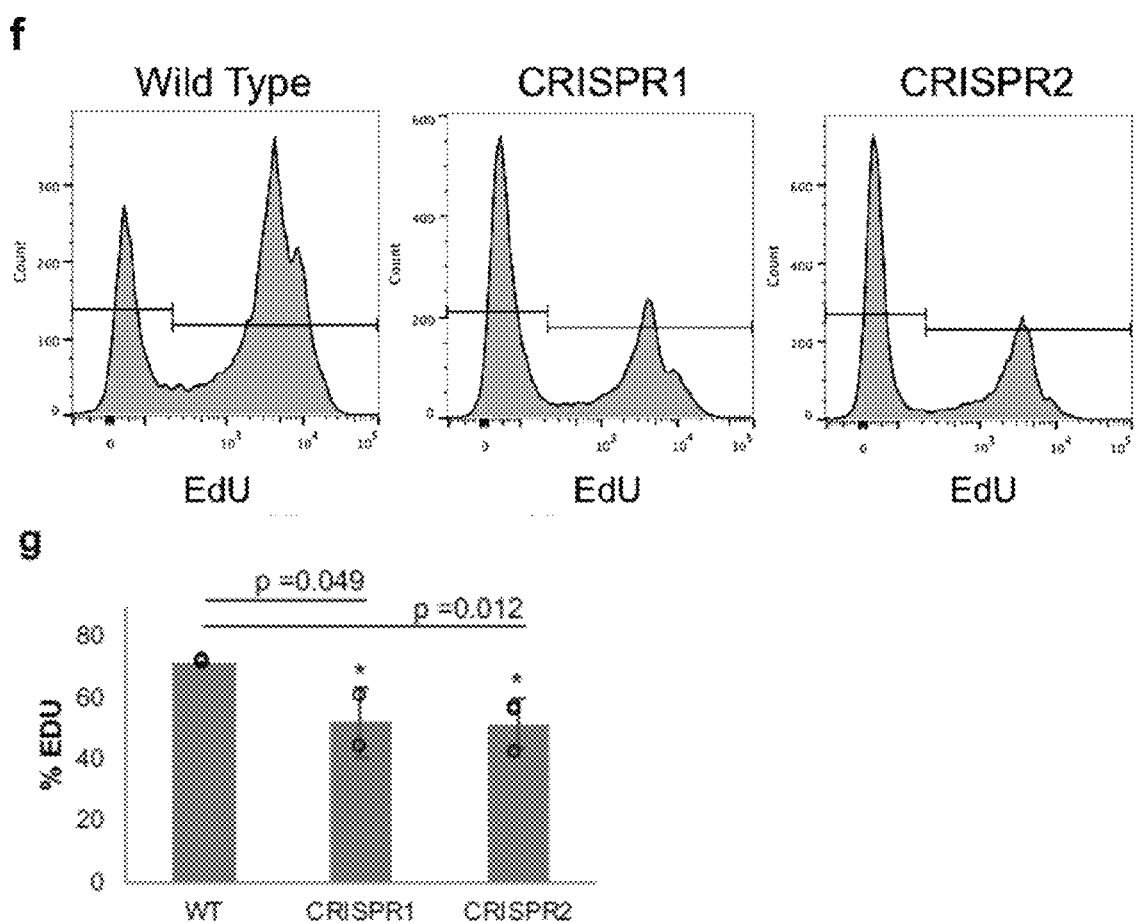

It was discovered that RAMS11 had elevated expression in primary tumors compared to normal tissue of origin in colorectal adenocarcinoma (p<0.00001) and four additional cancer types, including: lung adenocarcinoma (p<0.00001), lung squamous cell carcinoma (p<0.00001), head and neck squamous cell carcinoma (p=0.00001), and kidney renal papillary cell carcinoma (p=0.00001) (FIG. 12a). Methods and compositions as described herein can be used for the prevention, treatment, or slowing of the progression of cancer or tumor growth. For example, the cancer can be Acute Lymphoblastic Leukemia (ALL); Acute Myeloid Leukemia (AML); Adrenocortical Carcinoma; AIDS-Related Cancers; Kaposi Sarcoma (Soft Tissue Sarcoma); AIDS-Related Lymphoma (Lymphoma); Primary CNS Lymphoma (Lymphoma); Anal Cancer; Appendix Cancer; Gastrointestinal Carcinoid Tumors; Astrocytomas; Atypical Teratoid/Rhabdoid Tumor, Childhood, Central Nervous System (Brain Cancer); Basal Cell Carcinoma of the Skin; Bile Duct Cancer; Bladder Cancer; Bone Cancer (including Ewing Sarcoma and Osteosarcoma and Malignant Fibrous Histiocytoma); Brain Tumors; Breast Cancer; Bronchial Tumors; Burkitt Lymphoma; Carcinoid Tumor (Gastrointestinal); Childhood Carcinoid Tumors; Cardiac (Heart) Tumors; Central Nervous System cancer; Atypical Teratoid/Rhabdoid Tumor, Childhood (Brain Cancer); Embryonal Tumors, Childhood (Brain Cancer); Germ Cell Tumor, Childhood (Brain Cancer); Primary CNS Lymphoma; Cervical Cancer; Cholangiocarcinoma; Bile Duct Cancer Chordoma; Chronic Lymphocytic Leukemia (CLL); Chronic Myelogenous Leukemia (CML); Chronic Myeloproliferative Neoplasms; Colorectal Cancer; Craniopharyngioma (Brain Cancer); Cutaneous T-Cell; Ductal Carcinoma In Situ (DCIS); Embryonal Tumors, Central Nervous System, Childhood (Brain Cancer); Endometrial Cancer (Uterine Cancer); Ependymoma, Childhood (Brain Cancer); Esophageal Cancer; Esthesioneuroblastoma; Ewing Sarcoma (Bone Cancer); Extracranial Germ Cell Tumor; Extragonadal Germ Cell Tumor; Eye Cancer; Intraocular Melanoma; Intraocular Melanoma; Retinoblastoma; Fallopian Tube Cancer; Fibrous Histiocytoma of Bone, Malignant, or Osteosarcoma; Gallbladder Cancer; Gastric (Stomach) Cancer; Gastrointestinal Carcinoid Tumor; Gastrointestinal Stromal Tumors (GIST) (Soft Tissue Sarcoma); Germ Cell Tumors; Central Nervous System Germ Cell Tumors (Brain Cancer); Childhood Extracranial Germ Cell Tumors; Extragonadal Germ Cell Tumors; Ovarian Germ Cell Tumors; Testicular Cancer; Gestational Trophoblastic Disease; Hairy Cell Leukemia; Head and Neck Cancer; Heart Tumors; Hepatocellular (Liver) Cancer; Histiocytosis, Langerhans Cell; Hodgkin Lymphoma; Hypopharyngeal Cancer; Intraocular Melanoma; Islet Cell Tumors; Pancreatic Neuroendocrine Tumors; Kaposi Sarcoma (Soft Tissue Sarcoma); Kidney (Renal Cell) Cancer; Langerhans Cell Histiocytosis; Laryngeal Cancer; Leukemia; Lip and Oral Cavity Cancer; Liver Cancer; Lung Cancer (Non-Small Cell and Small Cell); Lymphoma; Male Breast Cancer; Malignant Fibrous Histiocytoma of Bone or Osteosarcoma; Melanoma; Melanoma, Intraocular (Eye); Merkel Cell Carcinoma (Skin Cancer); Mesothelioma, Malignant; Metastatic Cancer; Metastatic Squamous Neck Cancer with Occult Primary; Midline Tract Carcinoma Involving NUT Gene; Mouth Cancer; Multiple Endocrine Neoplasia Syndromes; Multiple Myeloma/Plasma Cell Neoplasms; Mycosis Fungoides (Lymphoma); Myelodysplastic Syndromes, Myelodysplastic/Myeloproliferative Neoplasms; Myelogenous Leukemia, Chronic (CML); Myeloid Leukemia, Acute (AML); Myeloproliferative Neoplasms; Nasal Cavity and Paranasal Sinus Cancer; Nasopharyngeal Cancer; Neuroblastoma; Non-Hodgkin Lymphoma; Non-Small Cell Lung Cancer; Oral Cancer, Lip or Oral Cavity Cancer; Oropharyngeal Cancer; Osteosarcoma and Malignant Fibrous Histiocytoma of Bone; Ovarian Cancer Pancreatic Cancer; Pancreatic Neuroendocrine Tumors (Islet Cell Tumors); Papillomatosis; Paraganglioma; Paranasal Sinus and Nasal Cavity Cancer; Parathyroid Cancer; Penile Cancer; Pharyngeal Cancer; Pheochromocytoma; Pituitary Tumor; Plasma Cell Neoplasm/Multiple Myeloma; Pleuropulmonary Blastoma; Pregnancy and Breast Cancer; Primary Central Nervous System (CNS) Lymphoma; Primary Peritoneal Cancer; Prostate Cancer; Rectal Cancer; Recurrent Cancer Renal Cell (Kidney) Cancer; Retinoblastoma; Rhabdomyosarcoma, Childhood (Soft Tissue Sarcoma); Salivary Gland Cancer; Sarcoma; Childhood Rhabdomyosarcoma (Soft Tissue Sarcoma); Childhood Vascular Tumors (Soft Tissue Sarcoma); Ewing Sarcoma (Bone Cancer); Kaposi Sarcoma (Soft Tissue Sarcoma); Osteosarcoma (Bone Cancer); Uterine Sarcoma; Sezary Syndrome (Lymphoma); Skin Cancer; Small Cell Lung Cancer; Small Intestine Cancer; Soft Tissue Sarcoma; Squamous Cell Carcinoma of the Skin; Squamous Neck Cancer with Occult Primary, Metastatic; Stomach (Gastric) Cancer; T-Cell Lymphoma, Cutaneous; Lymphoma; Mycosis Fungoides and Sezary Syndrome; Testicular Cancer; Throat Cancer; Nasopharyngeal Cancer; Oropharyngeal Cancer; Hypopharyngeal Cancer; Thymoma and Thymic Carcinoma; Thyroid Cancer; Thyroid Tumors; Transitional Cell Cancer of the Renal Pelvis and Ureter (Kidney (Renal Cell) Cancer); Ureter and Renal Pelvis; Transitional Cell Cancer (Kidney (Renal Cell) Cancer; Urethral Cancer; Uterine Cancer, Endometrial; Uterine Sarcoma; Vaginal Cancer; Vascular Tumors (Soft Tissue Sarcoma); Vulvar Cancer; or Wilms Tumor.

RNAs Associated with Metastasis (RAMS) (e.g., RAMS11) Modulation Agents

As described herein, RAMS expression has been implicated in various cancers and metastatic cancers. As such, modulation of RAMS (e.g., inhibiting RAMS directly, inhibiting RAMS expression, knocking down RAMS, transiently silencing RAMS that are upregulated and associated with cancer and metastasis, such as RAMS11 and others in TABLE 1 or upregulating/increasing expression, activity, or signaling of RAMS that are downregulated and associated with cancer and metastasis, such as RAMS78-RAMS148) can be used for treatment of such conditions. A RAMS modulation agent can modulate or inhibit RAMS directly, inhibit RAMS expression, knock down RAMS, or transiently silence RAMS.

As an example, inhibiting RAMS11 using directly locked nucleic acids (LNAs) can be used as a targeted therapy (see e.g., Ma, L. 2016 MicroRNA and Metastasis, *Advances in Cancer Research* 132 165-207). Except as otherwise noted herein, therefore, the process of the present disclosure can be carried out in accordance with such processes.

RAMS modulating agents can be any composition or method that can modulate RAMS expression on cells. For example, a RAMS modulation agent can be an activator, an inhibitor, an agonist, or an antagonist. As another example, the RAMS modulation can be the result of gene editing.

A RAMS modulation agent can be an antibody (e.g., a monoclonal antibody to RAMS).

RNAs Associated with Metastasis (RAMS) (e.g., RAMS11) Signal Reduction, Elimination, or Inhibition by Small Molecule Inhibitors, RNA Interference, or ASOs As described herein, a RAMS modulating agent can be used for cancer therapy. A RAMS modulation agent can be used to reduce/eliminate or enhance/increase RAMS signals. For example, a RAMS modulation agent can be a small molecule inhibitor of RAMS. As another example, a RAMS modulation agent can be a short hairpin RNA (shRNA). As another example, a RAMS modulation agent can be a short interfering RNA (siRNA). As another example, a RAMS modulation agent can be a single guide RNA (sgRNA). As another example, a RAMS modulation agent can be a micro RNA (miRNA).

As another example, long noncoding RNA (lncRNA), such as RAMS, can be targeted or silenced with antisense oligonucleotides (ASOs) as a cancer therapeutics. Processes for making ASOs targeted to RNAs are well known, see e.g., Zhou et al. 2016 *Methods Mol Biol.* 1402:199-213. Except as otherwise noted herein, therefore, the process of the present disclosure can be carried out in accordance with such processes.

As an example, Exiqon's locked nucleic acid (LNA) GapmeRs antisense oligonucleotides (ASOs) can be used. They contain a central stretch (gap) of monomers flanked by blocks of LNA modified nucleotides that (i) increase the target affinity and nuclease resistance of the oligo and (ii) the gap activates RNase H cleavage of the target RNA upon binding. The LNA™ oligonucleotides can be designed for any region of the target RNA sequence. In addition, the design flexibility afforded by LNA™ means that it is possible to design multiple LNA™ antisense oligonucleotides to the same target sequence, which serve as useful experimental controls (see e.g., *Exiquon In vivo Guidelines*, v. 1.0, 35 pages).

Genome Editing

As described herein, RAMS signals can be modulated (e.g., reduced, eliminated, silenced, activated, downregulated, upregulated) using genome editing. Processes for genome editing are well known, see e.g. Aldi 2018 *Nature Communications* 9(1911). Except as otherwise noted herein, therefore, the process of the present disclosure can be carried out in accordance with such processes.

For example, genome editing can comprise CRISPR/Cas9, CRISPR-Cpf1, TALEN, or ZNFs. Adequate blockage of RAMS by genome editing can result in protection against treatment or drug resistance. Other RAMS identified (see e.g., TABLE 1) are down-regulated and can be re-introduced into a cell to treat the patient.

As an example, clustered regularly interspaced short palindromic repeats (CRISPR)/CRISPR-associated (Cas) systems are a new class of genome-editing tools that target desired genomic sites in mammalian cells. Recently published type II CRISPR/Cas systems use Cas9 nuclease that is targeted to a genomic site by complexing with a synthetic guide RNA that hybridizes to a 20-nucleotide DNA sequence and immediately preceding an NGG motif recognized by Cas9 (thus, a $(N)_{20}$NGG target DNA sequence). This results in a double-strand break three nucleotides upstream of the NGG motif. The double strand break instigates either non-homologous end-joining, which is error-prone and conducive to frameshift mutations that knock out gene alleles, or homology-directed repair, which can be exploited with the use of an exogenously introduced double-strand or single-strand DNA repair template to knock in or correct a mutation in the genome. Thus, genomic editing, for example, using CRISPR/Cas systems could be useful tools for therapeutic applications for the removal or addition of RAMS signals or expression. The CRISPR-Cas9 system can be adapted to generate technologies called CRISPRi (CRISPR interference) and CRISPRa (CRISPR activation). These utilize nuclease-deactivated Cas9 (dCas9) that cannot generate a double-stranded break (DSB), but instead target genomic regions resulting in RNA-directed transcriptional control. CRISPRi can utilize dCas9 with or without a KRAB effector domain that complexes with gRNA to target promoter regions for transcriptional repression, or knockdown, of the gene. CRISPRa can employ dCas9 fused to different transcriptional activation domains, which can be directed to promoter regions by either standard *S. pyogenes* gRNA or special gRNAs that recruit additional transcriptional activation domains to upregulate expression of the target gene.

For example, the methods as described herein can comprise a method for altering a target polynucleotide sequence in a cell comprising contacting the polynucleotide sequence with a clustered regularly interspaced short palindromic repeats-associated (Cas) protein.

RAMS Modulating Agents and RAMS Inhibiting Agents

As described herein, RAMS expression has been implicated in various diseases, disorders, and conditions, such as proliferative conditions such as cancer. As such, modulation of RAMS expression, signaling, activity, or function can be used for treatment of such conditions. A RAMS modulation agent can induce, enhance, or activate RAMS expression, signaling, activity, or function. A RAMS modulation agent can block, knock out, inhibit, reduce, or silence RAMS expression, signaling, activity, or function. RAMS modulation can comprise modulating the expression of RAMS on cells, modulating the quantity of cells that express RAMS, or modulating the quality of the RAMS expressing cells.

RAMS modulation agents can be any composition or method that can modulate RAMS expression on cells. For example, a RAMS modulation agent can be an activator, an inhibitor, an agonist, or an antagonist. As another example, the RAMS modulation can be the result of gene editing.

A RAMS modulation agent can be a RAMS antibody (e.g., a monoclonal antibody to RAMS).

As described herein, a RAMS modulating agent can be a RAMS inhibiting agent. For example, the present disclosure provides for inhibition of RAMS that are upregulated and associated with cancer and metastases, such as RAMS11. An example of a RAMS inhibiting agent can be an agent that inhibits or reduces RAMS11 signaling, expression, function, or activity. As described herein, the present disclosure provides for methods of treating cancer based on the discovery that increased expression of RAMS11 increased the likelihood of drug resistance and metastasis. As shown herein, RAMS11 can be inhibited, but other RAMS identified that are upregulated and associated with good or bad outcomes can be modulated or RAMS that are downregulated and not associated with a bod outcome can be re-introduced into a cell to treat the patient (see e.g., TABLE 1). For example, other upregulated RAMS associated with bad outcomes can be beneficial to inhibit (e.g., RAMS16, RAMS22, RAMS35, RAMS39, RAMS46, RAMS50, RAMS71, RAMS74). As another example, other upregulated RAMS that are associated with good outcomes can be upregulated/enhanced (e.g., RAMS17, RAMS18, RAMS26, RAMS62, RAMS64). Furthermore, some of the other RAMS that were identified are downregulated and can be re-introduced into a cell to treat the patient (e.g., RAMS 78-148).

As described herein, inhibiting upregulated RAMS associated with bad outcomes (e.g., RAMS11) increased drug sensitivity and reduced invasiveness. A RAMS inhibiting agent can be any agent that can silence RAMS, inhibit RAMS, downregulate RAMS, or knocks down RAMS.

As an example, a RAMS inhibiting agent can inhibit RAMS signaling. As another example, a RAMS inhibiting agent can be a short hairpin RNA (shRNA), a short interfering RNA (siRNA), a single guide RNA (sgRNA), or a micro RNA (miRNA) targeting RAMS. As another example, inhibiting RAMS can be performed by silencing or genetically deleting at least one RAMS exon (or functional fragment, portion, or variant thereof) in a subject to reduce or prevent function, expression, activity, or signaling of RAMS, such as through the use of siRNAs, ASOs, CRISPR-Cas9, or analogous technologies, wherein, such modification silences, reduces, or prevents RAMS function, signaling, activity, or expression.

Detection Methods

Levels (e.g., expression, activity, function, etc.) of RAMS can be detected my any known method to detect lncRNAs (see e.g., Moranova et al. *Long Non-Coding RNAs—Current Methods of Detection and Clinical Applications Klin Onkol Fall* 2019; 32(Supplementum 3):65-71.

Long non-coding RNAs (lncRNA) can be more than 200-nucleotide-long RNA molecules that affect multiple physiologic phenomena and have important regulatory functions in cells. Their levels are often altered in various malignancies, thus they represent a potential biomarker for the diagnostics, prognosis, or recurrence of cancer.

Numerous methods can be used for the analysis or detection of lncRNA. For example, detecting lncRNA using optical methods used for the detection of messenger RNAs, polymerase chain reaction with reverse transcription, fluorescence in situ hybridization, or next-generation sequencing. Other techniques for lncRNA detection can be used such as chemiluminescent and electrochemical techniques.

There is only one single approved lncRNA-based diagnostic test, a PCA3 test for the diagnosis of prostate cancer from a patient's urine. All other tests are only in their research phase and need to be validated. As such, lncRNA testing is a non-routine, unconventional activity.

As another example, fluorescence in situ hybridization (FISH) is a molecular cytogenetic technique that uses fluorescent probes that bind to only those parts of a nucleic acid sequence with a high degree of sequence complementarity. It can detect and localize the presence or absence of specific DNA sequences on chromosomes. Fluorescence microscopy can be used to find out where the fluorescent probe is bound to the chromosomes. FISH is often used for finding specific features in DNA for use in genetic counseling, medicine, and species identification. FISH can also be used to detect and localize specific RNA targets (mRNA, lncRNA and miRNA) in cells, circulating tumor cells, and tissue samples. In this context, it can help define the spatial-temporal patterns of gene expression within cells and tissues.

Probes

Generally, in biology, a probe is a single strand of DNA or RNA that is complementary to a nucleotide sequence of interest. RNA probes can be designed for any gene or any sequence within a gene for visualization of mRNA, lncRNA, and miRNA in tissues and cells. FISH is used by examining the cellular reproduction cycle, specifically interphase of the nuclei for any chromosomal abnormalities. FISH allows the analysis of a large series of archival cases much easier to identify the pinpointed chromosome by creating a probe with an artificial chromosomal foundation that will attract similar chromosomes. The hybridization signals for each probe when a nucleic abnormality is detected. Each probe for the detection of mRNA and lncRNA is composed of ~20-50 oligonucleotide pairs, each pair covering a space of 40-50 bp. The specifics depend on the specific FISH technique used. Probes are often derived from fragments of DNA that were isolated, purified, and amplified.

Preparation and Hybridization Process—RNA

Cells, circulating tumor cells (CTCs), or formalin-fixed paraffin-embedded (FFPE) or frozen tissue sections can be fixed, then permeabilized to allow target accessibility. FISH can also be successfully done on unfixed cells. Generally, a target-specific probe, composed of 20 oligonucleotide pairs, hybridizes to the target RNA(s). Separate but compatible signal amplification systems enable the multiplex assay (up to two targets per assay). Signal amplification is achieved via series of sequential hybridization steps. At the end of the assay the tissue samples are visualized under a fluorescence microscope.

Molecular Engineering

The following definitions and methods are provided to better define the present invention and to guide those of ordinary skill in the art in the practice of the present invention. Unless otherwise noted, terms are to be understood according to conventional usage by those of ordinary skill in the relevant art.

The terms "heterologous DNA sequence", "exogenous DNA segment", or "heterologous nucleic acid," as used herein, each refers to a sequence that originates from a source foreign to the particular host cell or, if from the same source, is modified from its original form. Thus, a heterologous gene in a host cell includes a gene that is endogenous to the particular host cell but has been modified through, for example, the use of DNA shuffling or cloning. The terms also include non-naturally occurring multiple copies of a naturally occurring DNA sequence. Thus, the terms refer to a DNA segment that is foreign or heterologous to the cell, or homologous to the cell but in a position within the host cell nucleic acid in which the element is not ordinarily found. Exogenous DNA segments are expressed to yield exogenous polypeptides. A "homologous" DNA sequence is a DNA sequence that is naturally associated with a host cell into which it is introduced.

Expression vector, expression construct, plasmid, or recombinant DNA construct is generally understood to refer to a nucleic acid that has been generated via human intervention, including by recombinant means or direct chemical synthesis, with a series of specified nucleic acid elements that permit transcription or translation of a particular nucleic acid in, for example, a host cell. The expression vector can be part of a plasmid, virus, or nucleic acid fragment. Typically, the expression vector can include a nucleic acid to be transcribed operably linked to a promoter.

A "promoter" is generally understood as a nucleic acid control sequence that directs transcription of a nucleic acid. An inducible promoter is generally understood as a promoter that mediates transcription of an operably linked gene in response to a particular stimulus. A promoter can include necessary nucleic acid sequences near the start site of transcription, such as, in the case of a polymerase II type promoter, a TATA element. A promoter can optionally include distal enhancer or repressor elements, which can be located as much as several thousand base pairs from the start site of transcription.

A "transcribable nucleic acid molecule" as used herein refers to any nucleic acid molecule capable of being transcribed into an RNA molecule. Methods are known for introducing constructs into a cell in such a manner that the transcribable nucleic acid molecule is transcribed into a functional mRNA molecule that is translated and therefore expressed as a protein product. Constructs may also be constructed to be capable of expressing antisense RNA molecules, in order to inhibit translation of a specific RNA molecule of interest. For the practice of the present disclosure, conventional compositions and methods for preparing and using constructs and host cells are well known to one skilled in the art (see e.g., Sambrook and Russel (2006) *Condensed Protocols from Molecular Cloning: A Laboratory Manual*, Cold Spring Harbor Laboratory Press, ISBN-10: 0879697717; Ausubel et al. (2002) *Short Protocols in Molecular Biology*, 5th ed., *Current Protocols*, ISBN-10: 0471250929; Sambrook and Russel (2001) *Molecular Cloning: A Laboratory Manual*, 3d ed., Cold Spring Harbor Laboratory Press, ISBN-10: 0879695773; Elhai, J. and Wolk, C. P. 1988. *Methods in Enzymology* 167, 747-754).

The "transcription start site" or "initiation site" is the position surrounding the first nucleotide that is part of the transcribed sequence, which is also defined as position +1. With respect to this site, all other sequences of the gene and its controlling regions can be numbered. Downstream sequences (i.e., further protein encoding sequences in the 3' direction) can be denominated positive, while upstream sequences (mostly of the controlling regions in the 5' direction) are denominated negative.

"Operably-linked" or "functionally linked" refers preferably to the association of nucleic acid sequences on a single nucleic acid fragment so that the function of one is affected by the other. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation. The two nucleic acid molecules may be part of a single contiguous nucleic acid molecule and may be adjacent. For example, a promoter is operably linked to a gene of interest if the promoter regulates or mediates transcription of the gene of interest in a cell.

A "construct" is generally understood as any recombinant nucleic acid molecule such as a plasmid, cosmid, virus, autonomously replicating nucleic acid molecule, phage, or linear or circular single-stranded or double-stranded DNA or RNA nucleic acid molecule, derived from any source, capable of genomic integration or autonomous replication, comprising a nucleic acid molecule where one or more nucleic acid molecule has been operably linked.

A construct of the present disclosure can contain a promoter operably linked to a transcribable nucleic acid molecule operably linked to a 3' transcription termination nucleic acid molecule. In addition, constructs can include but are not limited to additional regulatory nucleic acid molecules from, e.g., the 3'-untranslated region (3' UTR). Constructs can include but are not limited to the 5' untranslated regions (5' UTR) of an mRNA nucleic acid molecule which can play an important role in translation initiation and can also be a genetic component in an expression construct. These additional upstream and downstream regulatory nucleic acid molecules may be derived from a source that is native or heterologous with respect to the other elements present on the promoter construct.

The term "transformation" refers to the transfer of a nucleic acid fragment into the genome of a host cell, resulting in genetically stable inheritance. Host cells containing the transformed nucleic acid fragments are referred to as "transgenic" cells, and organisms comprising transgenic cells are referred to as "transgenic organisms".

"Transformed," "transgenic," and "recombinant" refer to a host cell or organism such as a bacterium, cyanobacterium, animal, or a plant into which a heterologous nucleic acid molecule has been introduced. The nucleic acid molecule can be stably integrated into the genome as generally known in the art and disclosed (Sambrook 1989; Innis 1995; Gelfand 1995; Innis & Gelfand 1999). Known methods of PCR include, but are not limited to, methods using paired primers, nested primers, single specific primers, degenerate primers, gene-specific primers, vector-specific primers, partially mismatched primers, and the like. The term "untransformed" refers to normal cells that have not been through the transformation process.

"Wild-type" refers to a virus or organism found in nature without any known mutation.

Design, generation, and testing of the variant nucleotides, and their encoded polypeptides, having the above-required percent identities and retaining a required activity of the expressed protein is within the skill of the art. For example, directed evolution and rapid isolation of mutants can be according to methods described in references including, but not limited to, Link et al. (2007) *Nature Reviews* 5(9), 680-688; Sanger et al. (1991) *Gene* 97(1), 119-123; Ghadessy et al. (2001) *Proc Natl Acad Sci USA* 98(8) 4552-4557. Thus, one skilled in the art could generate a large number of nucleotide and/or polypeptide variants having, for example, at least 95-99% identity to the reference sequence described herein and screen such for desired phenotypes according to methods routine in the art.

Nucleotide and/or amino acid sequence identity percent (%) is understood as the percentage of nucleotide or amino acid residues that are identical with nucleotide or amino acid residues in a candidate sequence in comparison to a reference sequence when the two sequences are aligned. To determine percent identity, sequences are aligned and if necessary, gaps are introduced to achieve the maximum percent sequence identity. Sequence alignment procedures to determine percent identity are well known to those of skill in the art. Often publicly available computer software such as BLAST, BLAST2, ALIGN2, or Megalign (DNASTAR) software is used to align sequences. Those skilled in the art can determine appropriate parameters for measuring alignment, including any algorithms needed to achieve maximal alignment over the full-length of the sequences being compared. When sequences are aligned, the percent sequence identity of a given sequence A to, with, or against a given sequence B (which can alternatively be phrased as a given sequence A that has or comprises a certain percent sequence identity to, with, or against a given sequence B) can be calculated as: percent sequence identity=X/Y100, where X is the number of residues scored as identical matches by the sequence alignment program's or algorithm's alignment of A and B and Y is the total number of residues in B. If the length of sequence A is not equal to the length of sequence B, the percent sequence identity of A to B will not equal the percent sequence identity of B to A. For example, the percent identity can be at least 80% or about 80%; about 81%; about 82%; about 83%; about 84%; about 85%; about 86%; about 87%; about 88%; about 89%; about 90%; about 91%; about 92%; about 93%; about 94%; about 95%; about 96%; about 97%; about 98%; about 99%; or about 100%.

Substitution refers to the replacement of one amino acid with another amino acid in a protein or the replacement of one nucleotide with another in DNA or RNA. Insertion refers to the insertion of one or more amino acids in a protein or the insertion of one or more nucleotides with another in DNA or RNA. Deletion refers to the deletion of one or more amino acids in a protein or the deletion of one or more nucleotides with another in DNA or RNA. Generally, substitutions, insertions, or deletions can be made at any position so long as the required activity is retained.

So-called conservative exchanges can be carried out in which the amino acid which is replaced has a similar property as the original amino acid, for example, the exchange of Glu by Asp, Gln by Asn, Val by lie, Leu by lie, and Ser by Thr. For example, amino acids with similar properties can be Aliphatic amino acids (e.g., Glycine, Alanine, Valine, Leucine, Isoleucine); hydroxyl or sulfur/selenium-containing amino acids (e.g., Serine, Cysteine, Selenocysteine, Threonine, Methionine); Cyclic amino acids (e.g., Proline); Aromatic amino acids (e.g., Phenylalanine, Tyrosine, Tryptophan); Basic amino acids (e.g., Histidine, Lysine, Arginine); or Acidic and their Amide (e.g., Aspartate, Glutamate, Asparagine, Glutamine). Deletion is the replacement of an amino acid by a direct bond. Positions for deletions include the termini of a polypeptide and linkages between individual protein domains. Insertions are introductions of amino acids into the polypeptide chain, a direct bond formally being replaced by one or more amino acids. An amino acid sequence can be modulated with the help of art-known computer simulation programs that can produce a polypeptide with, for example, improved activity or altered regulation. On the basis of these artificially generated polypeptide sequences, a corresponding nucleic acid molecule coding for such a modulated polypeptide can be synthesized in-vitro using the specific codon-usage of the desired host cell.

"Highly stringent hybridization conditions" are defined as hybridization at 65° C. in a 6×SSC buffer (i.e., 0.9 M sodium chloride and 0.09 M sodium citrate). Given these conditions, a determination can be made as to whether a given set of sequences will hybridize by calculating the melting temperature ($T_m$) of a DNA duplex between the two sequences. If a particular duplex has a melting temperature lower than 65° C. in the salt conditions of a 6×SSC, then the two sequences will not hybridize. On the other hand, if the melting temperature is above 65° C. in the same salt conditions, then the sequences will hybridize. In general, the melting temperature for any hybridized DNA:DNA sequence can be determined using the following formula: $T_m$=81.5° C.+16.6($\log_{10}$[Na$^+$])+0.41(fraction G/C content)−0.63(% formamide)−(600/l). Furthermore, the $T_m$ of a DNA:DNA hybrid is decreased by 1-1.5° C. for every 1% decrease in nucleotide identity (see e.g., Sambrook and Russel, 2006).

Host cells can be transformed using a variety of standard techniques known to the art (see e.g., Sambrook and Russel (2006) *Condensed Protocols from Molecular Cloning: A Laboratory Manual*, Cold Spring Harbor Laboratory Press, ISBN-10: 0879697717; Ausubel et al. (2002) *Short Protocols in Molecular Biology*, 5th ed., Current Protocols, ISBN-10: 0471250929; Sambrook and Russel (2001) *Molecular Cloning: A Laboratory Manual*, 3d ed., Cold Spring Harbor Laboratory Press, ISBN-10: 0879695773; Elhai, J. and Wolk, C. P. 1988. *Methods in Enzymology* 167, 747-754). Such techniques include, but are not limited to, viral infection, calcium phosphate transfection, liposome-mediated transfection, microprojectile-mediated delivery, receptor-mediated uptake, cell fusion, electroporation, and the like. The transfected cells can be selected and propagated to provide recombinant host cells that comprise the expression vector stably integrated in the host cell genome.

Exemplary nucleic acids that may be introduced to a host cell include, for example, DNA sequences or genes from another species, or even genes or sequences which originate with or are present in the same species, but are incorporated into recipient cells by genetic engineering methods. The term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA that is already present in the cell, DNA from another individual of the same type of organism, DNA from a different organism, or a DNA generated externally, such as a DNA sequence containing an antisense message of a gene, or a DNA sequence encoding a synthetic or modified version of a gene.

Host strains developed according to the approaches described herein can be evaluated by a number of means known in the art (see e.g., Studier (2005) *Protein Expr Purif.* 41(1), 207-234; Gellissen, ed. (2005) *Production of Recombinant Proteins: Novel Microbial and Eukaryotic Expression Systems*, Wiley-VCH, ISBN-10: 3527310363; Baneyx (2004) Protein Expression Technologies, Taylor & Francis, ISBN-10: 0954523253).

Methods of down-regulation or silencing genes are known in the art. For example, expressed protein activity can be down-regulated or eliminated using antisense oligonucleotides (ASOs), protein aptamers, nucleotide aptamers, and RNA interference (RNAi) (e.g., small interfering RNAs (siRNA), short hairpin RNA (shRNA), and micro RNAs (miRNA) (see e.g., Rinaldi and Wood (2017) *Nature Reviews Neurology* 14, describing ASO therapies; Fanning and Symonds (2006) *Handb Exp Pharmacol.* 173, 289-303G, describing hammerhead ribozymes and small hairpin RNA; Helene, et al. (1992) *Ann. N.Y. Acad. Sci.* 660, 27-36; Maher (1992) *Bioassays* 14(12): 807-15, describing targeting deoxyribonucleotide sequences; Lee et al. (2006) *Curr Opin Chem Biol.* 10, 1-8, describing aptamers; Reynolds et al. (2004) *Nature Biotechnology* 22(3), 326-330, describing RNAi; Pushparaj and Melendez (2006) *Clinical and Experimental Pharmacology and Physiology* 33(5-6), 504-510, describing RNAi; Dillon et al. (2005) *Annual Review of Physiology* 67, 147-173, describing RNAi; Dykxhoorn and Lieberman (2005) *Annual Review of Medicine* 56, 401-423, describing RNAi). RNAi molecules are commercially available from a variety of sources (e.g., Ambion, TX; Sigma Aldrich, MO; Invitrogen). Several siRNA molecule design programs using a variety of algorithms are known to the art (see e.g., Cenix algorithm, Ambion; BLOCK-iT™ RNAi Designer, Invitrogen; siRNA Whitehead Institute Design Tools, Bioinformatics & Research Computing). Traits influential in defining optimal siRNA sequences include G/C content at the termini of the siRNAs, $T_m$ of specific internal domains of the siRNA, siRNA length, position of the target sequence within the CDS (coding region), and nucleotide content of the 3' overhangs.

Formulation

The agents and compositions described herein can be formulated by any conventional manner using one or more pharmaceutically acceptable carriers or excipients as described in, for example, *Remington's Pharmaceutical Sciences* (A. R. Gennaro, Ed.), 21st edition, ISBN: 0781746736 (2005), incorporated herein by reference in its entirety. Such formulations will contain a therapeutically effective amount of a biologically active agent described herein, which can be in purified form, together with a suitable amount of carrier so as to provide the form for proper administration to the subject.

The term "formulation" refers to preparing a drug in a form suitable for administration to a subject, such as a human. Thus, a "formulation" can include pharmaceutically acceptable excipients, including diluents or carriers.

The term "pharmaceutically acceptable" as used herein can describe substances or components that do not cause unacceptable losses of pharmacological activity or unacceptable adverse side effects. Examples of pharmaceutically acceptable ingredients can be those having monographs in United States Pharmacopeia (USP 29) and National Formulary (NF 24), United States Pharmacopeial Convention, Inc, Rockville, Maryland, 2005 ("USP/NF"), or a more recent edition, and the components listed in the continuously updated Inactive Ingredient Search online database of the FDA. Other useful components that are not described in the USP/NF, etc. may also be used.

The term "pharmaceutically acceptable excipient," as used herein, can include any and all solvents, dispersion media, coatings, antibacterial and antifungal agents, isotonic, or absorption delaying agents. The use of such media and agents for pharmaceutically active substances is well known in the art (see generally *Remington's Pharmaceutical Sciences* (A. R. Gennaro, Ed.), 21st edition, ISBN: 0781746736 (2005)). Except insofar as any conventional media or agent is incompatible with an active ingredient, its use in the therapeutic compositions is contemplated. Supplementary active ingredients can also be incorporated into the compositions.

A "stable" formulation or composition can refer to a composition having sufficient stability to allow storage at a convenient temperature, such as between about 0° C. and about 60° C., for a commercially reasonable period of time, such as at least about one day, at least about one week, at least about one month, at least about three months, at least about six months, at least about one year, or at least about two years.

The formulation should suit the mode of administration. The agents of use with the current disclosure can be formulated by known methods for administration to a subject using several routes which include, but are not limited to, parenteral, pulmonary, oral, topical, intradermal, intratumoral, intranasal, inhalation (e.g., in an aerosol), implanted, intramuscular, intraperitoneal, intravenous, intrathecal, intracranial, intracerebroventricular, subcutaneous, intranasal, epidural, intrathecal, ophthalmic, transdermal, buccal, and rectal. The individual agents may also be administered in combination with one or more additional agents or together with other biologically active or biologically inert agents. Such biologically active or inert agents may be in fluid or mechanical communication with the agent(s) or attached to the agent(s) by ionic, covalent, Van der Waals, hydrophobic, hydrophilic, or other physical forces.

Controlled-release (or sustained-release) preparations may be formulated to extend the activity of the agent(s) and reduce dosage frequency. Controlled-release preparations can also be used to affect the time of onset of action or other characteristics, such as blood levels of the agent, and consequently, affect the occurrence of side effects. Controlled-release preparations may be designed to initially release an amount of an agent(s) that produces the desired therapeutic effect, and gradually and continually release other amounts of the agent to maintain the level of therapeutic effect over an extended period of time. In order to maintain a near-constant level of an agent in the body, the agent can be released from the dosage form at a rate that will replace the amount of agent being metabolized or excreted from the body. The controlled-release of an agent may be stimulated by various inducers, e.g., change in pH, change in temperature, enzymes, water, or other physiological conditions or molecules.

Agents or compositions described herein can also be used in combination with other therapeutic modalities, as described further below. Thus, in addition to the therapies described herein, one may also provide to the subject other therapies known to be efficacious for treatment of the disease, disorder, or condition.

Therapeutic Methods

Also provided is a process of treating cancer (e.g., colorectal cancer (CRC), metastastic colorectal cancer (mCRC)) in a subject in need administration of a therapeutically effective amount of a RAMS modulating agent, so as to reduce RAMS expression, signaling, activity, or function (e.g., RAMS 11) or increase RAMS expression, signaling, activity, or function (e.g., RAMS that are downregulated) or a cancer therapeutic, so as to select the therapeutic with increased sensitivity and reduced resistance. The methods as described herein can also include administration of a cancer therapeutic wherein the cancer is shown to be not resistant to the therapeutic. The cancer or tumor can be shown to be resistant to certain therapies due to the cancer or tumor having upregulation of RAMS. The methods as described herein can also include administration of a cancer therapeutic that has increased sensitivity to cancers or tumors having upregulation of RAMS.

Methods described herein are generally performed on a subject in need thereof. A subject in need of the therapeutic methods described herein can be a subject having, diagnosed with, suspected of having, or at risk for developing cancer. A determination of the need for treatment will typically be assessed by a history and physical exam consistent with the disease or condition at issue. Diagnosis of the various conditions treatable by the methods described herein is within the skill of the art. The subject can be an animal subject, including a mammal, such as horses, cows, dogs, cats, sheep, pigs, mice, rats, monkeys, hamsters, guinea pigs, and chickens, and humans. For example, the subject can be a human subject.

Generally, a safe and effective amount of a RAMS modulating agent or cancer therapeutic is, for example, that amount that would cause the desired therapeutic effect in a subject while minimizing undesired side effects. In various embodiments, an effective amount of a RAMS modulating agent or cancer therapeutic described herein can substantially inhibit the progression or invasiveness of cancer, slow the progress of cancer, or limit the development of cancer.

According to the methods described herein, administration can be parenteral, pulmonary, oral, topical, intradermal, intramuscular, intraperitoneal, intravenous, subcutaneous, intranasal, epidural, ophthalmic, buccal, or rectal administration.

When used in the treatments described herein, a therapeutically effective amount of a RAMS modulating agent or cancer therapeutic can be employed in pure form or, where such forms exist, in pharmaceutically acceptable salt form and with or without a pharmaceutically acceptable excipient. For example, the compounds of the present disclosure can be administered, at a reasonable benefit/risk ratio applicable to any medical treatment, in a sufficient amount to reduce/enhance RAMS signaling, reduce/enhance RAMS expression, or downregulate/upregulate RAMS.

The amount of a composition described herein that can be combined with a pharmaceutically acceptable carrier to produce a single dosage form will vary depending upon the host treated and the particular mode of administration. It will be appreciated by those skilled in the art that the unit content of agent contained in an individual dose of each dosage form need not in itself constitute a therapeutically effective amount, as the necessary therapeutically effective amount could be reached by administration of a number of individual doses.

Toxicity and therapeutic efficacy of compositions described herein can be determined by standard pharmaceutical procedures in cell cultures or experimental animals for determining the $LD_{50}$ (the dose lethal to 50% of the population) and the $ED_{50}$, (the dose therapeutically effective in 50% of the population). The dose ratio between toxic and therapeutic effects is the therapeutic index that can be expressed as the ratio $LD_{50}/ED_{50}$, where larger therapeutic indices are generally understood in the art to be optimal.

Inhibition of agents as described herein can be determined by standard pharmaceutical procedures in assays or cell cultures for determining the $IC_{50}$. The half maximal inhibitory concentration ($IC_{50}$) is a measure of the potency of a substance in inhibiting a specific biological or biochemical function. The $IC_{50}$ is a quantitative measure that indicates how much of a particular inhibitory substance (e.g., pharmaceutical agent or drug) is needed to inhibit, in vitro, a given biological process or biological component by 50%. The biological component could be an enzyme, cell, cell receptor, or microorganism, for example. $IC_{50}$ values are typically expressed as molar concentration. $IC_{50}$ is generally used as a measure of antagonist drug potency in pharmacological research. $IC_{50}$ is comparable to other measures of potency, such as $EC_{50}$ for excitatory drugs. $EC_{50}$ represents the dose or plasma concentration required for obtaining 50% of a maximum effect in vivo. $IC_{50}$ can be determined with functional assays or with competition binding assays.

The specific therapeutically effective dose level for any particular subject will depend upon a variety of factors including the disorder being treated and the severity of the disorder; activity of the specific compound employed; the specific composition employed; the age, body weight, general health, sex and diet of the subject; the time of administration; the route of administration; the rate of excretion of the composition employed; the duration of the treatment; drugs used in combination or coincidental with the specific compound employed; and like factors well known in the medical arts (see e.g., Koda-Kimble et al. (2004) *Applied Therapeutics: The Clinical Use of Drugs*, Lippincott Williams & Wilkins, ISBN 0781748453; Winter (2003) *Basic Clinical Pharmacokinetics*, 4*th* ed., Lippincott Williams & Wilkins, ISBN 0781741475; Sharqel (2004) *Applied Biopharmaceutics & Pharmacokinetics*, McGraw-Hill/Appleton & Lange, ISBN 0071375503). For example, it is well within the skill of the art to start doses of the composition at levels lower than those required to achieve the desired therapeutic effect and to gradually increase the dosage until the desired effect is achieved. If desired, the effective daily dose may be divided into multiple doses for purposes of administration. Consequently, single dose compositions may contain such amounts or submultiples thereof to make up the daily dose. It will be understood, however, that the total daily usage of the compounds and compositions of the present disclosure will be decided by an attending physician within the scope of sound medical judgment.

Again, each of the states, diseases, disorders, and conditions, described herein, as well as others, can benefit from compositions and methods described herein. Generally, treating a state, disease, disorder, or condition includes preventing or delaying the appearance of clinical symptoms in a mammal that may be afflicted with or predisposed to the state, disease, disorder, or condition but does not yet experience or display clinical or subclinical symptoms thereof. Treating can also include inhibiting the state, disease, disorder, or condition, e.g., arresting or reducing the development of the disease or at least one clinical or subclinical symptom thereof. Furthermore, treating can include relieving the disease, e.g., causing regression of the state, disease, disorder, or condition or at least one of its clinical or subclinical symptoms. A benefit to a subject to be treated can be either statistically significant or at least perceptible to the subject or to a physician.

Administration of a RAMS modulating or cancer therapeutic agent can occur as a single event or over a time course of treatment. For example, a RAMS modulating agent or cancer therapeutic can be administered daily, weekly, biweekly, or monthly. For treatment of acute conditions, the time course of treatment will usually be at least several days. Certain conditions could extend treatment from several days to several weeks. For example, treatment could extend over one week, two weeks, or three weeks. For more chronic conditions, treatment could extend from several weeks to several months or even a year or more.

Treatment in accord with the methods described herein can be performed prior to, concurrent with, or after conventional treatment modalities for cancer.

A RAMS modulating agent or cancer therapeutic can be administered simultaneously or sequentially with another agent, such as a cancer therapeutic. For example, a RAMS modulating agent or cancer therapeutic can be administered simultaneously with another agent, such as a cancer therapeutic. Simultaneous administration can occur through administration of separate compositions, each containing one or more of a RAMS modulating agent or cancer therapeutic, a cancer therapeutic, or another agent. Simultaneous administration can occur through administration of one composition containing two or more of a RAMS modulating agent or cancer therapeutic, a cancer therapeutic, or another agent. A RAMS modulating agent or cancer therapeutic can be administered sequentially with a cancer therapeutic or another agent. For example, a RAMS modulating agent or cancer therapeutic can be administered before or after administration of a cancer therapeutic or another agent.

Administration

Agents and compositions described herein can be administered according to methods described herein in a variety of means known to the art. The agents and composition can be used therapeutically either as exogenous materials or as endogenous materials. Exogenous agents are those produced or manufactured outside of the body and administered to the body. Endogenous agents are those produced or manufactured inside the body by some type of device (biologic or other) for delivery within or to other organs in the body.

As discussed above, administration can be parenteral, pulmonary, oral, topical, intradermal, intramuscular, intraperitoneal, intravenous, subcutaneous, intranasal, epidural, ophthalmic, buccal, or rectal administration.

Agents and compositions described herein can be administered in a variety of methods well known in the arts. Administration can include, for example, methods involving oral ingestion, direct injection (e.g., systemic or stereotactic), implantation of cells engineered to secrete the factor of interest, drug-releasing biomaterials, polymer matrices, gels, permeable membranes, osmotic systems, multilayer coatings, microparticles, implantable matrix devices, mini-osmotic pumps, implantable pumps, injectable gels and hydrogels, liposomes, micelles (e.g., up to 30 m), nanospheres (e.g., less than 1 m), microspheres (e.g., 1-100 m), reservoir devices, a combination of any of the above, or other suitable delivery vehicles to provide the desired release profile in varying proportions. Other methods of controlled-release delivery of agents or compositions will be known to the skilled artisan and are within the scope of the present disclosure.

Delivery systems may include, for example, an infusion pump which may be used to administer the agent or composition in a manner similar to that used for delivering insulin or chemotherapy to specific organs or tumors. Typically, using such a system, an agent or composition can be administered in combination with a biodegradable, biocompatible polymeric implant that releases the agent over a controlled period of time at a selected site. Examples of polymeric materials include polyanhydrides, polyorthoesters, polyglycolic acid, polylactic acid, polyethylene vinyl acetate, and copolymers and combinations thereof. In addition, a controlled release system can be placed in proximity of a therapeutic target, thus requiring only a fraction of a systemic dosage.

Agents can be encapsulated and administered in a variety of carrier delivery systems. Examples of carrier delivery systems include microspheres, hydrogels, polymeric implants, smart polymeric carriers, and liposomes (see generally, Uchegbu and Schatzlein, eds. (2006) Polymers in Drug Delivery, CRC, ISBN-10: 0849325331). Carrier-based systems for molecular or biomolecular agent delivery can: provide for intracellular delivery; tailor biomolecule/agent release rates; increase the proportion of biomolecule that reaches its site of action; improve the transport of the drug to its site of action; allow colocalized deposition with other agents or excipients; improve the stability of the agent in vivo; prolong the residence time of the agent at its site of action by reducing clearance; decrease the nonspecific delivery of the agent to nontarget tissues; decrease irritation caused by the agent; decrease toxicity due to high initial doses of the agent; alter the immunogenicity of the agent; decrease dosage frequency, improve taste of the product; or improve shelf life of the product.

Screening

Also provided are methods for screening RAMS modulating agents (e.g., RAMS11 inhibiting agents). For example, RAMS expressing cells can be contacted with potential therapeutics and RAMS expression can be measured.

The methods find use in the screening of a variety of different candidate molecules (e.g., potentially therapeutic candidate molecules). Candidate substances for screening according to the methods described herein include, but are not limited to, fractions of tissues or cells, nucleic acids, polypeptides, siRNAs, antisense molecules, aptamers, ribozymes, triple helix compounds, antibodies, and small (e.g., less than about 2000 MW, or less than about 1000 MW, or less than about 800 MW) organic molecules or inorganic molecules including but not limited to salts or metals.

Candidate molecules encompass numerous chemical classes, for example, organic molecules, such as small organic compounds having a molecular weight of more than 50 and less than about 2,500 Daltons. Candidate molecules can comprise functional groups necessary for structural interaction with proteins, particularly hydrogen bonding, and typically include at least an amine, carbonyl, hydroxyl, or carboxyl group, and usually at least two of the functional chemical groups. The candidate molecules can comprise cyclical carbon or heterocyclic structures and/or aromatic or polyaromatic structures substituted with one or more of the above functional groups.

A candidate molecule can be a compound in a library database of compounds. One of skill in the art will be generally familiar with, for example, numerous databases for commercially available compounds for screening (see e.g., ZINC database, UCSF, with 2.7 million compounds over 12 distinct subsets of molecules; Irwin and Shoichet (2005) *J Chem Inf Model* 45, 177-182). One of skill in the art will also be familiar with a variety of search engines to identify commercial sources or desirable compounds and classes of compounds for further testing (see e.g., ZINC database; eMolecules.com; and electronic libraries of commercial compounds provided by vendors, for example, ChemBridge, Princeton BioMolecular, Ambinter SARL, Enamine, ASDI, Life Chemicals, etc.).

Candidate molecules for screening according to the methods described herein include both lead-like compounds and drug-like compounds. A lead-like compound is generally understood to have a relatively smaller scaffold-like structure (e.g., molecular weight of about 150 to about 350 kD) with relatively fewer features (e.g., less than about 3 hydrogen donors and/or less than about 6 hydrogen acceptors; hydrophobicity character xlogP of about −2 to about 4) (see e.g., Angewante (1999) *Chemie Int. ed. Engl.* 24, 3943-3948). In contrast, a drug-like compound is generally understood to have a relatively larger scaffold (e.g., molecular weight of about 150 to about 500 kD) with relatively more numerous features (e.g., less than about 10 hydrogen acceptors and/or less than about 8 rotatable bonds; hydrophobicity character xlogP of less than about 5) (see e.g., Lipinski (2000) *J. Pharm. Tox. Methods* 44, 235-249). Initial screening can be performed with lead-like compounds.

When designing a lead from spatial orientation data, it can be useful to understand that certain molecular structures are characterized as being "drug-like". Such characterization can be based on a set of empirically recognized qualities derived by comparing similarities across the breadth of known drugs within the pharmacopoeia. While it is not required for drugs to meet all, or even any, of these characterizations, it is far more likely for a drug candidate to meet with clinical success if it is drug-like.

Several of these "drug-like" characteristics have been summarized into the four rules of Lipinski (generally known as the "rules of fives" because of the prevalence of the number 5 among them). While these rules generally relate to oral absorption and are used to predict bioavailability of a compound during lead optimization, they can serve as effective guidelines for constructing a lead molecule during rational drug design efforts such as may be accomplished by using the methods of the present disclosure.

The four "rules of five" state that a candidate drug-like compound should have at least three of the following characteristics: (i) a weight less than 500 Daltons; (ii) a log of P less than 5; (iii) no more than 5 hydrogen bond donors (expressed as the sum of OH and NH groups); and (iv) no more than 10 hydrogen bond acceptors (the sum of N and O atoms). Also, drug-like molecules typically have a span (breadth) of between about 8 Å to about 15 Å.

Compositions and methods described herein utilizing molecular biology protocols can be according to a variety of standard techniques known to the art (see, e.g., Sambrook and Russel (2006) *Condensed Protocols from Molecular Cloning: A Laboratory Manual*, Cold Spring Harbor Laboratory Press, ISBN-10: 0879697717; Ausubel et al. (2002) *Short Protocols in Molecular Biology*, 5th ed., Current Protocols, ISBN-10: 0471250929; Sambrook and Russel (2001) *Molecular Cloning: A Laboratory Manual*, 3d ed., Cold Spring Harbor Laboratory Press, ISBN-10: 0879695773; Elhai, J. and Wolk, C. P. 1988. *Methods in Enzymology* 167, 747-754; Studier (2005) *Protein Expr Purif.* 41(1), 207-234; Gellissen, ed. (2005) *Production of Recombinant Proteins: Novel Microbial and Eukaryotic Expression Systems*, Wiley-VCH, ISBN-10: 3527310363; Baneyx (2004) Protein Expression Technologies, Taylor & Francis, ISBN-10: 0954523253).

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

All publications, patents, patent applications, and other references cited in this application are incorporated herein by reference in their entirety for all purposes to the same extent as if each individual publication, patent, patent application, or other reference was specifically and individually indicated to be incorporated by reference in its entirety for all purposes. Citation of a reference herein shall not be construed as an admission that such is prior art to the present disclosure.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples.

EXAMPLES

The following non-limiting examples are provided to further illustrate the present disclosure. It should be appreciated by those of skill in the art that the techniques disclosed in the examples that follow represent approaches the inventors have found function well in the practice of the present disclosure, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the present disclosure.

Example 1: Novel Long Non-Coding RNA as a Colorectal Cancer Diagnostic Marker and Therapeutic Target The following example describes the discovery of RAMS11, which is shown to be elevated in colorectal cancer and shows a more significant elevation in metastatic colorectal cancer (see Appendix I for additional details).

Figure 14:
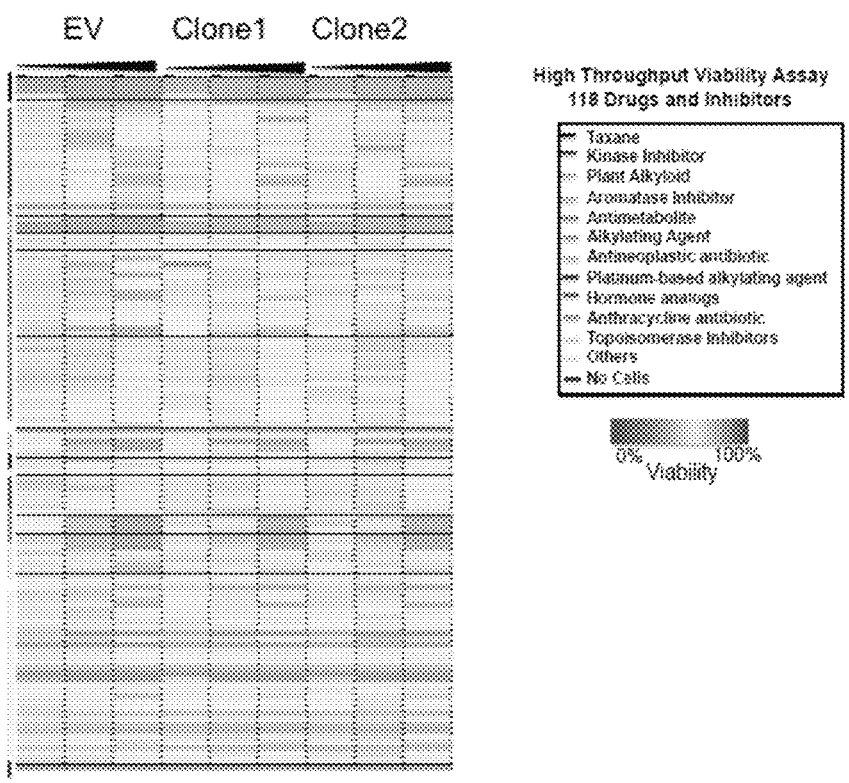
FIG. 14. High Throughput drug viability assays reveal RAMS11 overexpression causes drug resistance. (a) High throughput viability assay on 119 drugs with HT29 RAMS11 overexpressing cells. Gemcitabine (b) and Floxuridine (c) shows significant resistance to RAMS11 overexpression.
Figure 14:
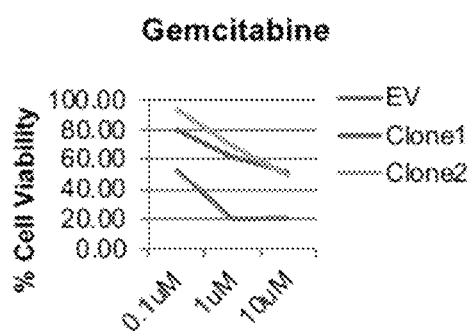
Figure 14:
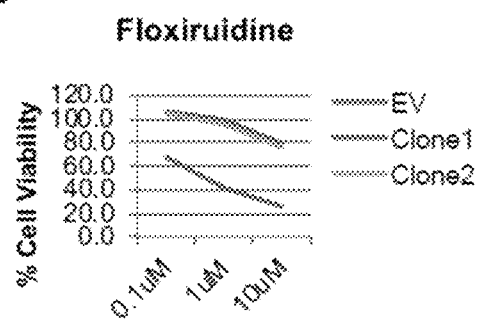
Figure 15:
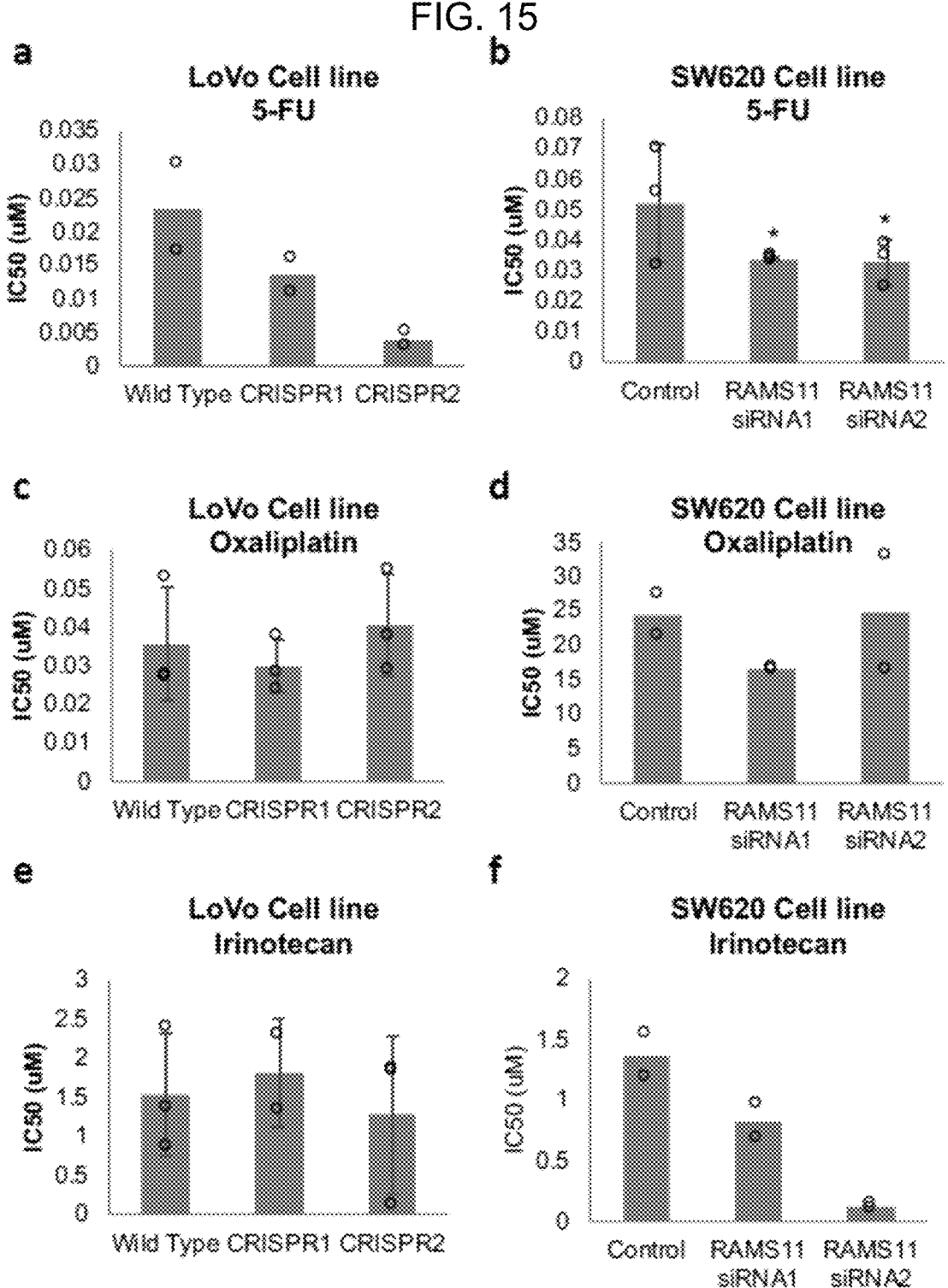
FIG. 15. $IC_{50}$s of clinically used drugs for colorectal cancer treatment. RAMS11 CRISPR KO cell lines and SW620 cells with silenced RAMS11 treated with 5-FU (a and b), Oxaliplatin (c and d), and Irinotecan (e and f) drug treatments. Data is presented as mean values s.d, n=3. Experiments repeated more than two times. *Fold >1.5, **Fold >5.

This Example also described the discovery that the expression of the lncRNA, RAMS11, associates with increased resistance to currently used chemotherapies in colon cancer/colorectal cancer (CRC) (see e.g. FIG. 14 and FIG. 15). As described herein, RAMS11 was shown to be associated with poor disease-free survival and promotion of aggressive phenotypes in vitro and in vivo. An FDA-approved drug high-throughput viability assay revealed that elevated RAMS11 expression increased resistance to topoisomerase inhibitors. Subsequent experiments demonstrated RAMS11-dependent recruitment of Chromobox protein 4 (CBX4) to transcriptionally activate Topoisomerase II alpha (TOP2α). Overall, recent clinical trials using topoisomerase inhibitors coupled with our findings of RAMS11-dependent regulation of TOP2α supports the use of RAMS 11 as a novel biomarker and therapeutic target for mCRC.

Abstract

Colorectal cancer (CRC) is the most common gastrointestinal malignancy in the U.S.A. and approximately 50% of patients develop metastatic disease (mCRC). Despite our understanding of long non-coding RNAs (lncRNAs) in primary colon cancer, their role in mCRC and treatment resistance remains poorly characterized. Therefore, through transcriptome sequencing of normal, primary, and distant mCRC tissues we find 148 differentially expressed RNAs Associated with Metastasis (RAMS). We prioritize RAMS11 due to its association with poor disease-free survival and promotion of aggressive phenotypes in vitro and in vivo. An FDA-approved drug high-throughput viability assay shows that elevated RAMS11 expression increases resistance to topoisomerase inhibitors. Subsequent experiments demonstrate RAMS11-dependent recruitment of Chromobox protein 4 (CBX4) transcriptionally activates Topoisomerase II alpha (TOP2α). Overall, recent clinical trials using topoisomerase inhibitors coupled with our findings of RAMS11-dependent regulation of TOP2α supports the potential use of RAMS11 as a biomarker and therapeutic target for mCRC.

Introduction

Colorectal cancer (CRC) is the most common gastrointestinal malignancy in the United States. At the time of initial diagnosis, 20% of patients present with metastasis, and of those patients with primary disease approximately 50% will eventually develop metastatic disease[1]. Furthermore, the overall 5-year survival rate for patients with metastatic CRC (mCRC) is only 14%[2,3]. Currently, there are numerous therapeutic treatments for patients with mCRC including surgery, cytotoxic chemotherapy, targeted therapy, immunotherapy, radiation, and combination strategies. However, there is little pre-treatment data that can predict response to treatment and development of resistance[4]. While there are promising developments in second-line treatment options for mCRC patients using cytotoxic agents or targeted agents, the mechanisms driving metastatic progression remain poorly characterized thus prohibiting effective drug development. Furthermore, response to second-line treatment is even less effective than first line[5,6]. These statistics and poor treatment options highlight the critical need for improved biomarker-driven therapies at the time of diagnosis.

To date, CRC research has primarily focused on the deregulation of protein-coding genes to identify oncogenes and tumor suppressors as potential diagnostic and therapeutic targets[7,8]. While more recent studies have explored the role of microRNAs in CRC[9,10], there is still a lack of studies focusing on long non-coding RNAs (lncRNAs) in mCRC. LncRNAs are typically greater than 200 nucleotides in length, lack coding potential, are transcribed by RNA polymerase II, spliced, 5' capped, and polyadenylated[11]. LncRNAs are known to have a diverse range of biological functions, including serving as critical regulators in tumorigenesis and metastasis[12-18]. Furthermore, the clinical significance of lncRNAs can be exemplified by their use as diagnostic, prognostic, predictive biomarkers, and potential therapeutic targets[19-24]. Therefore, the characterization of lncRNAs, elucidating their function, and assessing their clinical applicability could significantly impact mCRC diagnosis and treatment.

While transcriptome sequencing has provided an unbiased method for discovering lncRNAs, existing large-scale sequencing projects such as The Cancer Genome Atlas Network (TCGA)[25] are comprised of predominantly primary tumors lacking matched metastatic samples. This represents a critical barrier to discovering novel lncRNAs throughout the progression of primary to metastatic disease correlated to treatment response and resistance. To address this, we have conducted a meta-analysis of normal, primary, and distant metastatic tissues from CRC patients across two independent patient cohorts to discover differentially expressed (DE) lncRNAs in metastatic tumors compared with primary tumors, termed RNAs Associated with Metastasis (RAMS). We have prioritized RAMS11 as it was a top up-regulated lncRNA in metastasis and associated with poor disease-free survival across multiple cohorts. We then demonstrate that RAMS11 promotes aggressive phenotypes in vitro and in vivo. While lncRNAs have been shown to promote tumor progression[26-28], the understanding of their role in treatment resistance is still unknown. Therefore, we have utilized a drug screen to discover that RAMS11 promotes resistance to topoisomerase inhibitors and provide mechanistic insight into RAMS11-dependent topoisomerase II alpha (TOP2α) regulation to promote mCRC.

Results

LncRNA Landscape of mCRC

To identify consistently altered lncRNAs during mCRC, we performed transcriptome sequencing and analysis of 37 patients from two independent cohorts. The first cohort includes ten normal colon epithelium, two primary CRC, and fourteen distant mCRC patient samples collected from Washington University, termed WUSTL cohort. The second cohort is from a previously published transcriptome sequencing study by Kim et al.[29] using matched normal, primary, and metastatic samples from 18 CRC patients, termed Kim cohort (FIG. 1a).

To identify lncRNAs altered in the metastatic samples relative to primary and normal samples, we performed a meta-analysis of the WUSTL and Kim cohorts. We identified 148 DE lncRNAs (FDR <0.05, fold change >2) in metastasis, termed RAMS (FIG. 1b; see TABLE 1). Several previously well-known and characterized lncRNAs known to promote oncogenic phenotypes in CRC or other cancer types were also detected. This includes increased expression of H19, HULC, CCAT4, and TCONS_12_00022545 in mCRC and decreased expression of FENDRR in metastatic samples[30-34] (FIG. 1b). Overall, this serves as a key meta-analysis from aggressive CRC patient tissues to establish the mCRC lncRNA landscape.

TABLE 1

List of identified differentially expressed RNAs Associated with Metastasis (RAMS) in colon cancer.

| RAMS ID | Gene ID | Gene Symbol | WUSTL and Kim Combined MvP status | TCGA.survival outcome association | Sveen survival outcome association |
|---|---|---|---|---|---|
| RAMS1 | ENSG00000130600.15 | H19 | upregulated | no-association | no-association |
| RAMS2 | ENSG00000251164.1 | HULC | upregulated | NA | NA |
| RAMS3 | ENSG00000259187.1 | CTD-2008A1.1 | upregulated | no-association | NA |
| RAMS4 | ENSG00000228705.1 | LINC00659 | upregulated | no-association | no-association |
| RAMS5 | ENSG00000255284.1 | AP006621.5 | upregulated | no-association | no-association |
| RAMS6 | ENSG00000272430.1 | RP11-38L15.8 | upregulated | no-association | no-association |
| RAMS7 | ENSG00000259347.5 | RP11-798K3.2 | upregulated | no-association | no-association |
| RAMS8 | ENSG00000224122.1 | POU6F2-AS1 | upregulated | no-association | no-association |
| RAMS9 | XLOC_007868 | NotAvail | upregulated | NA | NA |
| RAMS10 | ENSG00000266258.1 | RP11-4I04.1 | upregulated | no-association | no-association |
| RAMS11 | ENSG00000235899.1 | LINC01564 | upregulated | bad-outcome | bad-outcome |
| RAMS12 | ENSG00000251637.6 | RP11-119D9.1 | upregulated | no-association | no-association |
| RAMS13 | ENSG00000233203.6 | RP11-67L3.4 | upregulated | no-association | no-association |
| RAMS14 | XLOC_006188 | NotAvail | upregulated | NA | NA |
| RAMS15 | ENSG00000250337.5 | LINC01021 | upregulated | no-association | no-association |
| RAMS16 | ENSG00000235385.1 | GS1-600G8.5 | upregulated | no-association | bad-outcome |
| RAMS17 | ENSG00000266088.5 | RP5-1028K7.2 | upregulated | no-association | good-outcome |
| RAMS18 | ENSG00000273174.1 | RP11-434H6.6 | upregulated | no-association | good-outcome |
| RAMS19 | XLOC_001264 | NotAvail | upregulated | NA | NA |
| RAMS20 | ENSG00000256969.1 | RP11-320N7.2 | upregulated | no-association | no-association |
| RAMS21 | ENSG00000253426.5 | RP11-10A14.4 | upregulated | no-association | no-association |

TABLE 1-continued

List of identified differentially expressed RNAs Associated with
Metastasis (RAMS) in colon cancer.

| RAMS ID | Gene ID | Gene Symbol | WUSTL and Kim Combined MvP status | TCGA.survival outcome association | Sveen survival outcome association |
|---|---|---|---|---|---|
| RAMS22 | ENSG00000236924.1 | RP11-390F4.6 | upregulated | bad-outcome | no-association |
| RAMS23 | ENSG00000253428.1 | CTB-43E15.2 | upregulated | no-association | no-association |
| RAMS24 | ENSG00000232310.6 | RP11-557H15.4 | upregulated | no-association | no-association |
| RAMS25 | ENSG00000260015.1 | RP11-510M2.5 | upregulated | no-association | NA |
| RAMS26 | ENSG00000224251.6 | RP11-499O7.7 | upregulated | no-association | good-outcome |
| RAMS27 | XLOC_005488 | NotAvail | upregulated | NA | NA |
| RAMS28 | ENSG00000271239.1 | RP11-238F2.1 | upregulated | no-association | no-association |
| RAMS29 | ENSG00000278451.1 | RP11-923I11.8 | upregulated | NA | NA |
| RAMS30 | XLOC_003471 | NotAvail | upregulated | NA | NA |
| RAMS31 | ENSG00000235142.7 | RP1-60O19.1 | upregulated | no-association | no-association |
| RAMS32 | ENSG00000254235.5 | RP11-115J16.1 | upregulated | no-association | no-association |
| RAMS33 | XLOC_001263 | NotAvail | upregulated | NA | NA |
| RAMS34 | XLOC_005414 | NotAvail | upregulated | NA | NA |
| RAMS35 | ENSG00000249201.2 | CTD-3080P12.3 | upregulated | bad-outcome | no-association |
| RAMS36 | XLOC_I2_014067 | NotAvail | upregulated | NA | NA |
| RAMS37 | ENSG00000233415.1 | RP11-101E14.3 | upregulated | no-association | no-association |
| RAMS38 | ENSG00000259417.2 | LINC01314 | upregulated | no-association | no-association |
| RAMS39 | ENSG00000258551.5 | RP11-661P17.1 | upregulated | bad-outcome | no-association |
| RAMS40 | ENSG00000259134.5 | LINC00924 | upregulated | no-association | no-association |
| RAMS41 | XLOC_005087 | NotAvail | upregulated | NA | NA |
| RAMS42 | ENSG00000230647.1 | AC022816.2 | upregulated | no-association | NA |
| RAMS43 | ENSG00000263316.1 | RP11-530N7.3 | upregulated | no-association | NA |
| RAMS44 | ENSG00000237517.8 | DGCR5 | upregulated | no-association | no-association |
| RAMS45 | ENSG00000224137.1 | AC079767.4 | upregulated | no-association | no-association |
| RAMS46 | ENSG00000233590.1 | RP11-153K11.3 | upregulated | no-association | bad-outcome |
| RAMS47 | ENSG00000282097.1 | RP4-781K5.7 | upregulated | NA | NA |
| RAMS48 | ENSG00000232721.2 | RP11-403I13.5 | upregulated | no-association | no-association |
| RAMS49 | ENSG00000226674.8 | TEX41 | upregulated | no-association | no-association |
| RAMS50 | ENSG00000262445.3 | CTD-2545H1.2 | upregulated | no-association | bad-outcome |
| RAMS51 | ENSG00000227066.1 | RP3-340N1.2 | upregulated | no-association | no-association |
| RAMS52 | XLOC_005164 | NotAvail | upregulated | NA | NA |
| RAMS53 | ENSG00000261058.1 | RP11-252E2.2 | upregulated | no-association | NA |
| RAMS54 | ENSG00000244128.5 | LINC01322 | upregulated | no-association | no-association |
| RAMS55 | ENSG00000243694.2 | RP11-6B4.1 | upregulated | no-association | no-association |
| RAMS56 | XLOC_002717 | NotAvail | upregulated | NA | NA |
| RAMS57 | ENSG00000253666.1 | KB-1615E4.2 | upregulated | no-association | no-association |
| RAMS58 | ENSG00000256948.1 | RP11-598F7.3 | upregulated | no-association | no-association |
| RAMS59 | ENSG00000228709.1 | AP001065.15 | upregulated | no-association | no-association |
| RAMS60 | ENSG00000258460.1 | RP11-168L7.1 | upregulated | no-association | no-association |
| RAMS61 | XLOC_002277 | NotAvail | upregulated | NA | NA |
| RAMS62 | ENSG00000276850.4 | CH17-360D5.2 | upregulated | no-association | good-outcome |
| RAMS63 | ENSG00000232560.6 | LINC01549 | upregulated | no-association | no-association |
| RAMS64 | ENSG00000260603.1 | GS1-21A4.1 | upregulated | good-outcome | no-association |
| RAMS65 | ENSG00000250237.1 | CTC-498J12.1 | upregulated | no-association | no-association |
| RAMS66 | ENSG00000231013.1 | AC013275.2 | upregulated | no-association | no-association |
| RAMS67 | ENSG00000242522.1 | KLHL6-AS1 | upregulated | no-association | no-association |
| RAMS68 | XLOC_I2_011785 | Chen-etal-met | upregulated | NA | NA |

TABLE 1-continued

List of identified differentially expressed RNAs Associated with Metastasis (RAMS) in colon cancer.

| RAMS ID | Gene ID | Gene Symbol | WUSTL and Kim Combined MvP status | TCGA.survival outcome association | Sveen survival outcome association |
|---|---|---|---|---|---|
| RAMS69 | ENSG00000243384.1 | RP11-475O23.2 | upregulated | no-association | no-association |
| RAMS70 | ENSG00000189419.6 | SPATA41 | upregulated | no-association | no-association |
| RAMS71 | ENSG00000267250.1 | RP11-118B18.2 | upregulated | bad-outcome | no-association |
| RAMS72 | ENSG00000236849.5 | LINC01474 | upregulated | no-association | no-association |
| RAMS73 | ENSG00000275392.1 | RP11-164O23.8 | upregulated | no-association | NA |
| RAMS74 | ENSG00000269486.2 | CTC-360G5.9 | upregulated | bad-outcome | no-association |
| RAMS75 | ENSG00000223784.1 | RP11-554I8.2 | upregulated | no-association | no-association |
| RAMS76 | ENSG00000254542.1 | NAV2-AS3 | upregulated | no-association | no-association |
| RAMS77 | ENSG00000248319.1 | RP11-205M3.3 | upregulated | no-association | no-association |
| RAMS78 | ENSG00000240040.5 | AC096579.13 | downregulated | no-association | no-association |
| RAMS79 | ENSG00000269936.3 | RP11-394O4.5 | downregulated | NA | NA |
| RAMS80 | ucsc_AK128652 | AK128652 | downregulated | NA | NA |
| RAMS81 | ENSG00000249669.4 | MIR143HG | downregulated | no-association | no-association |
| RAMS82 | ENSG00000248771.5 | LINC01207 | downregulated | no-association | no-association |
| RAMS83 | ENSG00000184809.12 | B3GALT5-AS1 | downregulated | no-association | no-association |
| RAMS84 | ENSG00000253701.2 | AL928768.3 | downregulated | NA | NA |
| RAMS85 | ENSG00000275871.1 | RP11-394O4.6 | downregulated | no-association | NA |
| RAMS86 | ucsc_BC042823 | BC042823 | downregulated | NA | NA |
| RAMS87 | ENSG00000254645.1 | RP11-396O20.2 | downregulated | no-association | no-association |
| RAMS88 | ENSG00000248211.1 | TRPC7-AS1 | downregulated | no-association | no-association |
| RAMS89 | ENSG00000231407.5 | RP11-576I22.2 | downregulated | no-association | no-association |
| RAMS90 | ENSG00000270058.1 | RP11-514D23.3 | downregulated | no-association | no-association |
| RAMS91 | ENSG00000272840.1 | RP11-379B18.6 | downregulated | no-association | no-association |
| RAMS92 | ENSG00000268388.5 | FENDRR | downregulated | no-association | no-association |
| RAMS93 | ENSG00000224984.1 | RP11-524H19.2 | downregulated | no-association | no-association |
| RAMS94 | ENSG00000226363.3 | HAGLROS | downregulated | no-association | no-association |
| RAMS95 | ENSG00000255007.1 | CTD-2589M5.4 | downregulated | no-association | no-association |
| RAMS96 | ENSG00000249279.5 | CTC-436P18.3 | downregulated | no-association | no-association |
| RAMS97 | ENSG00000268754.1 | RP11-514D23.2 | downregulated | no-association | no-association |
| RAMS98 | ENSG00000254204.1 | RP11-400K9.3 | downregulated | no-association | NA |
| RAMS99 | ENSG00000254319.5 | RP11-134O21.1 | downregulated | no-association | no-association |
| RAMS100 | XLOC_011298 | NotAvail | downregulated | NA | NA |
| RAMS101 | ENSG00000253853.1 | GS1-57L11.1 | downregulated | no-association | no-association |
| RAMS102 | ENSG00000226777.7 | KIAA0125 | downregulated | no-association | no-association |
| RAMS103 | ENSG00000270403.1 | RP11-35P15.1 | downregulated | no-association | no-association |
| RAMS104 | ENSG00000238246.1 | RP11-575A19.2 | downregulated | no-association | no-association |
| RAMS105 | ENSG00000237807.3 | RP11-400K9.4 | downregulated | no-association | no-association |
| RAMS106 | ENSG00000260337.3 | RP11-386M24.6 | downregulated | no-association | no-association |
| RAMS107 | ENSG00000233968.6 | RP11-354E11.2 | downregulated | no-association | no-association |
| RAMS108 | ENSG00000277010.1 | RP11-616M22.12 | downregulated | no-association | no-association |
| RAMS109 | XLOC_001446 | NotAvail | downregulated | NA | NA |
| RAMS110 | LOC284578 | LOC284578 | downregulated | NA | NA |
| RAMS111 | ENSG00000258216.5 | RP11-654D12.2 | downregulated | no-association | NA |
| RAMS112 | ENSG00000228222.1 | AC074363.1 | downregulated | no-association | no-association |
| RAMS113 | ENSG00000224958.5 | PGM5-AS1 | downregulated | no-association | no-association |

TABLE 1-continued

List of identified differentially expressed RNAs Associated with Metastasis (RAMS) in colon cancer.

| RAMS ID | Gene ID | Gene Symbol | WUSTL and Kim Combined MvP status | TCGA.survival outcome association | Sveen survival outcome association |
|---|---|---|---|---|---|
| RAMS114 | ENSG00000261729.1 | GS1-204I12.4 | downregulated | no-association | no-association |
| RAMS115 | XLOC_010255 | NotAvail | downregulated | NA | NA |
| RAMS116 | XLOC_000371 | NotAvail | downregulated | NA | NA |
| RAMS117 | ENSG00000273244.1 | KB-7G2.8 | downregulated | no-association | NA |
| RAMS118 | ENSG00000272463.1 | RP11-532F6.3 | downregulated | no-association | no-association |
| RAMS119 | ENSG00000226087.1 | AC106869.2 | downregulated | no-association | no-association |
| RAMS120 | ENSG00000233214.1 | AC002511.2 | downregulated | no-association | no-association |
| RAMS121 | ENSG00000254510.1 | RP11-867G23.10 | downregulated | no-association | no-association |
| RAMS122 | ENSG00000228221.5 | LINC00578 | downregulated | no-association | no-association |
| RAMS123 | ENSG00000242611.1 | AC093627.8 | downregulated | no-association | NA |
| RAMS124 | ENSG00000277631.4 | PGM5P3-AS1 | downregulated | no-association | no-association |
| RAMS125 | ENSG00000174403.15 | C20orf166-AS1 | downregulated | no-association | no-association |
| RAMS126 | XLOC_009313 | NotAvail | downregulated | NA | NA |
| RAMS127 | XLOC_010043 | NotAvail | downregulated | NA | NA |
| RAMS128 | ENSG00000235049.1 | LINC00940 | downregulated | no-association | no-association |
| RAMS129 | ENSG00000225655.5 | PGM5-AS1 | downregulated | no-association | no-association |
| RAMS130 | ENSG00000231943.7 | PGM5P4-AS1 | downregulated | no-association | no-association |
| RAMS131 | ENSG00000228561.2 | RP11-114M1.1 | downregulated | no-association | no-association |
| RAMS132 | XLOC_004806 | NotAvail | downregulated | NA | NA |
| RAMS133 | XLOC_002932 | NotAvail | downregulated | NA | NA |
| RAMS134 | ENSG00000267405.1 | CTC-296K1.4 | downregulated | no-association | no-association |
| RAMS135 | XLOC_000897 | NotAvail | downregulated | NA | NA |
| RAMS136 | XLOC_002811 | NotAvail | downregulated | NA | NA |
| RAMS137 | ENSG00000243832.1 | RP11-202A13.1 | downregulated | no-association | no-association |
| RAMS138 | ENSG00000232680.2 | AC002511.3 | downregulated | no-association | no-association |
| RAMS139 | ENSG00000268505.1 | RP11-805I24.3 | downregulated | no-association | no-association |
| RAMS140 | ENSG00000260057.5 | LINC01571 | downregulated | no-association | no-association |
| RAMS141 | XLOC_012047 | NotAvail | downregulated | NA | NA |
| RAMS142 | ENSG00000239268.2 | RP11-384F7.2 | downregulated | no-association | no-association |
| RAMS143 | ENSG00000258537.5 | FRMD6-AS2 | downregulated | no-association | NA |
| RAMS144 | ENSG00000245870.2 | LINC00682 | downregulated | no-association | no-association |
| RAMS145 | ENSG00000257582.5 | LINC01475 | downregulated | no-association | NA |
| RAMS146 | ENSG00000250252.1 | RP11-342A1.1 | downregulated | no-association | no-association |
| RAMS147 | ENSG00000228778.1 | RP11-129J12.1 | downregulated | no-association | no-association |
| RAMS148 | XLOC_012622 | NotAvail | downregulated | NA | NA |

RAMS11 (Gene: LINC01564) (SEQ ID NO. 1) (bolded italic regions are exons that were targeted)

```
ACTACCTGCTTCTGCTGTGCACTCGCTCTCTCCCTCTTTGCTTCTAGCATAACAAATACG

TTCCCCTGCATTGAACGTGTTTTCCTAACAACAGTGGCGAGATGTGACAAGGAAACTTGT

TTGGAGCAACGTCTGAGTCACAATAGAATTAGTATCAGGTACAAATGACCACAAAGTACA

GGTGCTGAGTCACAGTGATTTGGGATTCTCTAGTAAAAAGGACATGTGGAGAACTTAACT

TTTATTTCCTCTCTTTTGCTGGTGTAAGTTTGGAGGTATCGTCACACAATCACCTTTCAT

TCACTAACGCTCACATTTTAGGTGCTTTTCCTTCTTACATAATAAAATAGCAAAGCACAT

AGGCCTGGGGTCCCTGGGGAAAGCCAAGTCTGCCTGGCTGCCTTGAGAACTCTGGACTGG

ATTTGACATGGAGGAGTTGGGGATTGTTGCTCAGGGATCAGAACAGTGAAACTCAGGTTA

ATGAGTAAAGAGTGAGAATATGTGTTTGTATGTTTCTTAATCCCATCTACTAGGTGATTA
```

```
CAAAACTCATTCAAAGTTGAACACAGTAGAGGTATTTCAAGTTGCTTTAGAGAGAATT

ACACACACACAAAAAATCTTTAGGAGCCAGACAACCACTGTGGACACCAATAAGAGAGCT

CCAACATTGGTGAGGTATAGACCCGTCAAAGTIGTTGGTAATAACAGCAAGGTCCATCTG

GCAAGATTGGTCACCTGTGGTGGAAGTGGTGGTGACAGCAGGGATGCAACTGCAGCAATC

AATGATGATGATCTCACTAGGGTGGGGAGGTGTTAAAGGCATCTTCACAGCAGCACAGTG

CCC*AGAATGCCAAAGAGCAGCAGGATGGATCCAGCATCCTCTCCTGATAAAAGAGGGCTA*

*GAAGACGGGAGGCTCCGGGAAGTCTACTGG*GTGAGTATTAGTCCACTCTCACATTGCTAT

CAAGAAATACCTGATACTGGGTAATTTATAGAGAAAAAAGGTTTAATTGACTCACGGTTC

TGCAAGCTGTCCAGGAAGCATAGCGGCTTCTGACTCTGGGGTGGCCTCAGGAAGCTTCCA

ATCATGGAAGAAGGCAAAGTAGGGGCAGGTATCTCACATGGCAGTAGCAGGAGGAAGAGA

GCGAGGGGGAGGTGCCACACACTCTTTAACTACCAGATCTGACAGATAACTCATTGTTCC

AAGGGCAGGACAAAGGGGATGCTGCTAAACCATTCATGAGAAATCTGCCCGCATGATCCA

ATCACCTCCCACCAGGCTCCACCTCCAACACCGGATATTACAATTCAACACAAAATTTGG

ACAGGAACACAGATCCAAACTATATCAGGGTGGAGCCCTACATCTAATGTTTCTTGCCCT

TGCTCTTGGTAGCTAGTGTCTCATTGGACTCTAGTGTCTGCTTGTTCTATTGGATCAGGA

GCTCCTTGAGGGGAGGAGCCATATTAAATTCATCTCTGTACCCCTAGTGTTTAGCAGTGT

TTTATTGAGTTAGTAAATAAATCCATCTCTATTCTTTATCAAAACTCTGAGCTGTGATGA

AAAAGTCACTGTCTCCACCTGTGCTTTGGATCTGTCAGTAGGGCCTTTGCTTCTACAGTA

ACATCATCCTACACAGAGTAAACACCTACTGAGTGCTGATTATGCCTGCTGTGGTTACTA

CAATCTCTTAAGTTTGCCTTTAAGCTTTGTATGTAAAATTTTTAATTGCTTTGCTATTTT

AATCTGATCACATTCCCCTGGTTCCTCCCTTTTAACTTTAAGCATATGCAATGTGCCCGT

TTGCACAACAGTCTGAAGTTTTATTTCTATGATTCCTCCTTTTCTGCACAAATGTTCATG

TTTCTCATACTTCCTATTACTTCTGAACATTTTCCTAATGACAGAAGTCATAGAAGCACT

CCTTAAAAGTTGATTTTTTGTTTGTTTGTTTGTTTGTTTTGAGACATTCTGCCACC

CAGGTTGGAGTGCAGTGGCATGATCATGGCTCACTGCAGCCTCGACCTCCTGGGCTCAGG

TGATCCTCCCACCGAAGCCTCCTGAGTAGCCGGGACTACAGGCACCTGCCACCACACCCA

GCTATTTTTGTATTTTTTGTAGAGATGAGGTTTCACTATGTTGCCAAGGCTGGTCTAGA

GCTTCTGGGCTCAAGCAATCTGCCCACCTCAGCCTCCCAAAATGTTAGAATTATAAGCAA

GAGCCACTGTACCCAGCCGAGAGCTGATTTTATATTAATATCTACAGCTCTGGTTAGACA

CAGTCTCAGGGAATTTGTGGCCAGTCTGTAGTGTTGTCTCCTTACTTAAAAAATACTCCT

TCCTTGACCTCACTTCAGTGTCTAATTATAATTTCATTTTCTACATCTATCCATGAAAAA

AATGTATAGAGTGGGGGAAATCTACCTTTCCACCTCCATTTCCTCATCATCCACTTCCA

CCTGAACTTGCTGCCACCTGACTTCAGCTTCACCACCTGTGAACACATCACTTTCTCTAA

AGCCTCCCACGCTTTCCTTCTGACCTTGAGCCAGTGGGCTGTTTTCATACTTCTCTTTCA

TAGTTACTTAGTTGCGTTAACATTGTCAAAAAGTAAAACAAAACTCCCAAGCCTAAAGCC

TCCCCTGCTTTGAGACAGTCTCCCCATCCTGACACCTGTGACCCTGAGTTCATCTGCATT

ATTCCAACCCATCTGGTGAATGAGTTAATGCTGATTTTTGATCATCCAACATGGTGTCAG

CCTCCTTCAGCCTTCCAAGGTGAGCCTATGAATTTCCTCCCTTCTAAGTCCACATACGTT

TGTTTCCTCCCACTCTGCATCTTTACCCCATTCATGGCACTCTTAACTCCACATAGCCCC
```

```
TTAGTTTTCTAAACCCATTTAAAACCTTACACCATCAAGGAGAAGCATAGCTTCTTAAAC

TTTCCCTACTGTAATGGCTTCTCAGGGTTTGTGTGAACAGTGGGGGTTTTTAATTTTTTG

GTATAATACTAATTTATCAACACATGTATACTTCTTGGTGAATATGCTTAAGGTTATTTT

TTTCATGAGTGTATATTGCTCCCCGAGATCCTTTCTTGCATTTGGGTTTTTTCCAAAATG

CTTAATATGGTCCTCCATATGCAGAGGACACTAGCTAAATATTGGTTAAAGTGGGTAACA

ATTAAAAATGTAATACTCCTGCCAGCTGAGTAAATACTTAACTTGCTTAATATGACCGTG

ACAATTTGTCCAGACACTGCCATTTCCTGCTTTCAGGGCACTGTTGTCTGTTGCTAACTT

ATTGCTCCTCTGGGTCTCCTTTTCCTACCTGGTTCAGATGTAGAATGTGGGGCTTACAAA

GTTAGAGGAGGACATTTTCTTATGGGTTTTGTTACCTATACCAGTAAGTTAGAAGGAAAA

ACTCACTAAGGAAAAACCAAACCTAACCATTTTTTACACAGCCAACACAGAGCATTTCAC

CTCTAGTCTCCAAAATATATAGGGATTTCTCCCCACCAGCAACCAATAAATTCCCTAGCA

GATATCAGCTATGTGTACTATAATTTAATTCAATTCTGACACTATCTATCTGGAGATAGC

ATCAGATCCCACAGAATAAGGGTTCTACCCCACAGGACTGCCCCCACTTCAGAGGCCGAT

CACGAGTTACAGGTTGTCACCTCTGCTTCTGCTGATCAGCTATAAGTCAAGATTCCCACT

ACTGTCTCCTTGGGTTCAATTAATTTGCTAGGATGACTTACACAACTCAGAGGAACACCT

ATTTTTGTTTACTGGTTTATTATAAAGGATACTAAAAAAGATACAGATGAACAGCCAGGA

GGAAGAGATGCATAGGCAAGGCATGTGGGAAGGGGCATGGAGCTTCCATGCCCTCTCTGC

ATGTGCCACCCTCCAGGACTTTCCACACGTTCAGCTATCCAGAAGCTCCTGAACCTGGTC

ATTTTGAGTTTTTATGAAGGCTTCATCATGTAGGCATGATTGATTAAGTCATGAGCCATT

GGTCAGCCCCTGTTTCTTCCCTGGAGGTGAAGGTTGATTGGTGGGACTTTAAGTCCCAAC

CGTCTAATCATGCCTTGGTCTTTCTGGTGACCAGCCCCCATACGGAAGCTACTTAGGGGT

CCCTAGGCATCAGTAATCTCCACAGCATATCAAAGACACTCATCACTTTGGAGATTCCCA

AGGGTTTTAGAAGCTGTATGTCAAGAAACAGGAGCAAGCCCAAATACATATTTCATAATA

TCATAACCATGTGACAACTTATCATAAAGACCAGGTACTCACTTACCAGACTGAATGCCT

GTAAGAGTTGATGAAGTTTACTTGAGCGGAGAAGGAACTGATGGAAGCCTCTCGTGCCAG

ACAGGTTGAAGTTCAGGTTTGCCATACTCTAGTAGTATGATTTTGGCAAAGTTACTTAAC

TTCTCTGTGCCTCAGTTTCTTGTGCCAATGAAAGGAGATTGAGAAAGTGAATGGGGCAAA

ATACTAACATTTGATGAATCTGGGTAAAGGGTATACAGGCTTCTATCTACTATTTTGTA

ACTTTTCTATAAATTTGAAATTATTTCAAAATAAAAAGTAAAAAAAATACTCTTGTGACT

TGGAGACTCAATTTTTCCATTTGCAAGATAGTTGAGTTTTCACATATAGTCTTAAAGAAT

GATGCTAACATTTTCCGAGTGGCAAACTGGGACATTTTGTCTGAGGAATCTCTTTAAATT

TTTTAAAGATAAAAGTCTTTCAAAGATTATAAGTTAAAGCACATTAATAAACAGACTTTT

TAAAGAAGACTAAAATATATGACAAGAAATAAAAATGTAATAAACTACCTTTATTGGTTA

ATAAAAGACTTGAATTTTAAAGTCAGCAGTATATTGATCCACTAGTATTGTTTGAAGAAC

TCAGTTTGCTCAATAACGAATTTTTTTCCCCAAATTTCATTGCAAATCTTCATTGAAATT

GAATTATCATTGTTGACACCTCCAATTCATCCAAAGTTCTTAACCTAACAATATTGCTTC

TCAATGTGCCCAGAAGTGAAAAGACAAAATCATGTGTTTTTATTAGGTATGAAATATTCA

CATTCACAGAATAAAAATCTGTAAGTAAATTTTATCATCTCTAATACAAGGAGATTTTAT

CATCTCCTTTTGTGTGTTACACTCAGCTAGTAAGTTCTCTTTAAAATACAGTTTTGTGAT

ACAAAGTTAATTTTAAAACCATATTACCAAATAGCAGAGAATGTCAAAAACATGATAAGT
```

-continued

TGGCTTTCAGTTTAAAATGGAAATGTACTCCATTGCAACTTTTCCTAATTTTATACAG*AG*

*TCATGAAGACACTGAAAAGTGATGAATCCACATAACCATGACACTGGAAATGAAGTTTGA*

*GTGGCAGTCAGAATCTGGGAGGAAGCATTGCTAAGTGAAAATCTTATGGAGCTTGACTAA*

*AAATCCCTGTCAGGAACCGTCAAAAGCTGTGTCCCTGACATGAAAAATCTTGCTGGAAGT*

*TGAGAGAGGTTTATGCCTACTCCGTGATCCGGGAACACAAGACCTTTACCAACCAAAAAA*

*GTGGATAGCTGTTCTTCTGCTGTGAAGGTTAATAAAG*GTAAACATTATAATGGCCAGGGC

TGGGGTTGAGGCAGAAAGAAGGAAGAAGGAAAGAAAGAAAGAGACAAAGGTAATAATATT
AGTAAAGGTAAATAATGTTAGTGTCTCTCAAAACAAAAATAATTTGACAGAAAAAAGAAT
CATTTTATATTGATAAAAGATGTAATCCATAAAATAGATGTAAAATTCATGAGCTTCTAT
AGTATTACAATCTTTAAATGGAAAATTGACAGAAATATAATTGTTATAAAAGACATTAAA
ATATTTTCTCAAGATTTGGGAAAGACTAAAAAGTAAAACAAGATTGAATGAGTAGGCAG
ATCTTGAATTTTGTATTTTAAAAGTGGAGAATATACCTTTTCATGCAACCATGGATCATT
TGCAGTAGCTGATCATACCACTGGGACACAGAGAAAATTTTACTATGTAATAAAAATGAG
AACATGTAGAAGCCACATTCATATGATCAAAACTAACATACACTAAGAAAAGTTTAAACA
AAGTCTTCAATCCATGAGTTATCTAACAATTTCTAAAATGAAGTCAGAGTATTTGTTTTT
GAAACTTTAAAGTTTATATGTAATCTATAAGACAATATTCATAACAACACTTTATAACAA
CAAAATGGTGGAAATAACCCAAATGTTTGTTGGTAGAACATACCTATCAATGGAGAACTG
TGCAACTATAAATGAGGAGTCTCCAAATATGTTTCTATTTTTATATACTCTGCAGAATGC
ATTGTTATATGAAAAAAGCAAAAATGGAGGTAAATATACAATGTGCTACCATTTATCCAA
AACAGGTAACAAGAATATGAATATACATATATTAAAAATCACAACAGTCCAGGAGTGGTG
GCTTATGCCTGAAATCCCAGCACTTTGGGAGATGGAGGTGGAGGATCATTTAAGCCCAGG
AGTTTGAGACTAGGCTAAGCAACAGAGTGAGACATTGTCTCTACAAAAAAAAAAAAAAA
AAAAAGTTAGCTGGGCATGGTGGCATGCACCTGTGGTCCTAGCTATTTGGGAGGCTGAGG
TGGGAGAATCACTTGAGCCCAGGAGGTCATGGCTGCAGTGAGCTGGGATCATGCCACTAC
ACTCCAGCCTGGGTGACAGAGCAAGACCCTGTCTCAAAACAACAAAAACAACAAAACAAG
GGTATAACAAAACAAACAAAACTGAACAAAAATTAAAAATTGTTTACCTATATGGGAACG
GAGTAGAGAAAACATGGATTAAAAACAAAACTTCCTGATTATACCTTGTTTTGTAAGTTT
GACTTTGGAATGGTGCAAAGATTTTACATAATTATCAAATCAAATTAACAAAAAATTTCT
AAAAACTGAAAGGAAAATAAAAATTACTGTATTGAACTAGTTGCTTAACTACACAGAGAG
GAACTATATTAAGTAACTTTAAAAAAACAACAGAGATTTAACATACAAACCTAGTGGGAT
ATACCCTAAGAATAAAAAAAAATGCAAATACACTTTATGCCACTTTCAATTATCATGCTG
TTTATAATAATACTGGCACTGCTATTCTGAAACTATGGTATATATTACAGGATATGGCAA
ATAAGTACTTATATTGTTAAGAACTAAGTTGTAAGTATGAGAAAAAAATATAAAAGCGAA
GAAGCGCAAACCCTATAATCCTAAACTTGAATTGAAAACATCAGTATGAGCTCATGATAT
GTTTTCTCTTAACAAAACAAAATAACAACTTATTTCCTAACTCTGCCTGCTAAAAAGGCC
TAGAAACAGTGACCAGCTCAGCAGCAATGAGTTCCCATAACACCCAGACTGTAGTTTCTA
ATACAATTTTTCACTAAAAGGAATCCATATTCTTGGAAAGTCAGCTAATTTGAAGACTGG
GGAGCAAAAAATTCAAGAAGGCCTTTATCTTGGTTCTTTTGTGCTGTTATAACAAAGTAC

-continued

```
CTGAGACTGGGCAATTTATAAAAATCACAACTTTATTTCTCACAATTCTGGAGGCTAAAA

GTTCAAGAATAAGGCACCAGCAAGTTCAGTGTCTAGAAAGGACCCAGCGTTTGCTTCGAA

GATGGCGCCTTTCTGCTGCATTCTCTGAAGAGGATGGATGCTGTGTCCTCACATTGCAGA

AGTCAGAAGGGGAAAAAGGGCCTAAGCTAGTTCCCTGTAGCCTTTTTGCAAGGTACTAAT

CCATGTCTCGTGGCTGAATCACTTCCCCAAAAGTCTTAACTCCCAACATCACCACAATAG

AGATTAAATTTCAACACATGAATTTTGTGAGAACACATTGAAACCACAGCAGTCTTGGAA

CACATTGTCACACCACAAAGCAAGAACATTTCATTGACCACTAAAGTCGTGTCAGAAAGG

ACTCAGAATCCAATTTGAATATCTGGCCAAACTTCAGTGGCCAAAAAAGAGACAATTTGA

ATCAGGGATTGAGACATGGCAGCTTTGTTTAAATCCATGCATTCATAAAAGAACTCTTGG

TCACCTATAGAGGGTTCTGGGAAATGAGCTCATTATTTTGAGAACTGGTAAATACAAGGA

AAGGATCAAATGTGAATCCTACCTTTCCTGTACTAACTGTACCACAGAGTAACCAAATAG

TTGACAAAGGAAGTTTCTCTATTATGAAGTATTCTTGCTAATACATGATTAAGGAATGAG

AATTCGAGTATTTGCACATTCGAATGAAATAGTGGATTTAGGCTAAATGTCTAACATCAC

ACTAAGAGAAACAACTGGGCGCCTGCTAACAAAAGTCCTGTCACTATCACCAATGGTGTC

TTCTTGCAAAAAATTCCAATTATAAGTGATCAAATTACCTATTAGGGAGTGAGGGCACAG

GTAATGCAGAAGACAGCAAACATATGAACAATAGACACCACATGGATGCAATTAGCAAAA

TCCACAATTCTGGAAATTCTGCAGGGCAAACTGACCTAGTTTCTTCACCATATACATGGC

AAGGAGGGACTAGGGGGAGGAAGTGGCAGATGCTCTTGGTGCCCACCCATATCCTCTGTG

CCCTTCACTGTGCTCAGCCTTGCTCCCAACTGTCAGTAGCTGCCTTTTGGTGCCTAAGAG

CTTTTTTTTTTTTTCTCCTGAACTGCAGAACGCCAGAAGTGCCAAGCAATTAACAACCC

CAGAAGCAACCCTTAACCAATGATTAAATAAAGTGGATGATTACATACCCAAGCTCCTTC

AACTCCCAGGGACATAATTCTGAGGTGGGTGTATGTTTATCCCTTTTTCAAGAACTTCCC

CGAAGGATTAAGCTTCAGTCACCCACTGGTAAATTGCTTAACAGCTCAACCTCTATGGGT

TTGGGTTGCTTTTTCTTGTATCACATGCTGTCTCCTTTATGGTGTACACTGCACTTTCCA

AATTGACTACCTATACTTGAATCCTGTCTTAGATGTATTTCTGGAGGAACTCAAACTAAG

GCAGATGGGGAACTATAGATTAAATGAAACTTAAGAGATGTCAACCAACTGCAAAGTGTG

GAGCTGAGCAAAAACAAACAAACAAACAAACAAAAAAACTGTTCAAAAAGTTTATG

AGACAATCAGGGATATTTAAATACTGACTGAATATTTTATAACATTTAGAAATTATTGGG

GTTTTTAGGTGGCATAATACTGATAGGCTTATCTCTAAACCCATGATCAAATATTGGATA

TTTATAGATGAAATGTTAGGATGTCTGGGATTTGCTTTCAAATTAATATGGAGTGGAGTT

GTGATTGGTGATGAGTTGACAATTATTAAAACTGGGCACTAGTATGTGAGACTTTATGAT

ACCATTCTGTCCACTTTTGTAGATGTTGGAAATTTTCCCTAATTAGATACAAAAATGAAA

AAAGCTGAAAGCTCTATGGGGATTGTTAATAACTATGTTCTTAGTGCTTAACAGTGTTCA

GTACATAGTCAACAAAGAAGCACTCAAAACACTATTCATTGAACAACTGTTTTGTCTTAT

GTTGGGGATACCAAGGCAAATATTGTTGACATTGACATTTTTAGCTGACATACTGGAAAT

CTTACCAAGAGTTTTATACAGACTAGAGGAAAAAAATCATTTTATCAATTAGTACAATGT

CGGGTTCAAAAAATGTTATACTAGGTCTACTTCTAACTAAAGTATTTTTCAGCTTGTGAT

TCATCACCGTCTGTGTCTTGAAGGTATATTTGAGTTAACATATATTTTATTAGAATGTGC

TGTTTTTTGCCAAAATGCTGGAATTTCTGGGATACTTTGATGATTCAGTTGGACAGAATA
```

-continued

```
TGACACTGAATATTTGAAAGCAGGACTTGGTTAGAAAATCTAAGATTGTGAGTGCCGAAT

TTACCTAGTAGATATATGTTTCTGAAATTTACAAGGTAACTGCTTTTGTTGGGACCAAAA

CCACACAGCCAATAAAACTAAAACTGTACTGGGAAAATCATTTAAATAAAAGAATAGTAT

ATTAAGTTGGAGGGTAGGGTATATTTGAAGTCTTAGAGGCATGTAAACAGGAACTTGCAA

GAAATTCCAGCAGAAATTTTCCACTTTAAAAAATATAGATAAAGCTGGGCACAGTAGGGC

ATGTCTGTAGTCCCAGCTACTTGGGAGGCTATGGCAGGAGGATCACTTGAGGCCAGGAGT

TCAAGGCTGTAATACGCCTAGATTGTACCTGTGAATAGCCACTGCACTCCAGCCTGGGCA

ACATAGCAAGATTCCATCTCTAAAAAAATATAAATTTGATATAGATGTATCTATATATCT

GTCTCTAAAAAATTCTGTCACTTCCATGAGTTCACATTATTGCTGAGATTTATTTTCTTG

CAAGATTTTCTAATAACATGATAGTCCTTGTTTTCAAGCTGTCAGGTAGTAAAACAGTAA

TTTAATTTGGCAATAACATATGACATTCTAAGAAGACGCATTAGAAGGTTTTTAAGAAGT

GTACTGAAATATTTTTGGAATGTCCTTCAAACAGGCAAAGTTTAAACTGGAAAGAGCAAA

AAGTTAAATATTATATATTTATAAAAAGTCAAACTATTTTTTCCTTACCTGGTTAAAAAG

GTGTTACCAAGGTCGCAAAATAGCTTTGTATATTAAAAATTTTTTTTATTGGATTAATTC

CTAGTTGTAGTTTAGCTACTTATTTTTGTTTTTCATTTATCTTTTTCACCTCTATGTAGC

TTATGTTATTAAGTTATGTTATTAAGTTTTTAAATAAAACCTAGGAGGCTTCTTAATTCT

TTATGAAAAATTCTGTGAGAATAACTAGCTAAATTTTAAAACTACAACCAAATAAGATTG

ACATAATAATATGCATATACATTGCTCTTCTCACATTAACAATAATAGATTTGTATCTTC

TAAGATATCTCTGAGAATAAAATTTCCAGCCATATCATCAGCTAAATTAACTCAAATTTA

CTATCTGGATTTGGCTGTTTCACTTGTAGGTTAAAAGTTAAAAGGTTTGCTATTTCTTGG

AATCAAAGGTTATTTAATGAAAGAAGATTAATTTCAATAAATGATGCATTTAAAGTTTTT

TCCAACAAAGAGTGTAAGAGATTTATCACAGGTTCTAAATAACAAATTTAATTTCCCTAA

CATGTTAAGGAGAATTTTGGTTCCCGCAGAGGACTGAGTGGACTAATCATTTATAATAAG

ACTGACTTTAAACTTCCTTTTAACTTGACAGTAGTTAATTCTAACTTTATTAAATTAGAA

TCCCCATTAATTCACCCATTTTTCTTTCACCAATTTTGTTTTACAATTAAGGTTTATCTG

CAGAGTTCTGTTTTGACCATTATGCTGAAAGTGCTGAGTTCTGCTGTTTGCCTTCCTTCA

GCCTTTCTGGCTGAATGGCTTCCTGAATCTTCTCAGAGGTTTCCCTCTGAGCCCATGATG

GGGTTCTAAAAGCACATTCTGTTCATGTACTGGGATAGTGGGATGTGAGGGCAGAGAAGT

TCTTCCTGAGCATGAGTCCTTCATCCTCTACCCACTGTTTTATAAACCTGTCTCAAATTC

CATGCACTTTTGGACCCAGTTACTTGAACTCTCAGGAGCAGGTACTTTGTCACCTCCAGA

GGGAAGGCCAGCATCCTCCTAGCGGGTACTGCTGTGTGCTTGCCCCTGAGCCAGGAGCTT

TGCATTTGCTCTCTCATTTGATCCCCTCAACAACCCTAGTAGTGAGGAAATATCTATTTC

ATACATGAGGAAATTGAGGCCCAGAGAAGGCACTGGCTGCTTAGCTGTGTGCTGTCACCC

TGTTGAAACCAACGCCTCCTGCCTACACTGCCACTGCCTGTATAAACTGGTGCCACCCAC

GGTTATATGGCAGAAAGCAGTGCTTCGAGAAAATGGACCAGCAACCGCCATGTGTTGAAC

AGGCTATGGGCAGGAGGAAATAAAGCAGTTATAGCACCTGGGGGTGGAAGTCAAGGCAGT

AACCAAAATAAAGTGGGAGCACGGAAAAAAGCTGGGGAAATAAAAAGGTTCAAATTTCAC

ATTTCCTCATGAAGTCCAGATCAAGTTGGAGCTTGTTTAATAGCAGAAATTAGGCAGCCA

GACCTGTCTGTAGGGCAAAGAAATTTTTGTTGAAAAGCCCAGCAAGTATTTACTCCGCTG

TAACAGAGTCTTTTTCTAACTCCAGGATCTTTTCTTTGTGTGCTCTGTAGAATGAAGTGT

GCTTGTTTTGGTGGGGATACATTTACACAGTTCTCCATGTTTTGTTTCATCTTTCCTCTC
```

-continued

```
CGTGTTGTTGCTCTCTTTTTCCTTTGCTCTATCCAAAGATATCAGCCAAAGAAGCCAAGA

AAAATGTTATCTTTACTTTAGAATTAGGGATTTCAGATATGGGTAGATGGCTCTGTTAGG

CAGAAGTGTCAGAGCTGGTTATAGGAAAACCAGGCGGCACATACATGATCCCAGACACCG

AAGTAACCTCTGTCTCACTCCTCCACTTCCAGCAAGGTATTGTGCTCTGAGGGGCTGATG

AGAGAAGGTAGATTATGGGTCTGCCAAGGCTTTTTACTGGTCTCTGTTTATCTTTTTCTG

AGTGCCAATTCAGCATGATCTAGACCAGGATCATTTGTTTGCAG***GGATGGAAAACAAACT***

*GAAACTGGCTCAAGTGAATGCTCACTGGAAGGCTTACTGGAAAACTTACTGGAAGGATGT*

*GAGGACATGTTCGGGAATCTATTTGCAGAAAACATATTCAG*GTATACTGGGAGCTCTCCC

TCTCTCACATTGTCTCCCTCACTGAAACCAGGATTGCTGTCTATTTCCTTGGGGCTGTTG

CTGTCATGCTGTCTTACTAACTGTAGTGTTGTGTTAGCTACACGACTGCTCAAGTTTATT

TTTTTGAAAAATTGTGTTCCATTTAGCCAGGATGATGCAAGTTGTTTCAAGAAAGGCTAT

AAAATGCTTGCAATAAAAGTCATGTTCATTCACATTCATTAGGAAAAAATGAAATAAATC

TATGCTGCATAACTTTTTTCATGCCAAGTGCGGGAGTGGAGGTTGTCAAATCAAGACTGG

ATCATCAAGTACATAATGATAGGGTGCCAAAATTCCAAGGAGGTTGGGAGTCACTGTTGT

TGAGGGTGGTCAAAGAATTTGTTTCCCCACAAGGCATGTGGCTTTGGGCCAGCACACCTC

ATAATTCGTTCTCTTCTATTTCCCACATCCGTCTTATAATGTCTCAATTTAACCAGGGGA

ATATGGAGCGTGAACTCTTTCTATTTACCCTTTTAACATCCAGGTAGATATTTCTGAGAT

ACATGGCAATGTATCAGGGTTGAGTTTGCTGCTCTGGTTCTTATCCTTTTTTTTGAGAC

AGGTTCTTGCTCTGTTGCCCAGGCTGGAATGCAGTGGTGCAATCTCAGCTCACTGCAGAC

TCTGCCTCTGCCTCTTAAGTTTAAGTGATCCTCGTGCCTCAGCCTCCTGAGTAGCTGAGA

TTACCGGCACCTGCCATTGTGCCCAGCTAATTTTTGTATTTTTAATAATGGTGAGGTTTC

ACCATGTTGCCCAGGCTGGTCTCGAACTCCTGGCCTCAAGTGATCCACTTGCTTTGGCCT

CCCAAAGTGCCGGGATTACAGGTATGAGCCACCATGCCTAGCCTCTGGTTCTTATCCTTT

TGAAAGTCTTAAAGTCTCCTCTTCATTCATGTATCAAATATTTGATGAAATATTTGACCA

GATGTCAGAGTCTAGAACATCAGACCGAGATAGTAAACCAGTGGGTCGTAAATAGCTACA

TGAAGGGCATAGAATCTAAACAGATCCAGAGTGAGAGATTAAGGTCAAGGAACTGGAAGG

CATATCTGGATTTATTTATTTTTTTAAAAAAATACAGTATTTGTTTGGATGGAGAATGG

AAATAGAACTTGCAGTTTTGGTTCTCTGCAATGCAGGTTGGCCACTGCTATTGCTGTAAC

TCTGTCCTATTGTCCTACCCATACTACTGTTGTAACTTCCATAAGGTGGGACCTGATGAA

TCACGCACACTTCCAGAGTGTTTGGTCAGGGTGACCCTGGGTGCAGCAAGGATGGCCAAT

GCTGTTGGCATCAAAAGGCCAAGAGATGACTTTGGTCAGATTAGATAAAGACCATTTAGG

GCCATGGAGATATGGAAGCAATTTTCTTCTTTCCTAGAAGATGATGCAATAGATGACAAT

AAGCATTTGGGTGAATCTCTCCAGCCAGGTTTGAAGGCAGTTTGTGTCACGTAGTGGGTG

GGTGGATGGGAAAGTTAGTTCTAATTACTATTCCAGGGCCCTACATCCAGAACCTTTCC

ATTTTAAGACAAGAGGGGGACTAACATTCCCAGCTCATTCGCAAATGACTCAAGAGAATG

GGACAGAGGAAAGGGAGATACCATTTTTAATTCCCCCTGGAGGAGTCCTAATGTCCCATT

AGTGTTTCAACTGTTTGGTCTAATTCAGGTATGAAGTACAGTGGTTTGTTTGTTTGTTTG

TTTGTTTTGTTTTTTGTTTTTCATAAAATTGGTTGATTGATTAATAAATTGCTTGCTGGG

CATTGGGGAACTATACATGAAAATTATATGACTTTAACCCTGAAGGAGCTCAGAATCTAA
```

-continued

```
TGCGGAAGATGGATATTTATGATATATAACAAGGGCAACAATAAATCTAGTACAAGATAT

GAGGAATCTTCCAGGCTTTGTATTGGACAAAATGTCTCTGGGATGTCCTTTACCTGGAGG

CATATATGGGCCCAATGCCAGCTTCAGCTATTCTAAAAGAGACCTGAGTCTAAAGATCAC

ACATTATCTCATATCAGGAGCCATGCTCACTGACTGAAATTTCCCAGTGGCCACCAAGCT

ATCATTATGGTCCCTATAGTCCCACTAATTATTATCCATCCCACTTTGCTACTTCTGGAT

CGGACACTTGACAGATAATGTCAGGGACAGTATAGCGTGTGTTTTGCCCAAATGATCTTT

AAGACAGCCTCGTTCCCAGTCTGGCGGTTGTGTGGGAATCAGCATCTTCACTTCCTGATT

TCTATTACACTCCTTCCTACAG*CCCTGTCCACCACAGCCAGCTGGCTGAAGAGCTCAAAA*

*GGCAAGAAATCAGCAAGAGAGAGAGATGAAGCATGAGAAATGAGCAAAAAACACCCAGCA*

*CATCATAATCTTGGACAGTTTAGCAGTACATGAAAATAGATGGTCCTCGCCCCAAGGGAC*

*TGCAGTAACCCTGAATAAACAGGATGTCTCTCACTTTTAGCAGTTCTTTCTGTGCTAGTA*

*TTGGGGAAATATATTTTTGGCTGCATGCAAAATGTTAAAAGACATCTATTAAGAAAATGA*

*AAACAATGCTTCTGTTTTAGACGAAGCTTTTGAAGGTTTAAGGATCACCTATTTATTGAC*

*AAAATTGTTTCCGTGGCTTAAAAATAAAATACAAACAAATACTACAGGTA*TTCTTGCCTT

CTCATTCTACTTAAAATCACATTTCCAAAGACTTTCTTCTCTACTTAAAAACAGGAATTA

AGAAATACTCAAAAGAGATCCTAGACAAAACTAACATTTCAGCAACCAAAGATAAATCAT

GCTTTTAGAGGAAGATGCTAGGTTCTAGAATCTCTCTGAACACCGTGTAGCACTAAGAAA

CTACAATCACTGGCTGAGACCTTGATCAAATAATGGCTAACATATAAGATGCTTATTCTA

GTCAGGCACACTTCTAAGAGCTGTATATCTGCTAATTCATTTATTCTCCTAGGATATAAA

GGATCAGCAGATCCTTCAGGCTCTGGTATGTTCTGAGATGAGTTAACCCAGAAATTGTCA

TCAAAAGACAGATTCAGCAAAACGGAAACAGCCACCATTTTATGTAGATGTCCCTGTGGT

TTAGTGCTACAGACCGGACATTTGTGCCCTTAGGGGAAAAATGATGAGGTCAGAGCAGAC

TGGGATAGATCAGGTCTGGTGCTTTTATTGTAGATCCTGGAACCAAAGATGATCTTATGG

AAAGCCAGGTAGACAGTTCAGCTGAGGTATTCATCCATAGAGACTGGCCA
```

RAMS11 is Upregulated in mCRC

We prioritized our functional studies on lncRNAs that were highly deregulated and potentially clinically relevant in mCRC. To prioritize all RAMS, we evaluated whether their expression correlated with patient outcome. First, we found that six of the 148 RAMS were associated with disease-free survival using 232 patients from the TCGA CRC cohort (RNA-Seq). Among the six RAMS associated with survival in the TCGA cohort, only RAMS11 was associated with poor survival from a second cohort of 82 patients (FIG. 1a, FIG. 1c) from the Sveen study (GSE24549, exon array[35]). In the TCGA cohort, RAMS11 expression is enriched in microsatellite stable (MSS) patients (FIG. 1e), which have a worse prognosis compared to patients with microsatellite instability (MSI). RAMS11 expression is also enriched in the consensus molecular subtype 2 (CMS2; canonical) and CMS4 (mesenchymal), the latter associating with the worst CRC patient outcomes (FIG. 1f). The subtype association of RAMS11 is consistent with our data showing its upregulation in mCRC and highlights its potential as a marker of aggressive CRC and poor prognosis. It is currently accepted that colorectal tumors can be classified according to their global genomic status into two main types: microsatellite instable tumors (MSI) and microsatellite stable (MSS) tumors. This taxonomy plays a significant role in determining pathologic, clinical, and biological characteristics of colon tumors: MSS tumors are characterized by changes in chromosomal copy number and show worse prognosis, but the less common MSI tumors (about 15%) are characterized by the accumulation of a high number of mutations and show predominance in females, proximal colonic localization, poor differentiation, tumor-infiltrating lymphocytes, and a better prognosis.

Figure 11:
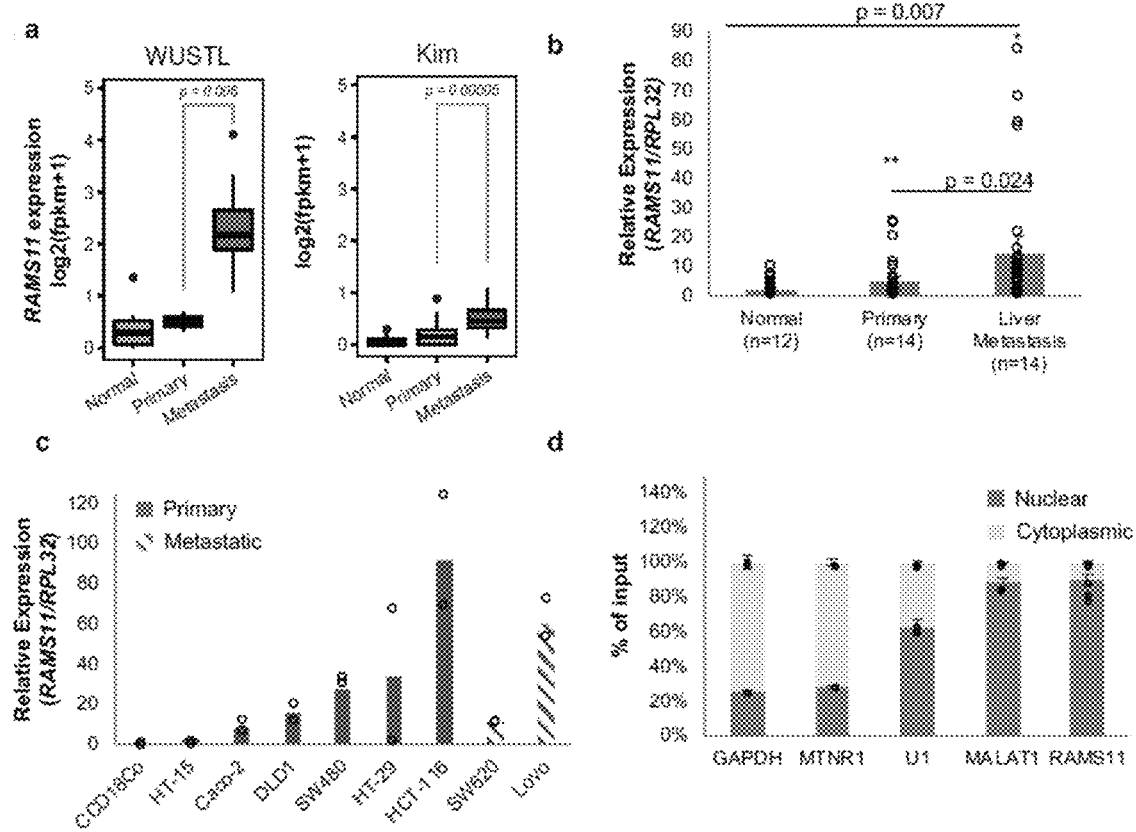
FIG. 11. RAMS11 expression in cell lines and patient tissues. (a) Expression of RAMS11 in WUSTL and Kim cohorts. Shown are boxplots with bo representing the interqartile range (IQR, $25^{th}$ to $75^{th}$ percentile) centered by median, whisker lines limited by 1.5xIQR away from the bo, and dots representing outliers. WUSTL Normal n=10, Primary n=2, Metastasis n=14, Kim Normal n=18, Primary n=18, Metastasis n=18 (b) qPCR validation of matched normal, primary, and metastatic patient samples showing increased RAMS11 expression in metastatic samples. Normal n=12, Primary n=14, Liver Metastasis n=14. Data shown as mean±SEM. (c) Expression of RAMS11 in colon cancer cell line panel. Experiment repeated two times. (d) RAMS11 is localized in the nucleus as shown by nuclear and cytoplasmic extraction. GAPDH and MTNR1 genes were used as positive known cytoplasmic control genes, and U1 snoRNA and MALAT1 lncRNA were used as positive known nuclear localized control genes. Data is presented as mean values ±s.d. Experiment repeated three times. All data is analyzed by two-tailed paired t-test. *p<0.05, ** p<0.005.

These results indicate that high levels of RAMS11 in primary tumors can serve as an indication of poor patient outcome. Notably, RAMS11 was also a top upregulated lncRNA in metastatic tumors (FPKM=4.81) as compared with primary tumors (combined $p=2.56 \times 10^{-10}$ average fold change=6.1) and normal tissues (combined $p=2.2 \times 10^{-20}$, average fold change=12.9) (FIG. 1d and FIG. 11a). We further validated the upregulation of RAMS11 by qPCR when comparing matched metastatic patient samples with normal (p=0.007, two-tailed paired t-test) and primary (p=0.024, two-tailed paired t-test) patient samples (FIG. 11b).

Our de novo transcript assembly using the WUSTL cohort identified RAMS11 as a five-exon transcript of 959 nucleotides, which we confirmed by 5' and 3' rapid amplification of cDNA ends (RACE) (FIG. 1d, TABLE 2).

TABLE 2

Sequence identified for RAMS11 5'3' RACE.

SEQ ID NO: 2
>hg38_dna range = chr6: 53616714-53616800
5'pad = 0 3'pad = 0 strand = + repeatMasking = none
AGAATGCCAAAGAGCAGCAGGATGGATCCAGCATCCTCTCCTGATAAAAG
AGGGCTAGAAGACGGGAGGCTCCGGGAAGTCTACTGG SEQ ID NO: 3
>hg38_dna range = chr6: 53621209-53621487
5'pad = 0 3'pad = 0 strand = + repeatMasking = none
AGTCATGAAGACACTGAAAAGTGATGAATCCACATAACCATGACACTGGA
AATGAAGTTTGAGTGGCAGTCAGAATCTGGGAGGAAGCATTGCTAAGTGA
AAATCTTATGGAGCTTGACTAAAAATCCCTGTCAGGAACCGTCAAAAGCT
GTGTCCCTGACATGAAAAATCTTGCTGGAAGTTGAGAGAGGTTTATGCCT
ACTCCGTGATCCGGGAACACAAGACCTTTACCAACCAAAAAAGTGGATAG
CTGTTCTTCTGCTGTGAAGGTTAATAAAG SEQ ID NO: 4
>hg38_dna range = chr6: 53624600-53624714
5'pad = 0 3'pad = 0 strand = + repeatMasking = none
AACGCCAGAAGTGCCAAGCAATTAACAACCCCAGAAGCAACCCTTAACCA
ATGATTAAATAAAGTGGATGATTACATACCCAAGCTCCTTCAACTCCCAG
GGACATAATTCTGAG SEQ ID NO: 5
>hg38_dna range = chr6: 53628575-53628691
5'pad = 0 3'pad = 0 strand = + repeatMasking = none
GGATGGAAAACAAACTGAAACTGGCTCAAGTGAATGCTCACTGGAAGGCT
TACTGGAAAACTTACTGGAAGGATGTGAGGACATGTTCGGGAATCTATTT
GCAGAAAACATATTCAG SEQ ID NO: 6
>hg38_dna range = chr6: 53631013-53631373
5'pad = 0 3'pad = 0 strand = + repeatMasking = none
CCCTGTCCACCACAGCCAGCTGGCTGAAGAGCTCAAAAGGCAAGAAATCA
GCAAGAGAGAGATGAAGCATGAGAAATGAGCAAAAAACACCCAGCACA
TCATAATCTTGGACAGTTTAGCAGTACATGAAAATAGATGGTCCTCGCCC
CAAGGGACTGCAGTAACCCTGAATAAACAGGATGTCTCTCACTTTTAGCA
GTTCTTTCTGTGCTAGTATTGGGGAAATATATTTTTGGCTGCATGCAAAA
TGGTAAAAGACATCTATTAAGAAAATGAAAACAATGCTTCTGTTTTAGAC
GAAGCTTTTGAAGGTTTAAGGATCACCTATTTATTGACAAAATTGTTTCC
GTGGCTTAAAA Previously, three exons of the RAMS11 transcript were annotated as LINC01564 (NR 125841) through a microarray probe-based analysis[36] (FIG. 1d). We further characterized RAMS11 expression in a panel of CRC cell lines. RAMS11 was highly expressed in a panel of six primary (more than three-fold increase) and two mCRC cell lines (more than 11-fold increase) compared with CCD18-Co, a normal colon control cell line (FIG. 11C). Since the cellular localization of lncRNAs can help decipher their functions, we fractionated LoVo mCRC cells with high endogenous expression of RAMS11. As shown in FIG. 11d, RAMS11 is predominantly expressed in the nucleus (89.5%), with only a 10.5% expression in the cytoplasm. Taken together, these results show that RAMS11 is a five-exon, nuclear localized, lncRNA that is highly expressed in primary and mCRC cell lines and absent in normal colon epithelium.

RAMS11 Promotes Aggressive Phenotypes In Vitro

To understand RAMS11 functional significance, we created a RAMS11 knockout (KO) model by generating two CRISPR/Cas9 luciferase-tagged cell lines with a genomic deletion of the last four exons of RAMS11 in the LoVo metastatic colon cancer cell line (FIG. 12a). We confirmed greater than a 99.9% reduction in our RAMS11 CRISPR KO models (clones referred to as CRISPR1 and CRISPR2) relative to wild-type cells (FIG. 2a) and confirmed that the genomic deletion of RAMS11 did not alter the expression of adjacent genes GCLC and KLH31 (FIG. 12b, FIG. 12c).

Figure 2:
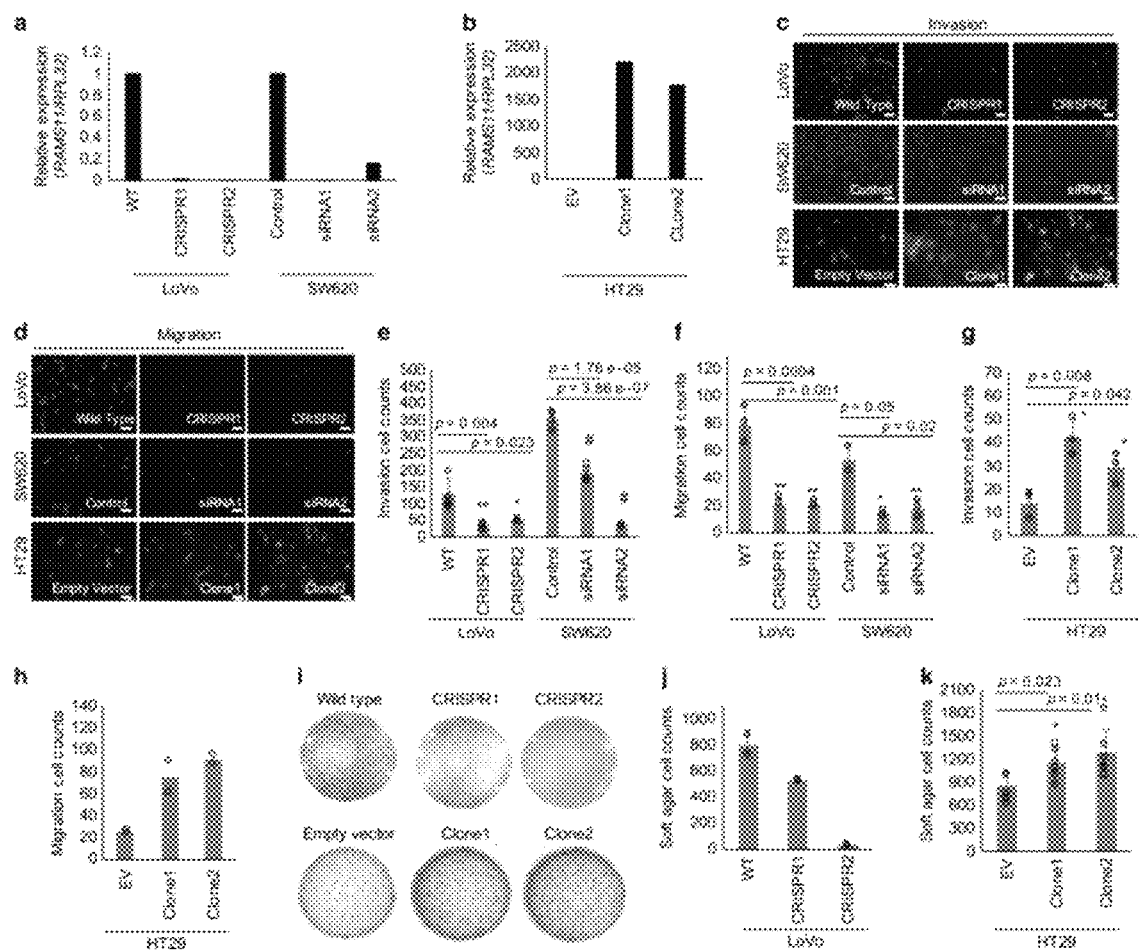
FIG. 2. RAMS11 promotes an invasive phenotype. Expression of RAMS11 in (a) LoVo CRISPR KO, SW620 silenced cells, and (b) HT29 overexpressing cells (Clone1 and Clone2) as measured by qPCR. (c) Images of DAPI-stained LoVo RAMS11 CRISPR KO cells and SW620 siRNA silenced cells show decreased invasion compared with controls. HT29 cell lines overexpressing RAMS11 show increased invasion. (d) Images of LoVo RAMS11 CRISPR KO cell lines and SW620 cells transfected with RAMS11 siRNAs show decreased migration. HT29 cell lines overexpressing RAMS11 show increased migration. (e, f) Quantification of invaded (n=4) and migrated cells (n=3) in LoVo and SW620 cells. (g, h) Quantification of invaded (n=3) and migrated cells (n=2) in HT29 cells. (i) RAMS11 CRISPR KO cells decreased growth on soft agar (n=2) and RAMS11 overexpressing cells (n=6) increased growth on soft agar. (j, k) Quantification of soft agar cells. All data are presented as mean values s.d, analyzed by two-tailed paired t-test, and repeated more than two times. Bar=25 μM, *p<0.05, **p<0.005, #p<0.0005.
Figure 3:
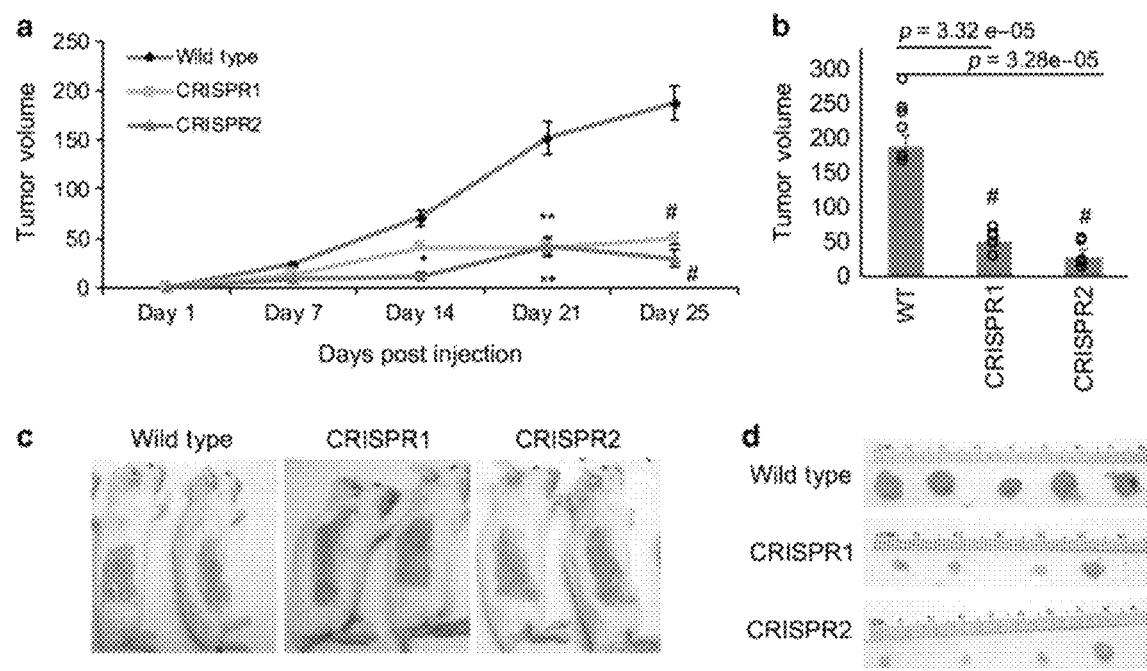
FIG. 3. RAMS11 induces tumor growth in vivo. (a) Significant decrease in tumor growth in RAMS11 CRISPR KO subcutaneous injected mice. Day 14 CRISPR1 p=0.01 CRISPR2 p=0.0002, day 21 CRISPR1 p=0.00002 CRISPR2 p=0.0006, day 25 CRISPR1 p=3.32e-05 CRISPR2 p=3.28e-05. (b) Quantification at day 25 showing decreased tumor growth in RAMS11 CRISPR KO lines compared with wild type. (c) Representative mice showing little to no tumor growth and d representative resected tumors from mice. Data shown as mean±SEM and analyzed by two-tailed paired t-test, with n=10 per group repeated two times. *p<0.05, **p<0.005, #p<0.0005.

We used these genetically engineered cell lines to determine changes in the invasiveness of cells using Matrigel-coated transwells in a modified Boyden chamber assay. There was more than a 60% decrease in invasion of RAMS11 CRISPR KO cells (CRISPR1 p=0.004, CRISPR2 p=0.023, two-tailed paired t-test) compared with wild-type cells (FIG. 2c, FIG. 2e). We also conducted a transient knockdown of RAMS11 in a second colon cancer metastatic cell line, SW620, and observed at least 80% knockdown in two independent siRNAs (FIG. 2a). We saw a 50% decrease of invaded cells relative to control cells that were transfected with scrambled siRNA (p<0.00005, two-tailed paired t-test, FIG. 2c, FIG. 2e). Conversely, stably overexpressing RAMS11 (Clone1 and Clone2) in HT29 cells, with low endogenous RAMS11 expression (FIG. 2b), resulted in a 53% increase in cellular invasion (Clone1 p=0.008, Clone2 p=0.042, two-tailed paired t-test) relative to the empty vector control cell line (FIG. 2c, FIG. 2g). Further, we rescued the number of invaded cells to wild-type levels with transient overexpression of RAMS11. Our CRISPR KO models re-expressing RAMS11 (CRISPR RAMS11 OE) revealed more than a 60% increase of invaded cells relative to the CRISPR KO cell lines (CRISPR1 RAMS11 OE and CRISPR2 RAMS11 OE p<0.00005, two-tailed paired t-test) (FIG. 12d, FIG. 12e). We also observed a 73% decrease in cellular migration in the CRISPR KO cells (CRISPR1 and CRISPR2 p<0.0005, two-tailed paired t-test) and more than 67% decrease in SW620 RAMS11 silenced cells (p<0.05, two-tailed paired t-test) (FIG. 2d, FIG. 2f). In addition, there was increased migration in HT29 RAMS11 overexpressing cells (FIG. 2d, FIG. 2h). Taken together, this demonstrates that RAMS11 promotes cellular invasion in CRC.

We next investigated the ability of RAMS11 to promote anchorage-independent growth as another indication of aggressive oncogenic phenotypes. Using a soft agar colony formation assay, we detected more than a 66% reduction in colony formation in the RAMS11 CRISPR KO cell lines relative to the wild-type LoVo cell line (FIG. 2i, FIG. 2j). Conversely, there was a 30% increase in colony formation in the RAMS11 overexpressing HT29 cell lines (Clone1 and Clone2 p<0.05, two-tailed paired t-test) compared with the empty vector cell line (FIG. 2i, FIG. 2k). These combined data show that decreased expression of RAMS11 in genetically modified and transient knockdown cell lines mitigates aggressive phenotypes, while overexpressing RAMS11 promotes aggressive phenotypes.

As another hallmark of aggressive phenotypes, we next assessed the effect of RAMS11 expression on cellular proliferation. We observed a 27% decrease in proliferation in our CRISPR KO cell lines (p<0.05, two-tailed paired t-test) (FIG. 12f, FIG. 12g, and ref.[10]). Taken together, our in vitro data demonstrate that RAMS11 can promote multiple oncogenic phenotypes.

Figure 13:
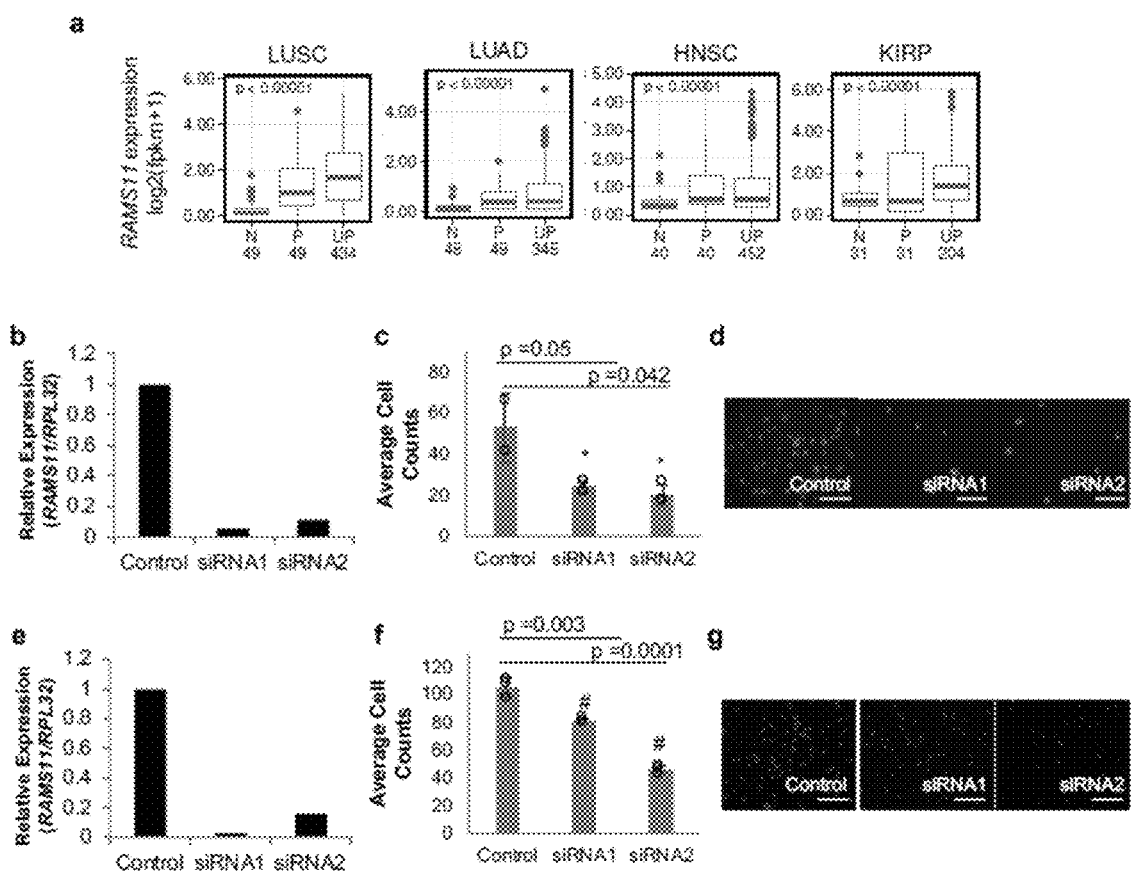
FIG. 13. RAMS11 is an onco-lncRNA that increases the invasive phenotype in cancer cell lines. (a) RAMS11 up-regulation in cancer from The Cancer Genome Atlas (TCGA). Shown are boxplots with box representing the interquartile range (IQR, 25th to 75th percentile) centered by median, whisker lines limited by 1.5xIQR away from the box, and dots representing outliers. HNSC pvalue=8.76 e−06, KIRP pvalue=9.87 e−06, LUAD pvalue=2.12 e−09, LUSC pvalue=1.05 e−17. Exact two-sided p-values were determined using a negative binomial model. Lung squamous cell carcinoma (LUSC), lung adenocarcinoma (LUAD), head and neck squamous cell carcinoma (HNSC), and kidney renal papillary cell carcinoma (KIRP). Normal (N), Primary, (P), and Unmatched primary (UP). (b) Knockdown efficiency of RAMS11 in HCC95 LUSC cell line. (c and d) Knockdown of RAMS11 with siRNAs shows a significant decrease in invasion in HCC95 cells. Control n=2, siRNA1 n=3, siRNA2 n=3, (e) Knockdown efficiency of RAMS11 in A549 LUAD cell line. (f and g) Knockdown of RAMS11 with siRNAs shows a significant decrease in invasion in A549 cells. n=3 DAPI stained cells are shown in blue. Data is presented as mean values ±s.d and analyzed by two-tailed paired t-test. Bars=25 μM. *p<0.05, #p<0.0005.

Next, we evaluated whether RAMS11 is broadly deregulated across cancer types, which would suggest a critical conserved oncogenic role in cancer progression, which we refer to as an onco-lncRNA[37]. We conducted a pan-cancer analysis of 6984 tissues comprised of matched and unmatched normal and primary tumors across 22 different cancer types studied within the TCGA. This analysis revealed that RAMS11 had elevated expression in primary tumors compared with normal tissue of origin in colorectal adenocarcinoma (p<0.00001) and four additional cancer types including: lung adenocarcinoma (p<0.00001), lung squamous cell carcinoma (p<0.00001), head and neck squamous cell carcinoma (p<0.00001), and kidney renal papillary cell carcinoma (p<0.00001) (FIG. 13a).

Last, since we found that RAMS11 is an onco-lncRNA upregulated across cancer types, we determined if RAMS11 also promoted oncogenic phenotypes in additional cancer types. Therefore, we silenced RAMS11 expression and assessed invasion in two different histologies of non-small cell lung cancer, lung squamous (HCC95), and lung adenocarcinoma (A549), cell line models. We found that silencing RAMS11 expression in both cancer cell lines caused a decrease in cellular invasion (HCC95 p<0.05; A549 p<0.005, two-tailed paired t-test) (FIG. 13b-FIG. 13g). These results indicate that increased RAMS11 expression promotes oncogenic phenotypes in multiple cancer types.

RAMS11 Promotes Tumor Growth and Metastasis In Vivo

Since our RAMS11 CRISPR KO lines had a significant decrease in cellular proliferation in vitro (FIG. 12f, FIG. 12g), we evaluated tumor growth by injecting RAMS11 CRISPR KO cells into NOD/SCID immunocompromised mice. Twenty-five days after subcutaneous injection of LoVo luciferase-tagged wild-type and our luciferase-tagged RAMS11 CRISPR KO cells we found a significant decrease (p<0.0005, two-tailed paired t-test) in both tumor volume and size in mice injected with RAMS11 CRISPR KO cells compared with wild-type cells (FIG. 3a-FIG. 3d). These results indicate that RAMS11 may indeed induce tumor formation and promote oncogenesis in vivo.

Figure 4:
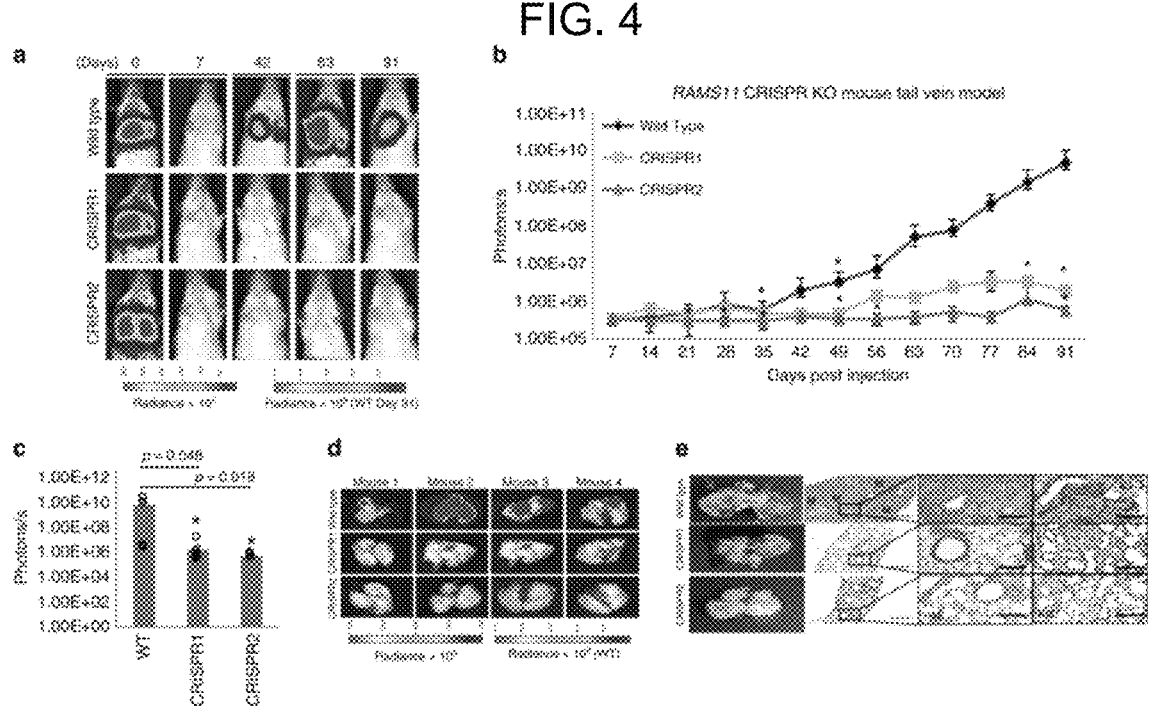
FIG. 4. RAMS11 induces lung metastasis via tail vein mouse model. (a) Representative mice and (b) quantification showing no lung metastasis in RAMS11 CRISPR KO cell-injected mouse by BLI. Day 28 CRISPR2 p=0.04, day 35 CRISPR1 p=0.02 CRISPR2 p=0.013, day 49 CRISPR1 p=0.02 CRISPR2 p=0.01 day 84 CRISPR1 p=0.05 CRISPR2 p=0.03, day 91 CRISPR1 p=0.04 CRISPR2 p=0.01. (c, d) Day 91 ex vivo mouse lungs show RAMS11 CRISPR KO cell-injected mice have decreased lung metastasis by BLI. (e) Hematoxylin and eosin stain showing metastasis (M) and Ki67 stain. Three independent tissues were stained per group. Blue bar=1 mM, black bar=25 μM. Data shown as mean±SEM and analyzed by two-tailed paired t-test, with n=12 per group repeated two times. *p<0.05.

Next, to assess the contribution of RAMS11 to cause metastasis in vivo, we used two mouse models of metastasis: a tail vein injection model to study the development of lung metastases and a hemisplenectomy model to study the development of liver metastases. For the tail vein model, we injected LoVo luciferase-tagged wild-type and our luciferase-tagged RAMS11 CRISPR KO cells into the tail vein of 5-week-old NOD/SCID mice. We monitored the mice at day 0, within 30 min to 1 h post injection, and weekly for metastasis formation with bioluminescence imaging (BLI). All mice were injected successfully showing similar luminescence levels determined by BLI at baseline day 0 (FIG. 4a). Further, images from day 7 showed no detectable signal indicating the internalization of circulating cells throughout the mouse. There was little or no lung metastasis in mice injected with RAMS11 CRISPR KO cell lines by day 35 (p=0.02, two-tailed paired t-test) as compared with wild-type cells (FIG. 4a, FIG. 4b). We continued to monitor lung metastasis for 91 days and saw significantly less lung metastasis in RAMS11 CRISPR KO cell-injected mice compared with wild-type cell-injected mice (p<0.05, two-tailed paired t-test) (FIG. 4b, FIG. 4c). We also detected less lung metastasis ex vivo in mice injected with RAMS11 CRISPR KO cells compared with mice injected with wild-type cells (FIG. 4d). In addition, extracted lungs had little to no tumors detected by hematoxylin and eosin (H&E) stain and lower levels of Ki67 staining from RAMS11 CRISPR KO cell-injected mice compared with wild-type cell-injected mice (FIG. 4e).

Figure 5:
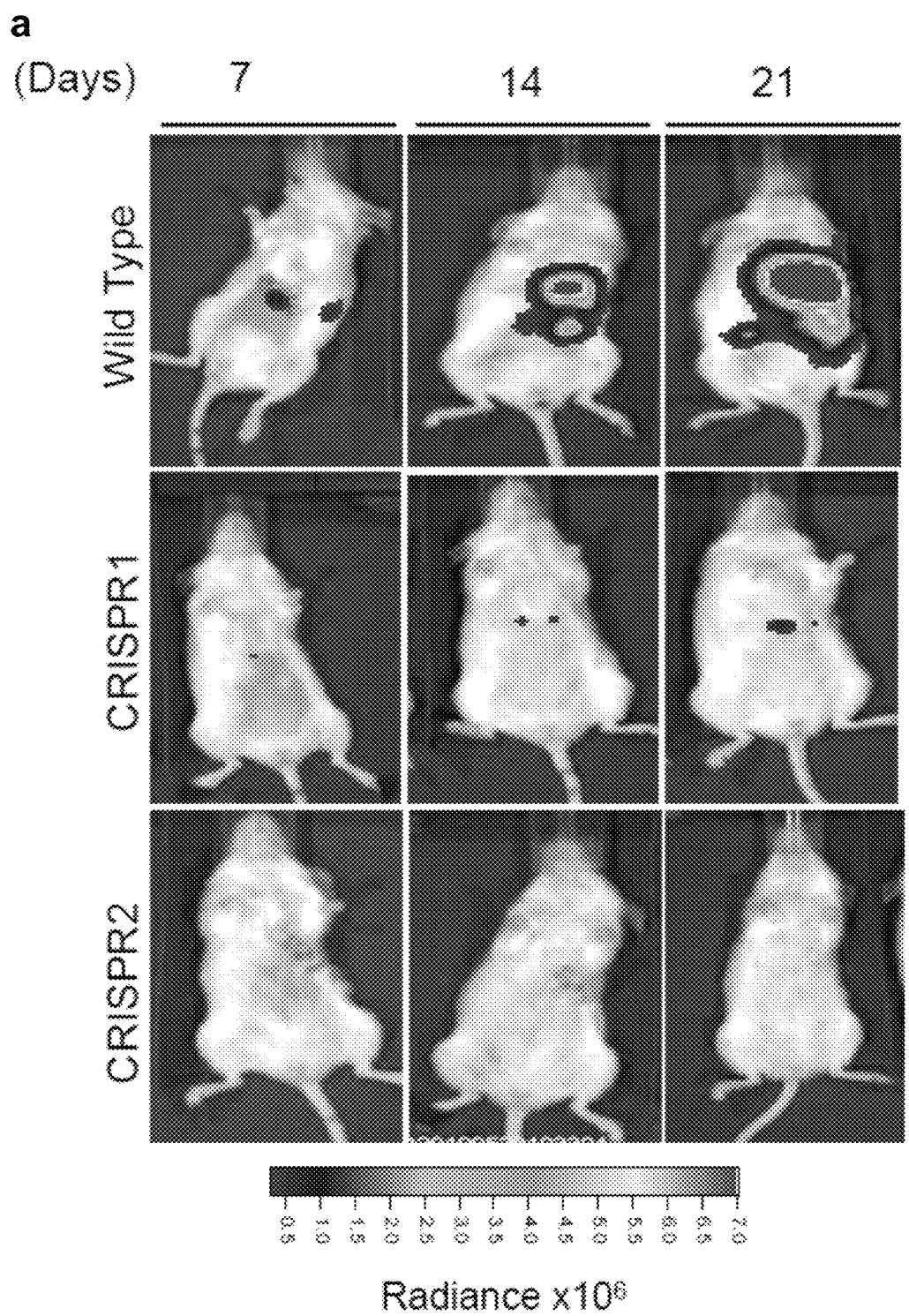
FIG. 5. RAMS11 induces liver metastasis via hemisplenectomy mouse model. (a) Representative mice showing no liver metastasis in RAMS11 CRISPR KO cell-injected mice by BLI. (b) RAMS11 CRISPR KO cell-injected mice show a significant decrease in liver metastasis by day 21. (c) Day 21 ex vivo mouse livers show decreased metastasis in RAMS11 CRISPR KO cell-injected mice by BLI. Wild-type cell-injected mice had (d) increased liver weights and (e) liver metastasis compared with CRISPR KO cell-injected mice. (f) Hematoxylin and eosin stain of livers showing metastasis (M) and levels of Ki67 stain. Three independent tissues were stained per group. White bar=10 μM, black bar=100 μM. Data shown as mean±SEM and analyzed by two-tailed paired t-test, with WT n=18, CRISPR1 n=11, CRISPR2 n=11 per group, experiment was repeated three times. *p<0.05, **p<0.005, #p<0.0005.
Figure 5:
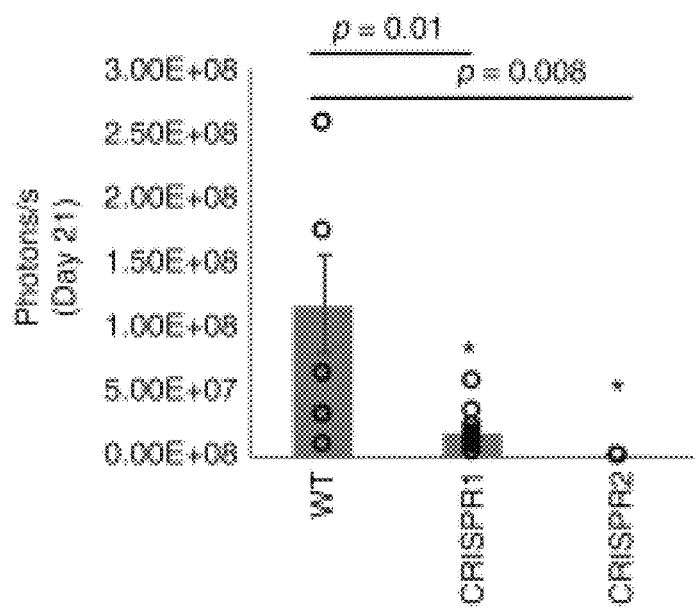
Figure 5:
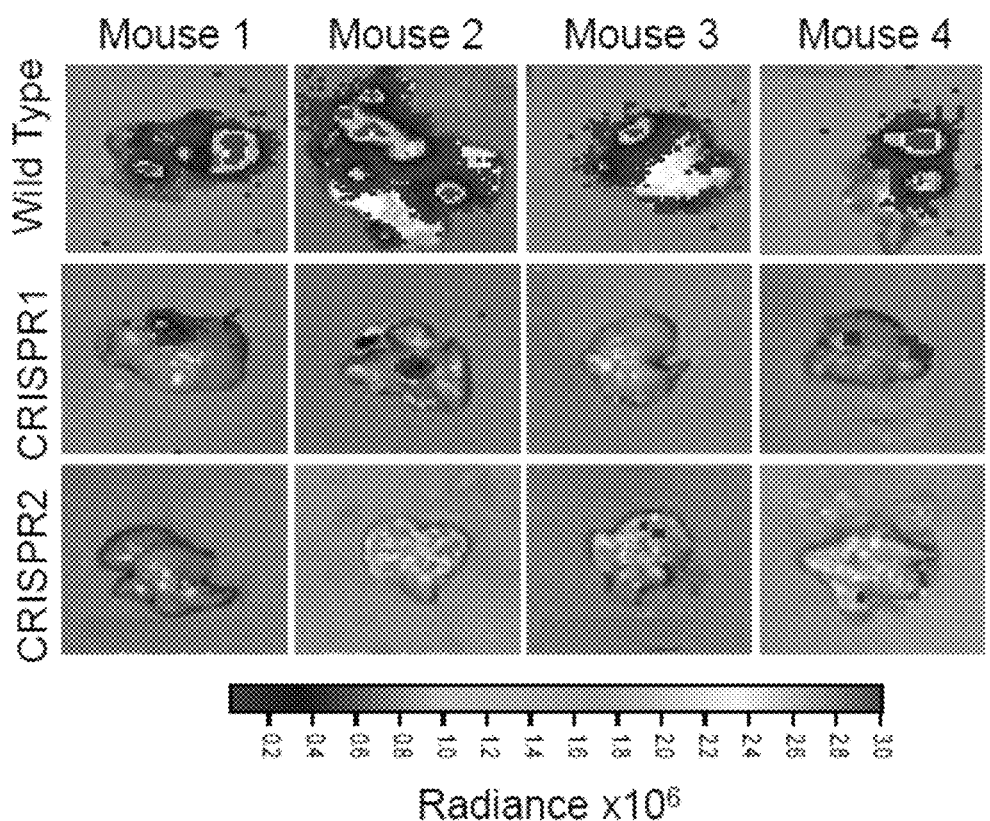
Figure 5:
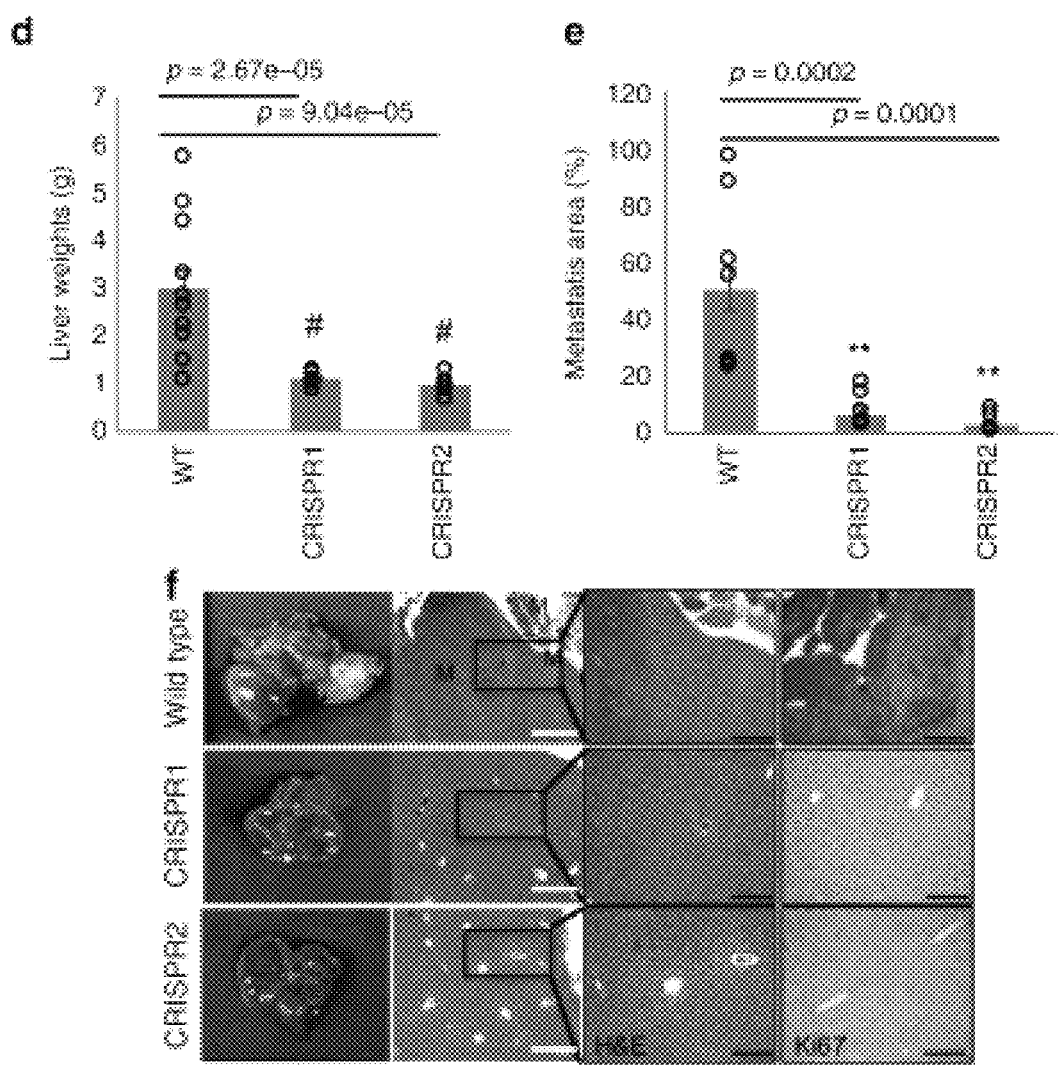

We assessed if RAMS11 promoted liver metastasis using the hemisplenectomy model. LoVo luciferase-tagged wild-type and luciferase-tagged RAMS11 CRISPR KO cells were injected into 8-week-old NGS mouse spleens[38]. We detected liver metastasis by day 7 in mice injected with wild-type cells (FIG. 5a) and detected significantly lower levels of bioluminescence in RAMS11 CRISPR KO cell-injected mice compared with wild-type cell-injected mice by Day 21 (CRISPR1 p=0.016, CRISPR2 p=0.008, two-tailed paired t-test, FIG. 5a, b). We excised all mouse livers and validated the decrease of liver metastasis (FIG. 5c), decreased liver weights (CRISPR1 p=0.0000026, CRISPR2 p=0.00069, two-tailed paired t-test, FIG. 5d), and decrease in overall liver metastasis area (CRISPR1 p=0.00021, CRISPR2 p=0.00018, two-tailed paired t-test, FIG. 5e) in RAMS11 CRISPR KO cell-injected tumors. Decreased tumor burden and proliferation in RAMS11 CRISPR KO cell livers were further determined by H&E and Ki67 staining (FIG. 5f). Overall, our cell models manipulating RAMS11 expression demonstrate the ability of RAMS11 to promote invasive phenotypes both in vitro and in vivo.

Drug Screen Reveals RAMS11 Resistance to TOP2α Inhibitors

To implicate RAMS11 in specific biological processes and establish its clinical importance, we conducted a high-throughput viability assay using 119 FDA-approved anti-cancer drugs from the NIH Developmental Therapeutics Program (Approved Oncology Drugs Set VI). The FDA-approved anticancer panel included multiple classes of drugs such as kinase inhibitors, alkylating agents, antineoplastic antibiotics, anthracycline antibiotics, and antineoplastic agents (topoisomerase inhibitors). The HT29 RAMS11 overexpressing and control cells were treated for 72 h to assess cellular viability upon drug treatment (FIG. 14a and TABLE 3). The RAMS11 overexpressing cells were resistant to nine drugs as demonstrated by a greater than three-fold increase in cellular viability when compared with the empty vector control cell line with the greatest resistance observed with gemcitabine and floxuridine (FUDR) (FIG. 14b, FIG. 14c). FUDR, a 5-FU derivative, is commonly used to treat mCRC, while gemcitabine is used in refractory mCRC[39-42]. Due to 5-FU commonly used to treat mCRC, we further determined if RAMS11 expression altered drug sensitivity in treated cells. In our RAMS11 CRISPR KO lines we found a 1.7-fold and 5.8-fold increase in drug sensitivity in CRISPR1 and CRISPR2, respectively, compared with wild-type cells (FIG. 15a). Similarly in SW620 cells with transient silencing of RAMS11, there was a greater than 1.5-fold increase in drug sensitivity in both siRNAs (siRNA1 fold >1.53, siRNA2 fold >1.59) relative to scrambled control wild-type treated cells (FIG. 15b). 5-FU, irinotecan (topoisomerase I inhibitor (TOP1)), and oxaliplatin (new-generation platinum compound) are currently used as first-line active chemotherapy options individually or in combination for patients with metastatic disease[43,44]. We did not see a significant effect of cell viability for irinotecan or oxaliplatin using our HT29 RAMS11 overexpressing cells or LoVo RAMS11 CRISPR KO cells (TABLE 3, FIG. 15c-FIG. 15e). SW620 cells with silenced RAMS11 also did not have a significant effect of cellular viability for oxaliplatin treatment, but we did detect an increase in drug sensitivity to irinotecan (siRNA1 fold >3.17 and siRNA2 fold >11.8, FIG. 15f).

TABLE 3

Viability assay results from FDA approved drug panel of RAMS11 overexpression cells.

| Drug name | Drug Class | OE1 10 uM Fold Change | 1 uM Fold Change | 0.1 uM Fold Change | OE2 10 uM Fold Change | 1 uM Fold Change | 0.1 uM Fold Change |
|---|---|---|---|---|---|---|---|
| Paclitaxel | Taxane | 3.24100167 | 3.50027339 | 2.77506701 | 3.06093163 | 3.06538572 | 2.662085213 |
| Cabazitaxel | Taxane | 2.60662677 | 3.23117632 | 2.97539492 | 2.50617126 | 2.86932597 | 2.745114104 |
| Docetaxel | Taxane | 2.89374422 | 2.99625356 | 2.83149567 | 2.86938936 | 2.84454317 | 2.725560031 |
| Omacetaxine mepesuccinate | Taxane | 1.60590132 | 1.61448881 | 1.35438473 | 1.43590685 | 1.46761356 | 1.376490637 |
| Trametinib | Kinase inhibitor | 1.97480523 | 1.73187885 | 1.34988812 | 1.88609988 | 1.64070969 | 1.213383919 |
| Dasatinib | Kinase inhibitor | 1.5183931 | 1.28867557 | 0.72421036 | 1.60691283 | 1.56706313 | 0.785167827 |
| Lapatinib | Kinase inhibitor | 1.35719128 | 1.26947982 | 1.03360199 | 1.39065368 | 1.28459077 | 1.216048865 |
| Gefitinib | Kinase inhibitor | 1.4683146 | 1.16396998 | 0.94531968 | 1.39153062 | 1.22657666 | 0.943562108 |
| Erlotinib HCl | Kinase inhibitor | 1.17931619 | 1.16853362 | 0.99583086 | 1.21451761 | 1.17160009 | 0.989930919 |
| Afatinib | Kinase Inhibitor | 1.38993449 | 1.12056298 | 1.03386575 | 1.39794937 | 1.15595552 | 1.14722466 |
| Axitinib | Kinase Inhibitor | 0.86364507 | 0.93817306 | 0.95139605 | 0.81425507 | 1.10065464 | 0.911011406 |
| Regorafenib | Kinase inhibitor | 1.15751785 | 0.94761611 | 0.93800682 | 1.14253892 | 1.09011942 | 0.9918869 |
| Ceritinib | Kinase inhibitor | 0.83038381 | 1.01538499 | 0.99229971 | 0.81948426 | 1.06772622 | 1.009084004 |
| Ibrutinib | Kinase Inhibitor | 1.31042935 | 1.09900522 | 1.01632418 | 1.30938615 | 1.04760077 | 1.065296629 |
| Bosutinib | Kinase Inhibitor | 1.47670669 | 1.01271306 | 1.04844014 | 1.60772534 | 1.0398059 | 1.021530452 |
| Cabozantinib | Kinase inhibitor | 0.99496422 | 1.01185153 | 0.97127078 | 0.87309952 | 1.0373068 | 0.957535852 |
| Imatinib | Kinase inhibitor | 0.90486651 | 0.87910595 | 0.84019119 | 0.99082631 | 0.93923453 | 0.95011165 |
| Ponatinib | Kinase inhibitor | 1.05562021 | 0.93826093 | 0.96450293 | 1.19863414 | 0.93422223 | 1.001206252 |
| Sunitinib | Kinase inhibitor | 0.23290654 | 0.88562036 | 0.83373346 | 0.57135606 | 0.91648993 | 0.914020413 |
| Vandetanib | Kinase Inhibitor | 1.18056424 | 0.81271616 | 0.90245796 | 1.14230201 | 0.91619457 | 0.971013383 |
| Pazopanib hydrochloride | Kinase Inhibitor | 0.86331146 | 0.77925354 | 0.87432082 | 0.91515726 | 0.905612 | 0.940899619 |
| Sorafenib | Kinase inhibitor | 1.02245219 | 0.81767794 | 0.8541687 | 1.01684538 | 0.89714924 | 0.895864466 |
| Nilotinib | Kinase inhibitor | 0.7378669 | 0.74900928 | 0.86786493 | 0.74624455 | 0.88803604 | 1.013127733 |
| Idelalisib | Kinase inhibitor | 0.91110675 | 0.88751598 | 0.90922657 | 0.87456213 | 0.88520941 | 0.977292378 |
| Vinblastine sulfate | Plant alkaloid | 3.68201879 | 3.40172331 | 3.19791648 | 3.81455986 | 3.41247213 | 2.825265888 |
| Vinorelbine tartrate | Plant alkaloid | 2.91287901 | 1.1939178 | 0.95676405 | 2.91346772 | 1.06675452 | 0.948097639 |
| Letrozole | Aromatase inhibitor | 0.97907454 | 0.95361807 | 0.99229507 | 0.8412015 | 1.05653297 | 0.945389567 |
| Exemestane | Aromatase inhibitor | 0.91760048 | 0.98097762 | 0.86513105 | 1.05986147 | 1.00801302 | 1.046517467 |
| Anastrozole | Aromatase inhibitor | 0.93847313 | 0.99569427 | 0.87597252 | 0.92552619 | 1.00088124 | 0.974890976 |
| Gemcitabine | Antimetabolite/ nucleoside analog | 2.39010485 | 3.42856198 | 1.76824496 | 2.49927786 | 3.02790273 | 1.506965968 |
| Floxuridine | Antimetabolite/ nucleoside analog | 2.96364371 | 2.29133758 | 1.54121802 | 3.09129455 | 2.37453555 | 1.569345585 |
| Clofarabine | Antimetabolite/ folic acid analog | 2.4728878 | 1.36083125 | 0.91407265 | 2.37527181 | 1.42090456 | 1.012179656 |
| Cytarabine hydrochloride | Antimetabolite/ nucleoside analog | 1.52423184 | 1.25385657 | 0.98252132 | 1.87627323 | 1.38110922 | 0.991694038 |
| Cladribine | Antimetabolite/ nucleoside analog | 1.94911209 | 1.32139201 | 0.87355075 | 1.85965673 | 1.32710862 | 0.935818418 |
| Decitabine | Antimetabolite/ nucleoside analog | 0.86235151 | 0.9365636 | 0.90643045 | 1.1683375 | 1.09123517 | 1.025553831 |
| Hydroxyurea | Antimetabolite | 0.97228756 | 0.96320748 | 0.94961951 | 0.96748855 | 1.07390062 | 0.987121819 |
| Fludarabine | Antimetabolite/ nucleoside analog | 1.05574373 | 0.99210501 | 0.86896128 | 1.07256043 | 1.06853143 | 0.97296591 |
| Mercaptopurine | Antimetabolite/ nucleoside analog | 1.00603374 | 0.9981663 | 0.96399691 | 1.05006988 | 1.02915921 | 0.941239772 |
| Nelarabine | Antimetabolite | 0.95548558 | 1.03291769 | 0.98188176 | 0.97013718 | 1.0067901 | 0.946246727 |
| Pentostatin | Antimetabolite/ nucleoside analog | 0.86584621 | 0.95016122 | 0.93122136 | 1.07817461 | 0.97768192 | 0.928653469 |
| Fluorouracil | Antimetabolite/ nucleoside analog | 0.98912 | 0.95532474 | 0.9855589 | 1.02121612 | 0.94169325 | 0.940646587 |
| Thioguanine | Antimetabolite | 0.9702018 | 0.92883787 | 0.94227499 | 1.00988237 | 0.8724032 | 0.899480944 |
| Capecitabine | Antimetabolite | 0.96093202 | 0.79394639 | 1.29143026 | 1.16597498 | 0.80928009 | 1.102307072 |
| Methotrexate | Antimetabolite/ folic acid analog | 1.19650523 | 0.55775907 | 0.91988034 | 1.13675626 | 0.57523305 | 0.914293753 |
| Triethylenemelamine | Alkylating agent | 1.28748847 | 1.23776135 | 0.99737092 | 1.29530357 | 1.28406202 | 1.012994849 |
| Chlorambucil | Alkylating agent | 1.06433247 | 1.16395597 | 0.95312874 | 0.91734001 | 1.14365362 | 0.985881887 |
| Lomustine | Alkylating agent | 1.0269215 | 1.02995633 | 0.99685187 | 0.96457982 | 1.11094994 | 0.990953055 |
| Carmustine | Alkylating agent | 0.869624 | 0.98644215 | 1.00704099 | 1.0396557 | 1.07904166 | 1.005237932 |
| Melphalan | Alkylating agent | 0.97820553 | 1.00609296 | 0.92137022 | 0.99415911 | 1.0683883 | 0.947893033 |
| Ifosfamide | Alkylating agent | 0.97241823 | 1.02451627 | 0.91665329 | 1.05817918 | 1.05510162 | 0.922637768 |
| Uracil mustard | Alkylating agent | 0.83061497 | 1.01956314 | 0.97052419 | 0.96468249 | 1.04848324 | 0.931997741 |
| Procarbazine | Alkylating agent | 0.98251442 | 1.04227372 | 1.00315434 | 0.9303314 | 1.04627249 | 0.932777031 |
| Temozolomide | Alkylating agent | 0.87770446 | 0.94674253 | 0.93437733 | 0.91984469 | 1.03212616 | 0.89754128 |
| Dacarbazine | Alkylating agent | 0.98303113 | 0.98768036 | 1.07779243 | 0.97936126 | 1.02761133 | 1.084397328 |
| Cyclophosphamide | Alkylating agent | 0.8570271 | 0.96322455 | 0.98081969 | 0.89898225 | 1.01925082 | 0.880970518 |
| Mechlorethamine hydrochloride | Alkylating agent | 0.77170835 | 0.96513502 | 0.92881065 | 0.8646484 | 0.95922109 | 0.944924936 |
| Pipobroman | Alkylating agent | 0.99180867 | 0.98381386 | 0.94133778 | 0.89489081 | 0.94377889 | 0.943168109 |

TABLE 3-continued

Viability assay results from FDA approved drug panel of RAMS11 overexpression cells.

| Drug name | Drug Class | OE1 10 uM Fold Change | 1 uM Fold Change | 0.1 uM Fold Change | OE2 10 uM Fold Change | 1 uM Fold Change | 0.1 uM Fold Change |
| --- | --- | --- | --- | --- | --- | --- | --- |
| Thiotepa | Alkylating agent | 0.79075487 | 0.98256701 | 0.94006066 | 0.96944821 | 0.94333141 | 0.881741982 |
| Busulfan | Alkylating agent | 0.84476333 | 0.93652265 | 1.00119124 | 0.87102626 | 0.93685291 | 0.976989353 |
| Bendamustine hydrochloride | alkylating agent | 0.93496611 | 0.97254558 | 0.8888121 | 0.89897319 | 0.90364637 | 1.009560873 |
| Mitomycin | Antineoplastic antibiotic | 2.41640131 | 1.5471685 | 0.96675187 | 2.00386037 | 1.6240776 | 1.006174581 |
| Dactinomycin | Antineoplastic antibiotic | 2.71890413 | 1.55211982 | 1.51262717 | 2.49750988 | 1.47540505 | 1.416542095 |
| Plicamycin | Antineoplastic antibiotic | 2.0935077 | 1.18049821 | 1.20574502 | 1.89024509 | 1.09842623 | 1.153949199 |
| Bleomycin | Antineoplastic antibiotic | 1.02536257 | 1.03853971 | 0.92099163 | 1.07100756 | 1.07366137 | 0.96002561 |
| Streptozocin | Antineoplastic antibiotic | 0.90500557 | 1.01093447 | 1.05991343 | 0.99548665 | 1.03619063 | 0.972877201 |
| Oxaliplatin | Platinum-based alkylating agent | 1.33017213 | 0.98805853 | 0.91274044 | 1.42669331 | 1.1020411 | 0.967115657 |
| Carboplatin | Platinum-based alkylating agent | 1.10331659 | 1.04703644 | 1.01631865 | 0.99685005 | 1.07437529 | 0.969683256 |
| Cisplatin | Platinum-based alkylating agent | 0.94061014 | 0.92766647 | 1.0228064 | 0.99607059 | 0.97820128 | 0.958310331 |
| Estramustine | Hormone analog | 1.03438094 | 1.10459265 | 0.97000834 | 1.02504289 | 1.22335058 | 0.950996978 |
| Enzalutamide | Hormone antagonist/SERM | 1.08755775 | 1.0807201 | 1.04327711 | 1.1003533 | 1.15191358 | 1.021690366 |
| Fulvestrant | Hormone antagonist/SERM | 1.13540481 | 1.03655242 | 1.04805738 | 1.03596278 | 1.08866748 | 1.088236829 |
| Tamoxifen Citrate | SERM | 1.07730893 | 1.14390213 | 1.12696006 | 1.05865108 | 1.08027418 | 1.097067128 |
| Mitotane | Hormone analog | 0.91050812 | 0.9667493 | 0.81852274 | 0.98704157 | 0.97143009 | 0.948203879 |
| Megestrol acetate | Hormone analog | 0.99610994 | 1.03383022 | 0.89218562 | 0.9015782 | 0.95778585 | 0.894868256 |
| Raloxifene | SERM | 0.90674656 | 0.92435098 | 0.94565051 | 0.96707327 | 0.9281808 | 0.94014746 |
| Topotecan HCL | Other antineoplastic agents | 3.38863524 | 2.22534654 | 1.11049767 | 2.76280587 | 2.1266037 | 1.018066084 |
| Daunorubicin HCl | Anthracycline antineoplastic antibiotic | 3.76062763 | 2.25836921 | 1.10335465 | 3.72627603 | 2.09823912 | 1.083542261 |
| Doxorubicin HCl | Anthracycline antineoplastic antibiotic | 2.43819224 | 1.97254317 | 1.11330716 | 2.40326415 | 1.9386564 | 1.165208183 |
| Epirubicin hydrochloride | Anthracycline antineoplastic antibiotic | 2.18951306 | 1.82166256 | 1.02464111 | 1.99880554 | 1.86089961 | 1.022825631 |
| Idarubicin hydrochloride | Topoisomerase II inhibitor | 3.60276208 | 1.72980782 | 1.36457694 | 3.69570802 | 1.62342782 | 1.572972362 |
| Mitoxantrone | Anthracenedione antineoplastic antibiotic | 1.37465059 | 1.45099844 | 1.14523362 | 1.50815824 | 1.43176515 | 1.104994194 |
| Teniopside | Plant alkaloid | 2.28751336 | 1.32732648 | 1.0379586 | 2.26120381 | 1.34891381 | 0.965663283 |
| Valrubicin | Anthracycline antineoplastic antibiotic | 1.86281171 | 1.16317302 | 0.96449281 | 1.79216326 | 1.21331115 | 0.916566273 |
| Etopside | Plant alkaloid | 1.16137913 | 1.07278015 | 1.14411555 | 1.19630571 | 0.99921073 | 1.130242004 |
| Irinotecan HCl | Other antineoplastic agents | 1.15070958 | 0.96076872 | 0.91977433 | 1.06767371 | 0.97110954 | 0.968247063 |
| Romidepsin | Other | 4.42717109 | 5.32700934 | 6.24279139 | 4.69706018 | 5.57714771 | 6.210870969 |
| Ixabepilone | epothilone antineoplastic | 1.72155378 | 1.94255323 | 1.65679743 | 2.05612237 | 2.01711163 | 1.773077753 |
| Carfilzomib | Other | 1.62520067 | 2.10007406 | 3.31984603 | 1.34266371 | 1.65419519 | 2.675124606 |
| Tretinoin | Retinoid | 1.14233688 | 1.22644259 | 1.16107517 | 1.33563032 | 1.3730709 | 1.06770287 |
| Plerixafor | Other | 1.05717863 | 1.15208185 | 0.98663797 | 1.06242319 | 1.20776899 | 1.085483039 |
| Belinostat | Other | 1.03546911 | 1.20906559 | 0.91382882 | 1.00556518 | 1.19174014 | 1.07253353 |
| Vorinostat | Synthetic hydroxamic acid deriv | 1.60438226 | 0.89483382 | 1.12329463 | 1.35574913 | 1.1591591 | 1.067761805 |
| Imiquimod | Other | 1.02967039 | 1.1006894 | 1.04841596 | 0.97516281 | 1.13818569 | 1.037375747 |
| Crizotinib | Other | 0.91269192 | 1.07029488 | 0.9595248 | 0.85621375 | 1.0930831 | 0.980622837 |
| Amifostine | Other | 1.06296016 | 1.02425454 | 0.95386451 | 1.1667987 | 1.06348287 | 0.990004872 |
| Aminolevulinic Acid | Other | 1.02230005 | 0.96545662 | 0.88034187 | 0.96132532 | 1.05845236 | 0.914015968 |
| Zoledronic acid | Other | 1.00969816 | 0.99106582 | 0.94938888 | 1.08228187 | 1.0554362 | 0.959549824 |
| Arsenic trioxide | Antineoplastic antibiotic | 0.8820536 | 0.96966707 | 0.96827719 | 1.11455712 | 1.05486579 | 1.014843994 |
| Azacitidine | Other | 0.93666039 | 1.09803313 | 1.04952702 | 0.90493462 | 1.05362959 | 1.089326684 |
| Dexrazoxane | Other | 0.86882267 | 0.98135422 | 0.95526379 | 1.1190371 | 1.04865912 | 0.941059398 |
| Abiraterone | Other | 1.00134798 | 0.99970578 | 0.95030619 | 0.98787695 | 1.04285082 | 1.008307672 |
| Lenalidomide | Other | 0.96639176 | 1.0213999 | 0.96586366 | 0.89021231 | 1.00911612 | 0.911497277 |
| Thalidomide | Other | 0.9064249 | 0.98778261 | 0.92505222 | 1.0738417 | 1.00021377 | 0.899471594 |
| Pralatrexate | Other | 1.03376965 | 0.92156915 | 0.74048859 | 1.11909353 | 0.9780878 | 0.857884424 |
| Altretamine | Other | 0.84504032 | 0.91046443 | 0.94902406 | 0.91708549 | 0.96723178 | 0.929850016 |

TABLE 3-continued

Viability assay results from FDA approved drug panel of RAMS11 overexpression cells.

| Drug name | Drug Class | OE1 10 uM Fold Change | 1 uM Fold Change | 0.1 uM Fold Change | OE2 10 uM Fold Change | 1 uM Fold Change | 0.1 uM Fold Change |
|---|---|---|---|---|---|---|---|
| Celecoxib | Other | 0.97971545 | 0.92280325 | 0.87674265 | 0.98479942 | 0.96279102 | 0.947964413 |
| Methoxsalen | Other | 0.78832681 | 0.97102616 | 0.9520623 | 0.94055892 | 0.9485286 | 0.888757326 |
| Pemetrexed disodium salt | Other | 1.88608274 | 0.94239742 | 0.91182053 | 1.93269264 | 0.94553117 | 0.995276345 |
| Pomalidomide | Other | 0.90135742 | 0.95088982 | 0.93345694 | 0.93298477 | 0.94327747 | 0.944387454 |
| Allopurinol | Other | 0.77602927 | 0.90421748 | 0.86817334 | 0.86477525 | 0.86352329 | 0.900241777 |
| Vismodegib | Other | 0.94209676 | 0.91336932 | 0.84164343 | 0.89762846 | 0.8459908 | 0.97517576 |
| Bortezomib | Antineoplastic antibiotic | 1.15213447 | 1.05904792 | 0.60152006 | 0.99677437 | 0.80629947 | 0.503484805 |
| Dabrafenib mesylate | Other | 0.91197252 | 0.8383459 | 0.7922534 | 0.91300524 | 0.80076725 | 0.773276026 |
| Everolimus | macrocyclic/ immunosuppressant | 0.68626743 | 0.74739838 | 0.64185748 | 0.72101945 | 0.7942927 | 0.648405025 |
| Rapamycin | macrocyclic/ immunosuppressant | 0.7221986 | 0.74028372 | 0.70034786 | 0.75751551 | 0.77200333 | 0.623216623 |
| Temsirolimus | Other | 0.68614183 | 0.67334264 | 0.7058819 | 0.6929901 | 0.73017449 | 0.681638928 |
| Vemurafenib | Other | 0.56903682 | 0.43806786 | 0.69205711 | 0.61441064 | 0.5468306 | 0.761994166 |
| Olaparib | Other | 1.00049169 | 0.90608956 | 0.81621046 | 0.97334073 | 0.95196642 | 0.90348231 |

Figure 6:
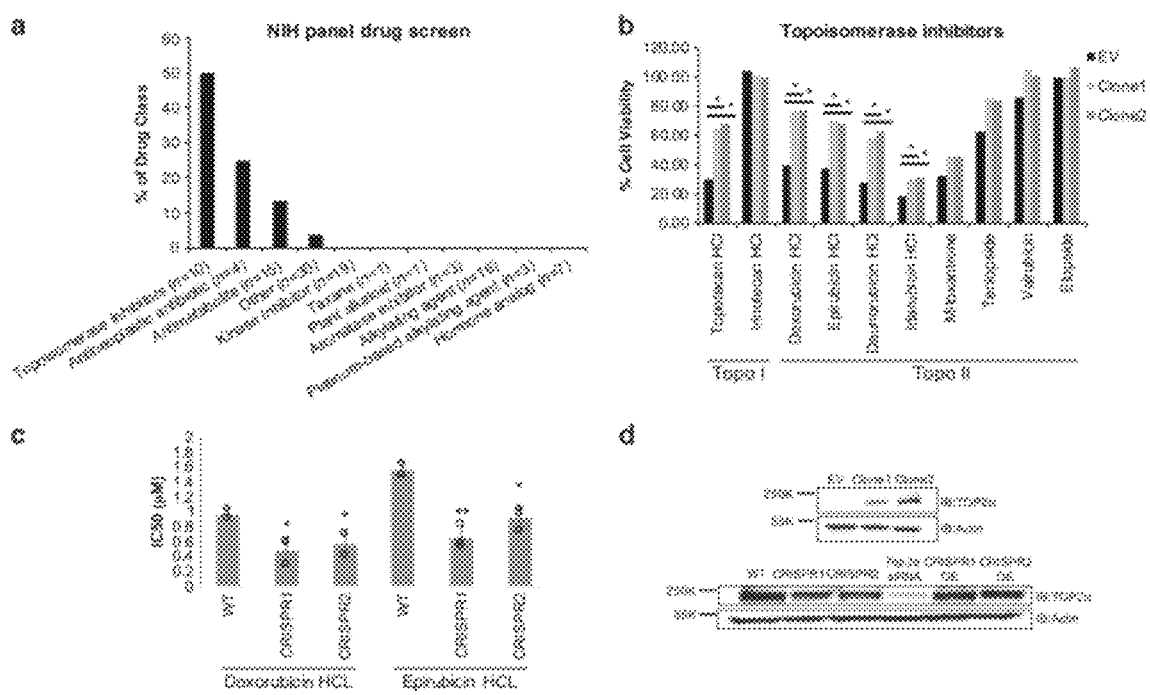
FIG. 6. RAMS11 expression alters sensitivity to topoisomerase inhibitors. (a) Cell viability assay comparing HT29 empty vector cells with RAMS11 overexpressing cell lines showing significant resistance to various drug classes. (b) RAMS11 overexpressing cells have increased cell viability compared with empty vector cells in five of ten topoisomerase (Topo) inhibitors. (c) $IC_{50}$ values of RAMS11 CRISPR KO cell lines (n=3) with decreased viability to doxorubicin hydrochloride (HCl) and epirubicin HCl drug treatments. (d) Protein expression of Top2α in (top) RAMS11 overexpressing cell lines and (bottom) CRISPR KO cell lines, TOP2α siRNA control cells, and CRISPR cell lines overexpressing (OE) RAMS11. Band intensities were quantified from the digital image in ImageJ and are shown normalized to the empty vector or wild-type lane for each target. Samples derived from the same experiment and blots were processed in parallel. All data are presented as mean values ±s.d. Experiments repeated three times. *Fold change >1.5.

Interestingly, half of the topoisomerase inhibitors assessed caused at least a two-fold increase in drug resistance in the HT29 RAMS11 overexpressing cells including the TOP1 topotecan hydrochloride (HCl) and four TOP2α inhibitors (doxorubicin HCl, epirubicin HCl, daunorubicin HCl, and idarubicin HCl (FIG. 6a, FIG. 6b). To further support our observation that RAMS11 overexpression promoted resistance to topoisomerase inhibitors, we narrowed our focus on clinically relevant drugs that selectively target the DNA topoisomerase TOP2α, doxorubicin and epirubicin. Measuring cellular viability in LoVo RAMS11 CRISPR KO cells we showed a 1.5-fold increase in drug sensitivity with 0.5 µM doxorubicin or 0.7 µM epirubicin treatment compared with wild-type treated cells ($p<0.05$, two-tailed paired t-test, FIG. 6c).

Figure 16:
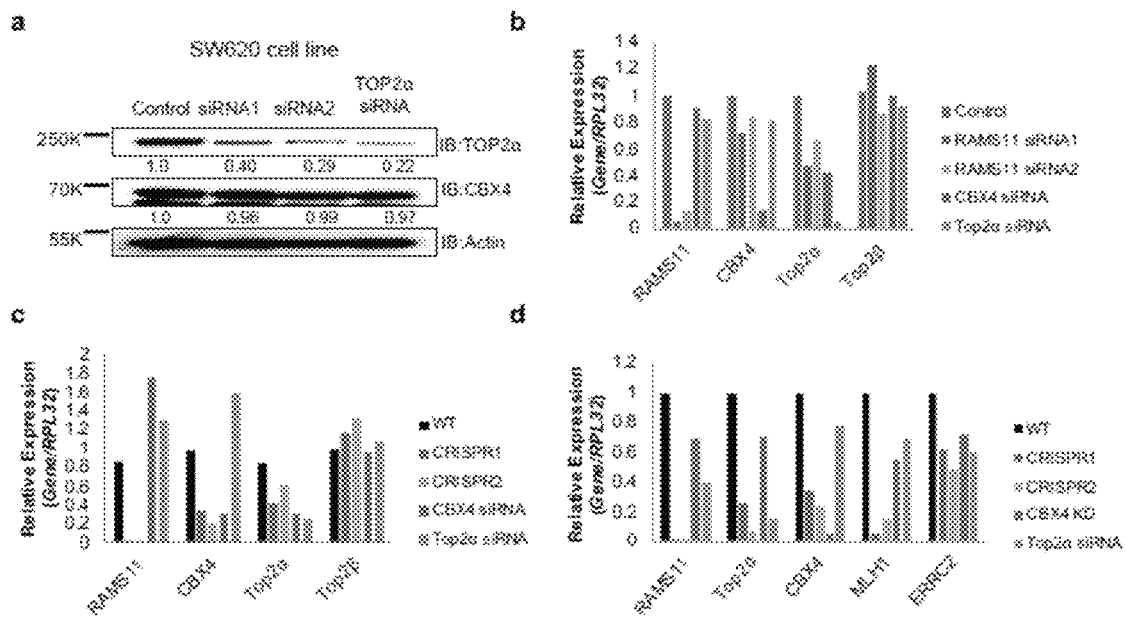
FIG. 16. RAMS11 regulation of Top2α expression. (a) Protein expression of TOP2α and CBX4 in SW620 RAMS11 silenced cells. Band intensities were quantified from the digital image in ImageJ and are shown normalized to the Wild Type or control lane for each target. Samples derived from the same experiment and blots were processed in parallel. mRNA expression of RAMS11, CBX4, TOP2α, and TOP2β in (b) SW620 RAMS11 silenced cells and (c) LoVo CRISPR KO cells. (d) Decrease in expression of TOP2α downstream genes with silenced RAMS11, TOP2α, or CBX4. Experiments repeated two times.

To further support our drug panel findings, we evaluated whether RAMS11 regulated TOP2α protein expression. We observed that RAMS11 overexpressing cell lines had elevated TOP2α protein expression, whereas our CRISPR KO cells displayed a decrease in TOP2α protein levels (FIG. 6d). The decrease in TOP2α expression in our CRISPR KO cells was rescued by re-introducing RAMS11 expression in these cells (FIG. 6d). Transient silencing of RAMS11 in SW620 cells also decreased TOP2α protein and mRNA levels relative to our scrambled control (FIG. 16a, FIG. 16b). To demonstrate the specificity of RAMS11 regulation of TOP2α, we confirmed there was only a decrease of TOP2α mRNA expression by making primers specifically targeting TOP2α and not TOP2β in the LoVo CRISPR KO and SW620 silenced cell lines (FIG. 16b, FIG. 16c). Lastly, we assessed downstream targets of TOP2α in our CRISPR KO cell lines and observed a decrease in MLH1 and ERCC2 mRNA levels supporting RAMS11 regulation of TOP2α (FIG. 16d). Overall, our high-throughput drug panel established that RAMS11 expression impacted cellular sensitivity to topoisomerase inhibitors, specifically inhibitors targeting TOP2α, which led to the discovery that RAMS11 overexpression increased TOP2α protein expression in colon cancer cell lines. These data highlight the potential for RAMS11 expression to serve as an important biomarker to select mCRC patients that may potentially benefit from topoisomerase inhibitor treatment.

RAMS11 Binds to Chromobox Protein 4 (CBX4) to Regulate TOP2α

Figure 7:
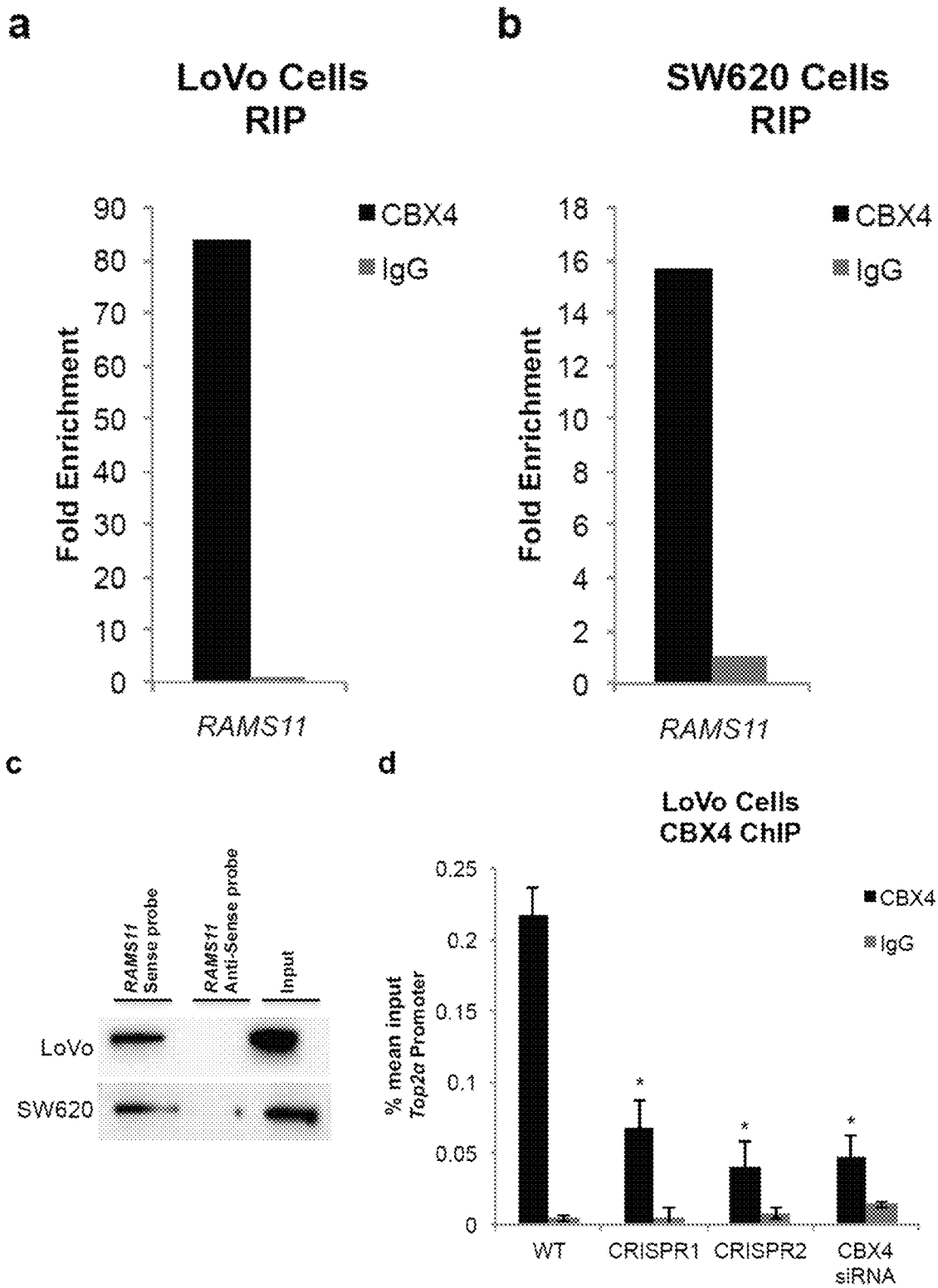
FIG. 7. RAMS11 binds to chromobox 4 (CBX4) to regulate expression of Top2α mRNA and protein. RNA immunoprecipitation (RIP) shows binding of RAMS11 to CBX4 and not negative control IgG in (a) LoVo and (b) SW620 cells. (c) RNA pull down of 5-Bromo-UTP full-length RAMS11 probe showing binding of CBX4 by Western blot in LoVo and SW620 cells. (d-g) Decreased binding of CBX4 and active histone mark H3K4me3 at TOP2α promoter with silenced RAMS11 expression in chromatin immunoprecipitation (ChIP) assay. IgG n=2, CBX4 n>3, H3K4me3 n>2. (h) RIP showing increased binding of RAMS11 to CBX4 in HT29 RAMS11 overexpressing cells. (i, j) ChIP of CBX4 and H3K4me3 shows increased binding to TOP2α promoter in HT29 RAMS11 overexpressing cells. IgG n=3, CBX4 n=3, H3K4me3 n=2. (k, l) ChIP of CBX4 and H3K4me3 in CRISPR KO cells with RAMS11 overexpression (OE) rescue at TOP2α promoter. IgG n=2, CBX4 n=2, H3K4me3 n=3. (m) Protein expression of TOP2α and CBX4 in LoVo (top) and SW620 cell lines (bottom). Band intensities were quantified from the digital image in ImageJ and are shown normalized to the wild-type lane for each target. Samples derived from the same experiment and blots were processed in parallel. Fold change normalized expression to actin is shown below gel. All data are presented as mean values ±s.d, analyzed by two-tailed paired t-test. Experiments repeated more than two times. *p<0.05 **p>0.005, #p<0.0005. (n) RNA pull down of truncated RAMS11 fragments. Top, RAMS11 5-exon transcript and four truncated RAMS11 fragments. Bottom, CBX4 western blot from RNA pull down with input, full length, and four truncated RAMS11 fragments showing interaction at 600-959 and no binding to SNRP70 (negative control).
Figure 7:
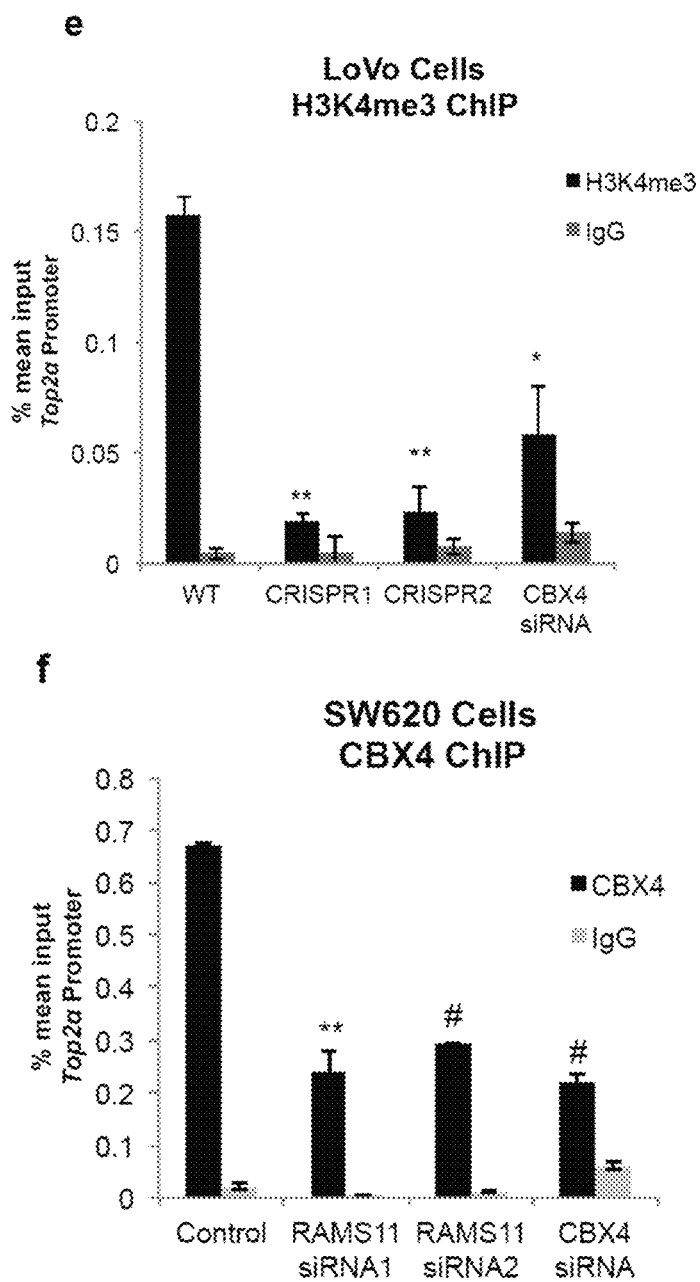
Figure 7:
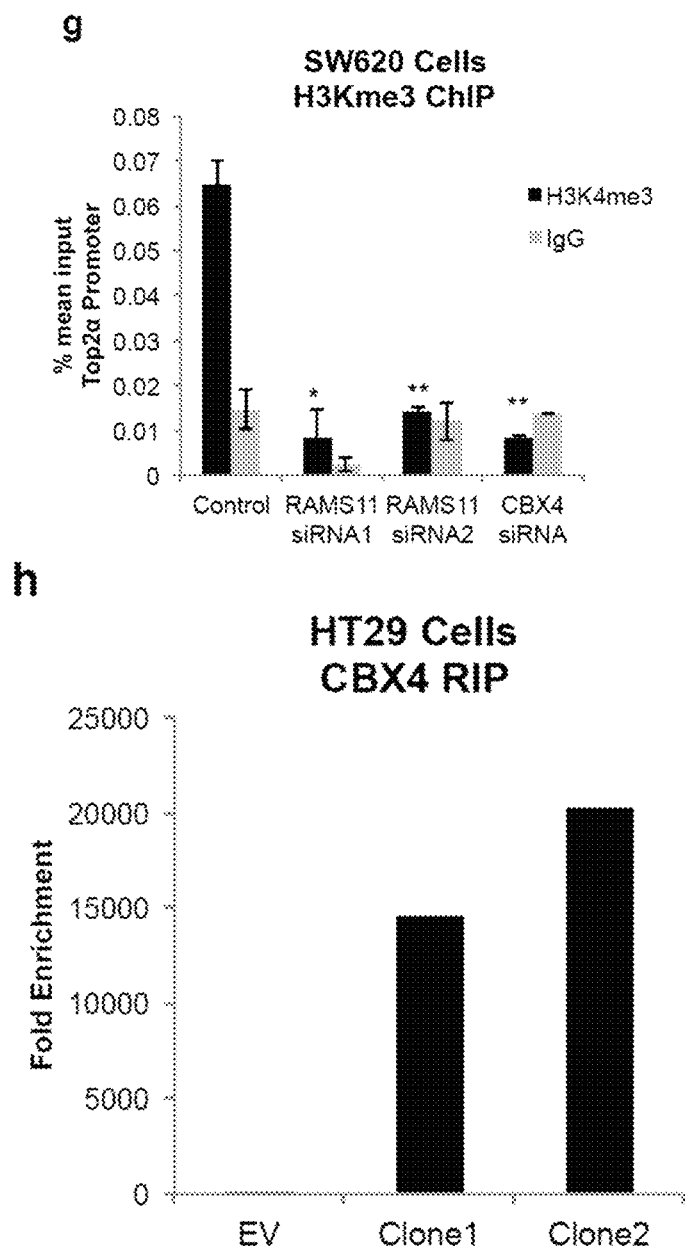
Figure 7:
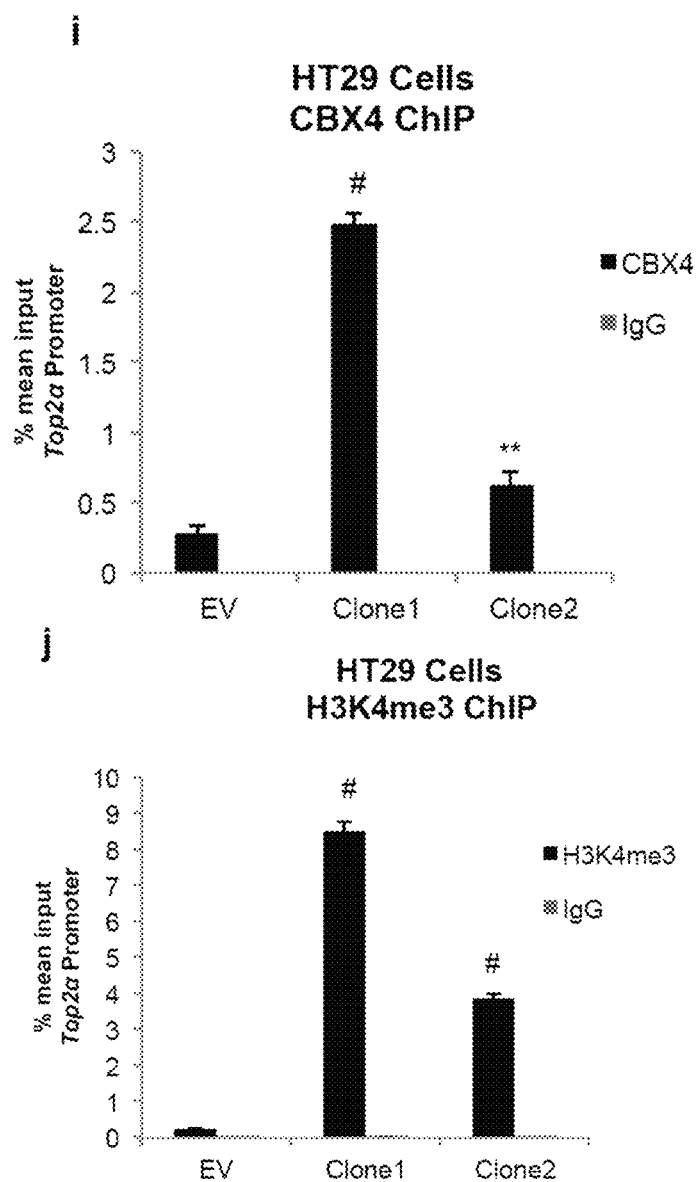
Figure 7:
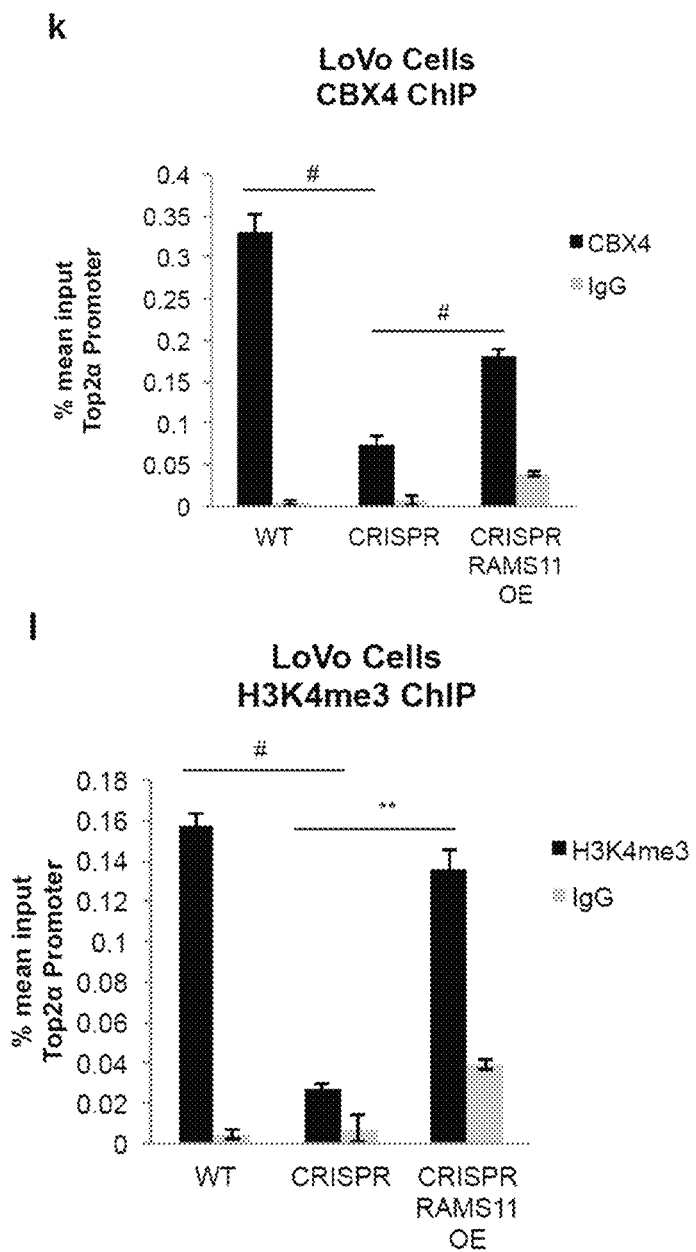
Figure 7:
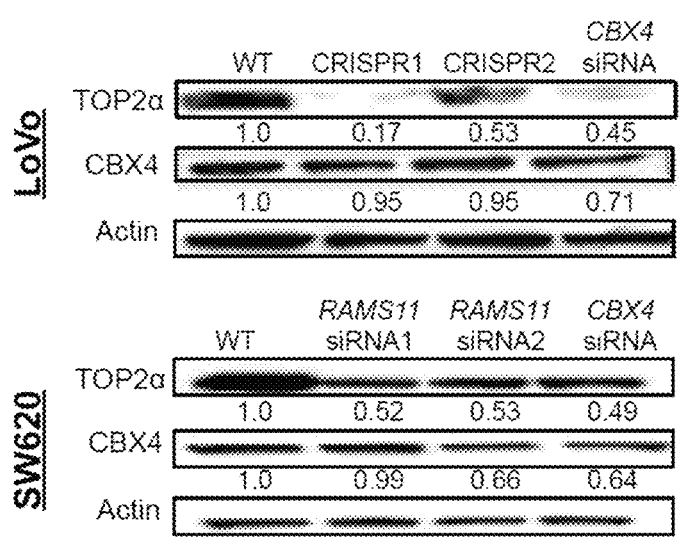
Figure 7:
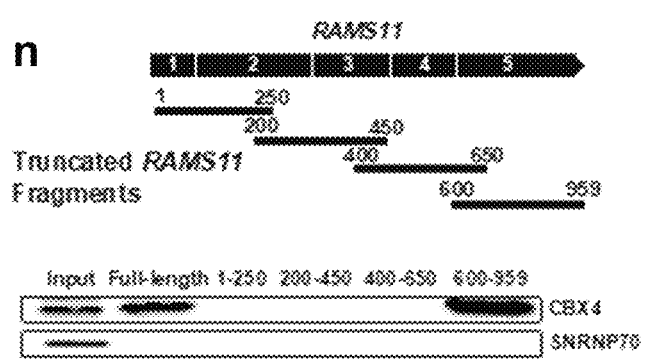
Figure 17:
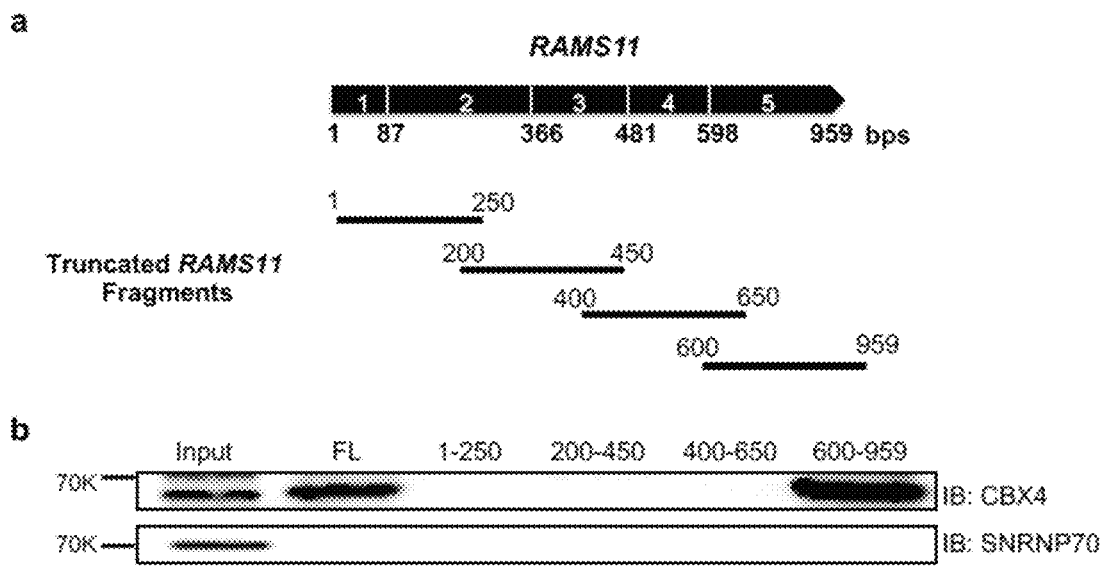
FIG. 17. RNA pull down of truncated RAMS11 fragments shows nucleotides 600-959 binding to CBX4. (a) RAMS11 five-exon transcript (top) and four created truncated RAMS11 fragments. (b) Western blot of CBX4 of RNA pull down with input, full length (FL) and four truncated RAMS11 fragments showing interaction at 600-959 and no binding to SNRP70 negative control. Samples derived from the same experiment and blots were processed in parallel. Experiments repeated two times.

Due to the nuclear localization of RAMS11 we hypothesized that it may transcriptionally regulate TOP2α expression to increase protein levels and promote topoisomerase resistance. Notably, a recent study found that CBX4 bound to the promoter of Top2α[45]. Since CBX4 is known to possess both activation and repressive activities[46,47], and has been found to interact with lncRNAs[47,48], we hypothesized that it could interact with RAMS11 and transcriptionally regulate TOP2α expression through interaction with CBX4. We found an 83-fold and 16-fold enrichment of RAMS11 bound to CBX4 in LoVo and SW620 cells, respectively, as determined by an RNA immunoprecipitation (RIP) coupled with qPCR (FIG. 7a, FIG. 7b). To orthogonally validate these findings, we conducted a RNA pull-down assay utilizing a 5' Bromo-UTP full-length RAMS11 sense labeled probe and a negative control antisense probe to pull-down proteins that may be bound to RAMS11. We found that the RAMS11 sense probe was bound to CBX4 protein compared with the antisense probe (FIG. 7c) by Western blot of nuclear lysates. To identify regions of RAMS11 that bind to CBX4, we conducted in vitro RNA pulldown in LoVo cells. Using four truncated RAMS11 fragments (FIG. 7n), we confirmed full length (FL) RAMS11 binds to CBX4 and that nucleotides 600-959 of RAMS11 interact with CBX4 protein. In order to identify the regions of RAMS11 that bind to CBX4, we conducted in vitro RNA pull down in the LoVo cell line using four truncated RAMS11 fragments (FIG. 17a). We re-validated our previous findings that full-length RAMS11 binds to CBX4 and revealed that nucleotides 600-959 of RAMS11 interact with CBX4 protein (FIG. 17b). These orthogonal methods support RAMS11 binding to CBX4 protein. Collectively, these data support RAMS11-dependent CBX4 binding to the TOP2α promoter.

Figure 8:
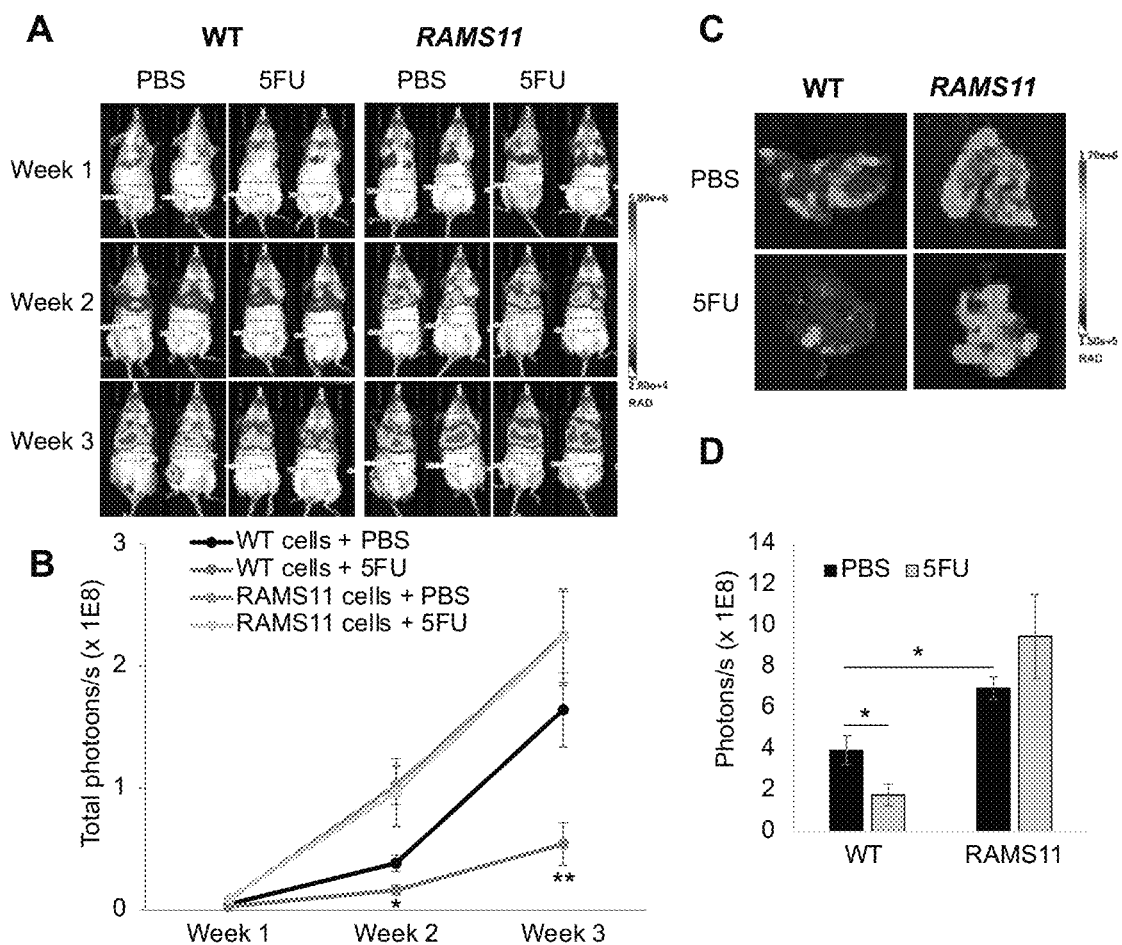
FIG. 8. Overexpression of RAMS11 causes resistance to 5FU treatment in vivo. Representative BLI images (a) and quantification (b) of mice injected with 1e6 wildtype (WT) or RAMS11-overexpressing (RAMS11) HT29 cells via tail vein. Representative BLI images (c) and quantification (d) of ex vivo lungs at week 3. Mice were treated with PBS or 50 mg/kg fluorouracil (5FU). *p<0.05 ** p<0.01.
Figure 18:
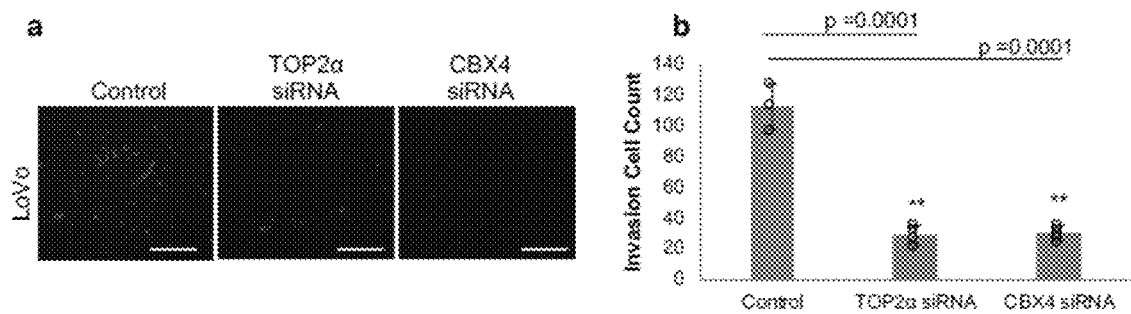
FIG. 18. TOP2α and CBX4 promote oncogenic phenotypes. (a) Transwell images of invading DAPI-stained LoVo cells with silenced TOP2α or CBX4. (b) Quantification of transwell assay. Data is presented as mean values ±s.d, analyzed by two-tailed paired t-test and repeated three times. Bars=25 μM. ** p<0.005.

We next evaluated if CBX4 interacts with the TOP2α promoter and whether this was dependent on RAMS11 expression. Binding of CBX4 to the promoter of TOP2α was confirmed by chromatin immunoprecipitation (ChIP) coupled with qPCR in LoVo colon cancer cells. Silencing CBX4 led to a 78% decrease in CBX4 occupancy at the TOP2α promoter in LoVo cells ($p=0.021$, two-tailed paired t-test, FIG. 7d). Further, we demonstrated this binding is dependent on RAMS11 expression since there was a greater than 68% decrease in CBX4 occupancy in the TOP2α promoter in our RAMS11 CRISPR KO models (p<0.005, two-tailed paired t-test, FIG. 7d). We also observed a decrease in tri-methylation of lysine 4 on the Histone H3 protein subunit (H3K4me3), a modification commonly associated with active transcription, in CBX4 siRNA treated cells and our RAMS11 CRISPR KO models (CRISPR1 p=0.001 and CRISPR2 p=0.0008, two-tailed paired t-test, FIG. 7e). Decreased CBX4 occupancy and H3K4me3 at the TOP2α promoter was further confirmed in the SW620 cell line with transiently silenced CBX4 or RAMS11 (CBX4 p=0.004, RAMS11 siRNA p<0.05, two-tailed paired t-test, FIG. 7f, FIG. 7g). In addition to demonstrating endogenous binding of RAMS11 to CBX4 in LoVo and SW620 cells, we found more than 15000-fold enrichment of CBX4 binding to RAMS11 in our HT29 RAMS11 overexpressing cells compared with empty vector (FIG. 7h). In addition, the HT29 RAMS11 overexpressing cells had increased occupancy of CBX4 (p=0.0005 and p=0.004, two-tailed paired t-test) and increased occupancy of H3K4me3 (p=0.01 and p=0.001, two-tailed paired t-test) at the TOP2α promoter (FIG. 7i, FIG. 7j). Further, we rescued CBX4 (FIG. 7k) and H3K4me3 (p=0.005, two-tailed paired t-test, FIG. 7l) occupancy by re-introducing RAMS11 expression into the LoVo CRISPR KO cells. The decrease in TOP2α protein expression was confirmed by Western blot in RAMS11 CRISPR KO and CBX4 silenced cells (FIG. 7m). We also observed a decrease in cellular invasion when CBX4 or TOP2α were transiently silenced in LoVo cell lines (FIG. 18a, FIG. 18b). Collectively, these data demonstrate RAMS11-dependent CBX4 binding to the TOP2α promoter. Taken together, we provide evidence of RAMS11-dependent CBX4 regulation of TOP2α to induce the metastatic phenotype in CRC (FIG. 8).

RAMS11 Promotes Chemotherapy Resistance In Vivo

To determine if cells with high RAMS11 expression promote resistance to fluorouracil (5FU) treatment, 9-week-old female NOD scid mice were injected with 1 e6 wildtype (WT) or RAMS11-overexpressing (RAMS11) HT29 cells (with GFP-luciferase incorporated) via the tail vein, a common model of lung metastasis[13]. Seventy-two hours after tumor cell injection mice were subcutaneously treated with vehicle (PBS) or 50 mg/kg 5FU and imaged weekly. Analysis of viable tumor cells by BLI imaging showed a significant increase in lung metastasis in RAMS11 cell-injected mice compared to WT cell-injected mice starting at Week 1 (FIG. 8). Further, WT cell-injected mice treated with 5FU showed a 37% to 67% reduction of tumor burden over the 3-week time course (FIG. 8a, FIG. 8b). Ex vivo BLI analysis of lung tissue also showed a 55% decrease at Week 3 (p<0.05, FIG. 8c, FIG. 8d). However, there was no significant change in vehicle and 5FU-treated RAMS11 cell-injected mice in both in vivo and ex vivo lung BLI analysis. These data show mice injected with RAMS11 overexpressing HT29 cells cause an increase in tumor lung burden. Further, high expression of RAMS11 promoted resistance to treatment with 5FU.

Therapeutic Potential of Targeting RAMS11 Directly with Antisense Oligonucleotides (ASOs)

Figure 9:
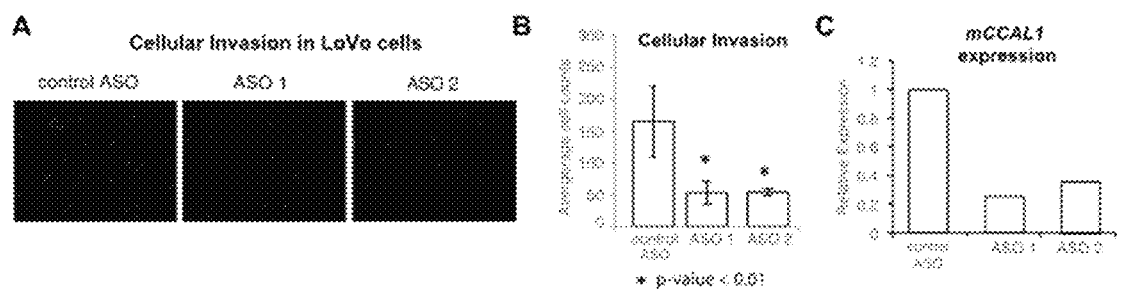
FIG. 9. Inhibiting RAMS11 with ASOs decreases cellular invasion in LoVo cells. (a) Images and (b) quantitation of DAPI stained invaded cells. (c) qPCR of RAMS11 knockdown.
Figure 10:
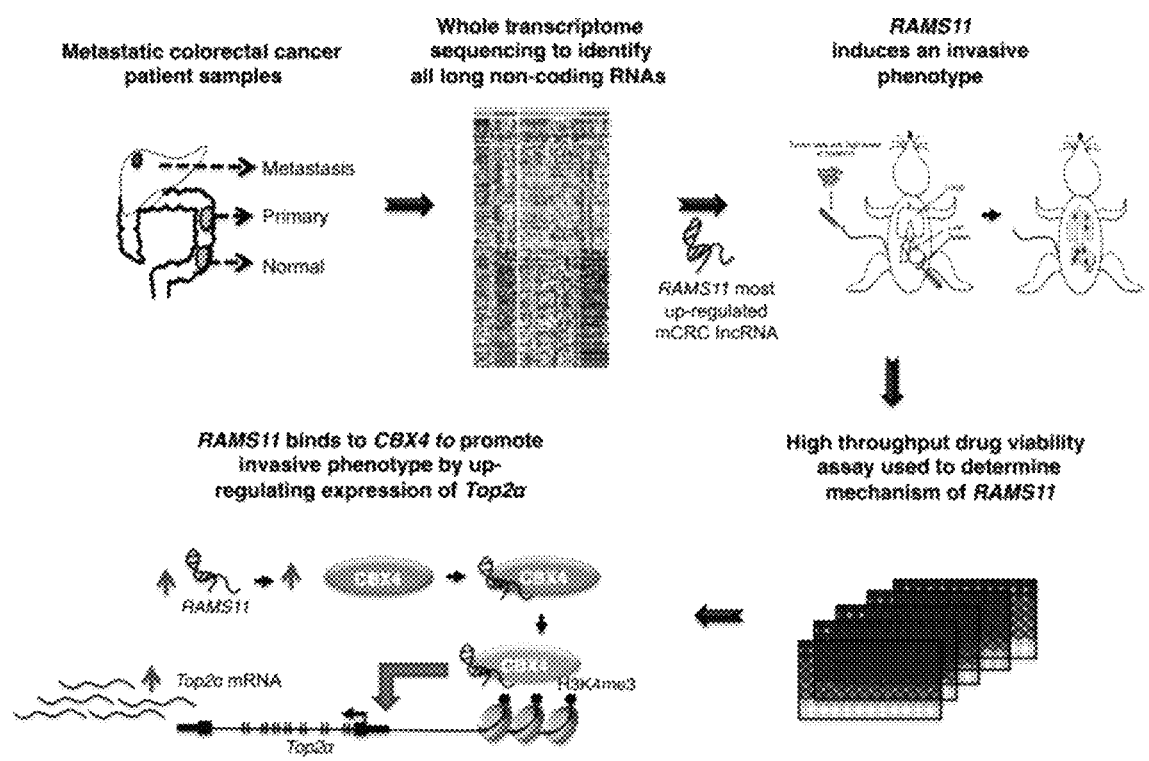
FIG. 10. RAMS11 identification and model in metastatic colorectal cancer. Process of identifying RAMS11 and model showing RAMS11 CBX4 complex binding to Top2α promoter to increase metastatic phenotype.

Exiqon's locked nucleic acid (LNA) GapmeRs antisense oligonucleotides (ASOs) were used. They contain a central stretch (gap) of monomers flanked by blocks of LNA modified nucleotides that (i) increase the target affinity and nuclease resistance of the oligo and (ii) the gap activates RNase H cleavage of the target RNA upon binding. The LNA™ oligonucleotides can be designed for any region of the target RNA sequence. In addition, the design flexibility afforded by LNA™ means that it is possible to design multiple LNA™ antisense oligonucleotides to the same target sequence, which serve as useful experimental controls. As recommended by Exiqon, we have already evaluated multiple in vivo optimized ASOs and selected two that resulted in the most potent RAMS11 knockdown and recapitulate our in vitro results using our RAMS11 CRISPR KO models (FIG. 9), but do not alter cell viability. The two most potent ASOs tested were: ASO #1: CAACTTCCAGCAAGAT (SEQ ID NO: 41) and ASO #2: AGAACTGCTAAAAGTG (SEQ ID NO: 42).

RAMS11 Detection in Human CRC Patient Tissues with the Formalin-Fixed, Paraffin-Embedded (FFPE) Samples To determine if we can detect the lncRNA, RAMS11, in human CRC patient tissues we performed a study with the formalin-fixed, paraffin-embedded (FFPE) samples. We used the RNAscope 2.5 HD (see e.g., Wang et al. RNAscope: a novel in situ RNA analysis platform for formalin-fixed, paraffin-embedded tissues. *J Mol Diagn.* 2012 January; 14(1):22-9) by ACDBio to perform RNA in situ hybridization (ISH) using a custom hRAMS11 RNA probe (~20 target double-Z proprietary custom design), a negative control probe targeting DapB (a bacterial gene), and a positive housekeeping gene, Hs-PPIB to detect single RNA molecules in cells. Briefly, after tissues were deparaffinized and pretreated the RNA-specific probes were hybridized to the target RNA followed by a series of signal amplification and detection with Fast Red dye for chromogenic staining. The tissues were then visualized using the ZEISS Axiolmager brightfield microscope.

Discussion

In the current study, we performed transcriptome sequencing of matched normal, primary, and distant metastatic patient samples to identify lncRNAs associated with metastatic progression that could serve as a resource for further functional characterization and biomarker studies. To exemplify this, we prioritized RAMS11 since it was overexpressed in primary and mCRC tumors and its expression correlated with poor disease-free survival. This demonstrates the potential utility of RAMS11 expression as a marker to stratify high-risk patients. Supporting our clinical findings, we were able to confirm that RAMS11 promoted oncogenic phenotypes in vitro and in vivo in several cancer types.

To assess the clinical potential of RAMS11 and elucidate its regulatory mechanism for promoting aggressive phenotypes we used a high-throughput drug assay. We found that antimetabolites gemcitabine and floxuridine had the most significant increase in cellular viability when RAMS11 was overexpressed. We also found that RAMS11 promoted resistance to more than half of the topoisomerase inhibitors screened. Currently, the elevated expression of TOP2α in primary and mCRC patients[49-51] has served as the rationale for using anthracylines to treat select patients with mCRC. This can be exemplified by an ongoing phase II study to investigate the efficacy of epirubicin as a second-line treatment for patients with TOP2α gene amplification and oxaliplatin-refractory mCRC[52] (EudraCT 2013-001648-79). Our study provides mechanistic insight into RAMS11-dependent TOP2α regulation in mCRC to promote resistance to these inhibitors. In addition, despite the promise of using anthracylines as a mCRC treatment, there are still many limitations including dose-limiting toxicities, intestinal toxicities, cumulative cardiotoxicity, and off-target effects on TOP2β leading to TOP2β poisoning[53]. Fortuitously, RAMS11 specifically targets TOP2α, and could be investigated for its therapeutic potential given the increased use of RNA therapeutics, such as locked nucleic acids, in clinical trials.

Currently, several topoisomerase inhibitors are currently FDA approved for treating multiple cancer types and are first-line therapies for breast cancer, bone, and soft tissue sarcoma, bladder cancer, anaplastic thyroid cancer, Hodgkin's and non-Hodgkin's lymphoma, and multiple myeloma[53-55]. In addition, TOP2α is used as a proliferation marker in multiple cancer types, including CRC[56,57], and elevated levels of TOP2α expression are associated with metastasis in prostate cancer, pancreatic cancer, and breast cancers[58-61]. Therefore, the clinical impact of our study extends beyond mCRC and affects a broader patient population given the widespread use of FDA-approved topoisomerase inhibitors coupled with the altered expression of RAMS11 across multiple solid tumors.

Overall, our understanding of how lncRNAs promote metastasis in CRC patients may have tremendous biological and clinical significance. To address this, our study used patient samples to characterize the landscape of lncRNA expression throughout the progression of primary to mCRC. We also show that lncRNA RAMS11 directly affects mCRC biology, including promoting an aggressive phenotype and correlating with treatment response and resistance.

Methods

Patient Samples and RNA Sequencing

Patients were enrolled at Washington University School of Medicine in St. Louis and informed consent was obtained under an IRB-approved protocol. Adjacent normal, primary, and liver metastasis tissues were resected from mCRC patients and fresh frozen prior to RNA extraction (TABLE 4). PolyA cDNA libraries were constructed using NuGen Ovation Kit V2, and paired-end sequencing was performed on Illumina HiSeq 2000. RNA-Seq data from Kim cohort was downloaded from NCBI GEO (GSE50760). TCGA RNA-Seq pre-aligned bam files were downloaded from the Cancer Genomics Hub (http://cghub.ucsc.edu/).

TABLE 4

Metastatic colon cancer patient information and RNA sequencing data mapped rates.

| Patient | Sample | Site | Type | Total pair-ended reads | Mapped rate |
| --- | --- | --- | --- | --- | --- |
| H_NT-116 | H_NT-116-00116-07_A2_D1_A4 | distant metastasis (liver 1 (1/3) (seg 5)) | M | 185,048,292 | 80.3% |
| H_NT-121 | H_NT-121-00121-07_A1_D1_A4 | distant metastasis (liver 2 (1/1)) | M | 177,567,846 | 76.9% |
| H_NT-206 | H_NT-206-00206-07_A3_D1_A5 | distant metastasis (liver 1 (1/3)) | M | 186,946,054 | 77.4% |
| H_NT-206 | H_NT-206-00206-07_A9_D1_A4 | distant metastasis (liver 1 (3/3)) | M | 184,158,864 | 78.9% |
| H_NT-206 | H_NT-206-00206-07_A6_D1_A5 | distant metastasis (liver 1 (2/3)) | M | 189,793,030 | 76.5% |
| H_NT-261 | H_NT-261-261-07_A3_D1_A4 | distant metastasis (abdominal wall (1/1)) | M | 197,736,134 | 76.9% |
| H_NT-268 | H_NT-268-00268-06_A3_D1_A3 | primary tumor (right/transverse colon) | P | 188,554,492 | 76.9% |
| H_NT-268 | H_NT-268-00268-07_A3_D1_A4 | distant metastasis (liver 1 (1/3, right liver mass #1)) | M | 179,624,613 | 78.8% |
| H_NT-292 | H_NT-292-00292-11_A3_D1_A4 | uninvolved rectum mucosa | N | 177,455,275 | 72.6% |
| H_NT-293 | H_NT-293-00293-07_A3_D1_A4 | distant metastasis (liver 2 (1/1)) | M | 196,559,003 | 80.4% |
| H_NT-294 | H_NT-294-00294-09_A3_D1_A4 | uninvolved rectum mucosa | N | 185,787,393 | 75.2% |
| H_NT-302 | H_NT-302-00302-09_A3_D1_A4 | uninvolved colon mucosa | N | 190,004,532 | 76.4% |
| H_NT-318 | H_NT-318-1304081R_A5 | uninvolved rectum mucosa | N | 193,996,109 | 80.9% |
| H_NT-322 | H_NT-322-1304084R_A5 | distant metastasis (liver 1 (2/3, seg 2) | M | 184,377,811 | 83.3% |
| H_NT-322 | H_NT-322-1304083R_A5 | distant metastasis (liver 1 (1/3, seg 3) | M | 191,075,064 | 82.2% |
| H_NT-322 | H_NT-322-1304086R_A5 | uninvolved colon mucosa | N | 183,375,544 | 99.0% |
| H_NT-322 | H_NT-322-1304082R_A5 | primary tumor (sigmoid colon) | P | 191,797,752 | 84.5% |
| H_NT-322 | H_NT-322-1304085R_A5 | distant metastasis (liver 1 (3/3, seg 6)) | M | 183,637,129 | 84.5% |

TABLE 4-continued

Metastatic colon cancer patient information and RNA sequencing data mapped rates.

| Patient | Sample | Site | Type | Total pair-ended reads | Mapped rate |
|---------|--------|------|------|------------------------|-------------|
| H_NT-324 | H_NT-324-1304088R_A5 | uninvolved colon mucosa | N | 190,864,882 | 78.2% |
| H_NT-329 | H_NT-329-1304089R_A5 | uninvolved colon mucosa | N | 181,614,660 | 82.2% |
| H_NT-344 | H_NT-344-1305212_R_A4 | uninvolved rectum mucosa | N | 165,407,614 | 76.4% |
| H_NT-349 | H_NT-349-1305219_R_A4 | uninvolved colon mucosa | N | 188,112,645 | 80.0% |
| H_NT-350 | H_NT-350-1306101_R_A4 | uninvolved colon mucosa | N | 189,297,299 | 80.2% |
| H_NT-45 | H_NT-45-00045-07_A2_D1_A4 | distant metastasis (liver 2 (1/4)) | M | 198,190,443 | 80.0% |
| H_NT-63 | H_NT-63-00063-07_A1_D2_A4 | distant metastasis (liver 1 (1/1)) | M | 184,879,946 | 74.0% |
| H_NT-95 | H_NT-95-00095-07_A1_D2_A3 | distant metastasis (liver 1 (1/1)) | M | 189,488,535 | 74.7% |

RNA-Seq Data Analysis

The human reference genome assembly version GRCh38/hg38 and the corresponding gene annotations were used in RNA-Seq analysis. Gene annotations were combined from Gencode v23[62], RefSeq downloaded from the UCSC Genome Browser[63], and the Broad lncRNA catalog[64]. Redundant transcripts were removed and overlapping transcripts were assigned to the same gene. RNA-Seq reads were aligned to the human genome using Tophat 2.0.8[65]. Transcript assemblies were generated using Cufflinks 2.1.1[66]. Feature Counts v1.5.0[67] was used to generate fragment counts for individual transcripts requiring a mapping quality score ≥1. FPKM was calculated using transcript fragment counts. For DE analysis, the transcript with highest FPKM among isoforms were selected to represent a gene locus, similar to our previous approach[68]. EdgeR 3.8.6[69] was used to perform a TMM normalization and DE analysis using the raw fragment counts. In the meta-analysis, DE p values were combined using the Stouffer method[70] and fold change was averaged between WUSTL and Kim cohorts. RAMS were defined as lncRNAs that were not tissue specific and DE between metastasis versus primary tumor and between metastasis versus normal tissue (FC≥2, FDR≤0.05).

Exon Array Data Analysis

We repurposed the Affymetrix exon array for lncRNA analysis by realigning the probe set sequences against the human transcript sequences using SeqMap 1.0.12[71] allowing one mismatch. Only probe sets consisting of probes that were uniquely aligned to transcripts from the same gene were retained. Exon array expression was processed and normalized using Affymetrix Power Tool 1.18 (Thermo Fisher).

Survival Analysis

Survival analysis was performed using the Cox proportional hazard model with R survival package 2.37-7 2014. The median expression of RAMS11 within a cohort was used to stratifying patients into low and high RAMS11 expression groups. Kaplan-Meier curves were plotted using the R survplot package 0.0.7 2014.

Cell Culture

Colon cancer cell lines CCD18-Co and SW480 were a kind gift from Dr. David Shalloway at Cornell University. All other colon cell lines (HT29, HT-15, DLD1, SW620, Caco-2, HCT-116, and RKO) were a kind gift from Dr. A. Craig Lockhart at Washington University. LoVo cell lines were purchased from ATCC (ATCC CCL-229). HCC95 and A549 cell lines were a kind gift from Dr. Lauren Michel and Dr. Brian Van Tine, respectively, from Washington University. SW620 cells were grown in DMEM (Invitrogen, Carlsbad, CA) with 10% fetal bovine serum (Sigma, St. Louis, MO), and 1% penicillin/streptomycin (Invitrogen, Carlsbad, CA) complete media. LoVo cells were grown in DMEM/F12 (Invitrogen) with 10% fetal bovine serum, and 1% penicillin/streptomycin complete media. HT29, HT-15, DLD1, and Caco-2 cells were grown in McCoys (Invitrogen) with 10% fetal bovine serum and 1% penicillin/streptomycin, and all other cells were grown in RPMI (Invitrogen) with 10% fetal bovine serum, and 1% penicillin/streptomycin complete media.

Rapid Amplification of cDNA Ends (RACE)

5' and 3' RACE was done using the GeneRacer Kit (Invitrogen) according to the manufacturer's instructions. RACE PCR products were obtained with Platinum Taq High Fidelity (Invitrogen) using the GeneRacer primer (supplied) and a gene-specific primer found in TABLE 5. Products were visualized on a 2% agarose gel and purified by gel extraction (Qiagen, Germantown, MD). This product was then cloned into pcr4-TOPO vector (Invitrogen) and grown in TOP10 E. coli. Clones were sequenced with the M13 forward primer at the Protein and Nuclei Acid Chemistry Laboratory at Washington University.

TABLE 5

Primer list for qPCR, CHIP, siRNAs, and RACE.

| Assay | Gene name | Application | SEQ ID NO: | Forward/Sense | SEQ ID NO: | Reverse/Antisense |
|---|---|---|---|---|---|---|
| qPCR | RPL32 | qPCR | 7 | AGGCATTGACAACAGGGTTC | 8 | GTTGCACATCAGCAGCACTT |
| qPCR | RAMS11 | qPCR | 9 | AAGAGGGCTAGAAGACGGGA | 10 | GGACACAGCTTTTGACGGTTC |
| qPCR | GAPDH | qPCR | 11 | ACTTTGTCAAGCTCATTTCC | 12 | CACAGGGTACTTTATTGATG |
| qPCR | MTRNR1 | qPCR | 13 | TAGCCCTAAACCTCAACAGT | 14 | TGCGCTTACTTTGTAGCCTTCAT |
| qPCR | U1 | qPCR | 15 | GGGAGATACCATGATCACGAAGGT | 16 | CCACAAATTATGCAGTCGAGTTTCCC |
| qPCR | MALAT1 | qPCR | 17 | GACGGAGGTTGAGATGAAGC | 18 | ATTCGGGGCTCTGTAGTCCT |
| qPCR | HOTAIR | qPCR | 19 | GACTTGAGCTGCTCCGGAAT | 20 | GGCTAGGGCTGGTTTCACTT |
| qPCR | NEAT1 | qPCR | 21 | GCGAAGTGAAATTGCATTGA | 22 | CGACCAAACACAGAAAAGACAA |
| qPCR | CBX4 | qPCR | 23 | CCTCTCTTCCGATATCCCATCA | 24 | GGGAACCGGAGAACATC |
| qPCR | Top2a | qPCR | 25 | GCCCTCAAGAAGATGGTGTG | 26 | CCAGGGATTTCTCTTCTTTCC |
| qPCR | Top2b | qPCR | 27 | CCTGTGAGCTGGAGGCAC | 28 | CAGGTCAGTGCCCCGTTG |
| CHIP | Top2a promoter | CHIP qPCR | 29 | TGCTTCCGTTTCCTCTCCTA | 30 | TGTCAGCCCACTGTTTACCTT |
| SIRNA | RAMS11 SIRNA1 | silencer RNA | 31 | UUAUGGAGCUUGACUAAAAUU | 32 | UUUUAGUCAAGCUCCAUAAGA |
| SIRNA | RAMS11 SIRNA2 | silencer RNA | 33 | CAGUAACCCUGAAUAAACAUU | 34 | UGUUUAUUCAGGGUUACUGCA |
| SIRNA | CBX4 SIRNA | silencer RNA | 35 | UAUGGGUUCAUCCAGGUCUGA | 36 | AGACCUGGAUGAACCCAUAUU |
| SIRNA | TOP2a SIRNA2 | silencer RNA | 37 | UCGUGGACUAGCAGAAUCCUU | 38 | GGAUUCUGCUAGUCCACGAUU |
| RACE | 5' RACE | 5'3' RACE | 39 | GTTCCCGGATCACGGAGTAGGCA | | |
| RACE | 5' nested RACE | 5'3' RACE | 40 | GGACACAGCTTTTGACGGTTC | | |

Generation of RAMS11 Silenced and Overexpression Cells

LoVo RAMS11 CRISPR KO cell lines were generated through the Genome Engineering and iPSC center at Washington University. CRISPR/Cas9 was used to create a genomic deletion of the last four exons of RAMS 11 in LoVo metastatic colon cancer cells (FIG. 12a). We used two different cell clones for the described experiments. In addition, we silenced expression of RAMS11 using custom silencer select RNAs (siRNAs) targeting RAMS11, CBX4, TOP2α, or a negative scrambled control (Invitrogen). siRNA sequences are listed in TABLES 5.

Full-length RAMS11 transcript was PCR amplified from LoVo cells and cloned into the pCFG5-IEGZ vector (a kind gift from Dr. Ron Bose, Washington University). Full-length RAMS11 inserts were confirmed with Sanger sequencing at the Protein and Nuclei Acid Chemistry Laboratory at Washington University. Retroviral infection of cancer cells was performed according to Kauri et al.[72]. Briefly, the amyotrophic phoenix cell line was transfected with 10 μg of pCFG5-RAMS11 or empty vector control by calcium phosphate precipitation and incubated for 24 h. Viral supernatants were harvested after an additional 24-h incubation. Virus was added to cells seeded in six-well dishes in the presence of 8 μg/mL polybrene (Sigma). Cells were centrifuged at 300×g for 90 min and fresh media was added to the plate. After 14 days of Zeocin (Invitrogen) selection cells were used for assays. HT29 colon cells that had low endogenous expression of RAMS11 were infected with virus expressing RAMS11 or empty vector for 48 h and selected with 100 μg/mL Zeocin.

Quantitative Real-Time PCR

Total RNA was isolated for each CRC cell line using Takara Bio NucleoSpin RNA (Takara, Mountain View, CA). Total RNA was then transcribed to cDNA with SuperScript III First strand cDNA system (Invitrogen) and quantified using Fast Sybr Green Master Mix (Invitrogen) as per the manufacturer's protocol. Primer sequences are available in TABLE 5.

Protein Detection by Western Blot

Figure 19:
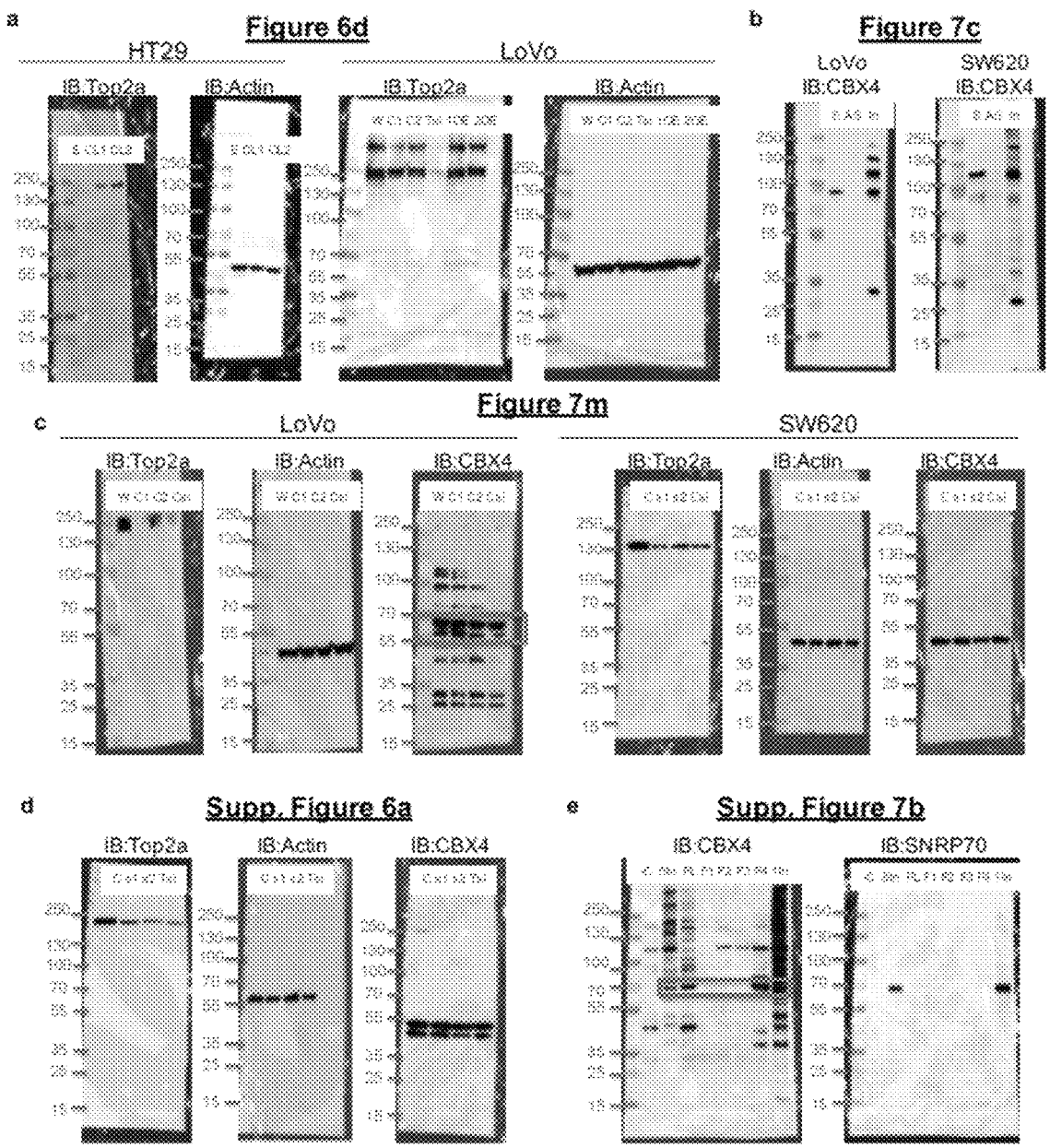
FIG. 19. Raw blots for western blots. (a) FIG. 6d western blots, (b) FIG. 7c RNA Pull down blots, (c) FIG. 17m blots, (d) FIG. 16a blots, and (e) FIG. 17b. Cell lines and antibodies are labeled on top of gels. Protein ladders are labeled in blue and proteins. Samples derived from the same experiment and blots were processed in parallel. E (EV), CL1 (clone1), CL2 (clone2), W (Wild Type), C1 (CRISPR1), C2 (CRISPR2), Tsi (Top2α siRNA), 1OE (CRISPR1 RAMS11 OE), 2OE (CRISPR2 RAMS11 OE), S (Sense), AS (Antisense), In (Input), Csi (CBX4 siRNA), s1 (RAMS11 sirna1), s2 (RAMS11 sirna2), −C(negative control), 0.5|n (5% input), FL (full length), F1 (Fragment1 1-250), F2 (Fragment2 250-450), F3 (Fragment3 400-650), F4 (Fragment1 600-959), 1 In (1% input).
Figure 20:
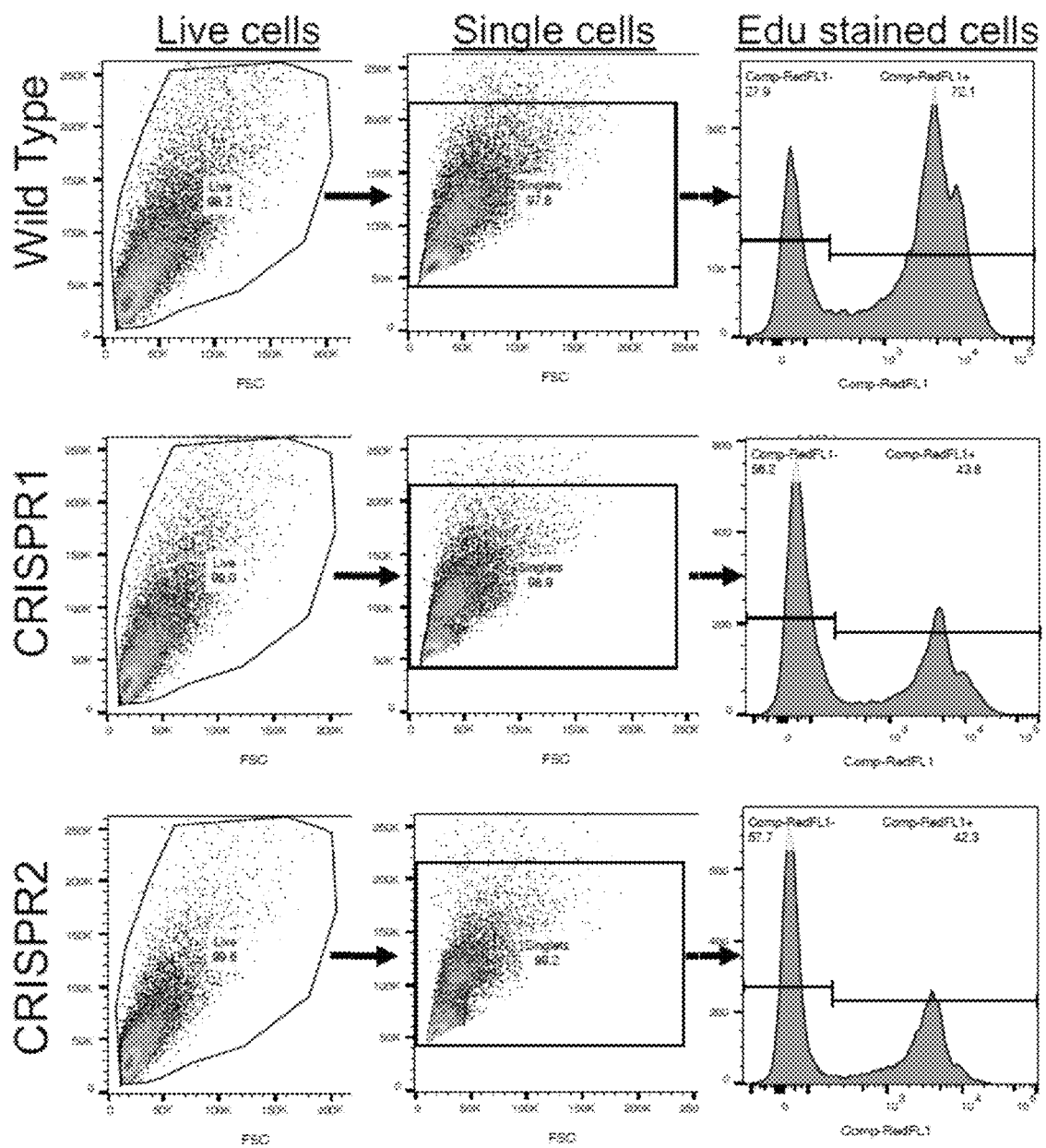
FIG. 20. Gating strategy for FIG. 12f. LoVo Wild Type, CRISPR1, and CRISPR2 gating for live cells then single cells and Edu stained cells (RedFL+) showing decease Edu in CRISPR cell lines.

Western blots were conducted by plating 250,000 representative cancer cells in a six-well dish. For transient knockdown experiments, the next day cells were transfected at 6.25-25 nM with two independent custom designed siRNAs or a negative scramble control with Lipofectamine RNAiMax (Invitrogen) for 72 h. Cells were then lysed with Tris lysis buffer (50 mM Tris-HCl, 1% Triton X-100, 131 mM NaCl, 1 mM sodium orthovanadate, 10 mM $Na_4P_2O_7$, 10 mM NaF, 1 mM EDTA), run on NuPAGE 4-12% Bis-Tris gel (Invitrogen) and transferred to nitrocellulose membrane (BioRad, Hercules, CA). Blots were then probed overnight at 4° with respective antibodies including TOP2A, CBX4, and ACTIN, then washed with TBST buffer, and then applied with secondary goat anti-rabbit HRP-linked or goat anti-mouse HRP-linked antibodies (Thermo Fisher, Waltham, MA). Blots were then washed, visualized with Clarity Western ECL Substrate (Bio-Rad), and imaged using the ChemiDoc XRS+ System (Bio-Rad). Band intensities were quantified from the digital image in ImageJ and are shown normalized to the control lane for each target. Raw Western blots are shown in FIG. 19. All antibodies and concentrations are listed in TABLE 6.

TABLE 6

List of antibodies used.

| Name | Company | Catalog number | Dilution/Concentration |
|---|---|---|---|
| Top2A | Cell Signaling | 12286S | 1:1000 |
| CBX4 | Abcam | ab139815 | 1:1000 |
| Actin | Cell Signaling | 3700S | 1:1000 |
| Anti-rabbit HRP linked | Cell Signaling | 65-6120 | 1:5000 |
| Goat anti-mouse HRP-linked | Thermo | 31430 | 1:5000 |
| IgG | Cell Signaling | 2729S | 5 ugs |
| H3K4me3 | Abcam | ab12209 | 5 ugs |
| Ki67 | Cell Signaling | 9027S | 1:150 |
| SNRP70 | EMD Millipore | 03-103 | 1:1000 |

RNA Immunoprecipitation

RIP coupled to qPCR assays were conducted by isolating nuclear lysates from ten million LoVo or SW620 cells following the NER-PER Nuclear and Cytoplasmic Extraction Reagent Kit (Thermo Fisher). Nuclear lysates were then incubated overnight with 5 μg CBX4 antibody or IgG antibody isotype control in RIPA wash buffer (50 mM Tris-HCl pH 7.4, 150 mM NaCl, 1 mM $MgCl_2$, 1% NP40, 0.5% Na-deoxycholate, 0.05% SDS, 1 mM EDTA) and SUPERase-in RNAse inhibitor (Invitrogen). The next day 50 μL of Invitrogen Dynabeads Protein G were added to the antibody lysate/mixture and were rotated for 1 h at 4°. Next, beads were subsequently washed six times with RIPA wash buffer using a magnetic bead separator. Protein was then digested with proteinase K buffer (RIPA buffer, 10% SDS, 10 mg/mL proteinase K), at 55° for 30 min shaking. RNA was phenol:chloroform:isoamyl alcohol extracted following the general protocol (Thermo Fisher). Last, gDNA was removed from RNA using ArcticZymes Heat and Run gDNA removal kit following the manufacturer's protocol (Tromso, Norway). cDNA was made using SuperScript III First strand cDNA system as indicated above and qPCR was run with Fast Sybr Green Master Mix and indicated primers (TABLE 5). Fold enrichment of qPCR results were calculated following Sigma-Aldrich Data Analysis Calculation Shell by comparing nonspecific control IgG antibody raw CTs to CBX4 RNA binding protein CT normalized against 1% input.

Chromatin Immunoprecipitation

ChIP qPCR assays were conducted by first sonicating five million cells in SDS lysis buffer (1% SDS, 500 mM EDTA, 50 mM Tris-HCl pH 8). Next, sonicated cells were immunoprecipitated with 5 μg IgG, CBX4, or H3K4me3 antibodies in ChIP dilution buffer (0.01% SDS, 1.10% Triton X-100, 1.2 nM EDTA, 16.7 mM Tris-HCl pH 8, 167 mM NaCl), and 1× Halt Protease and Phosphatase inhibitors overnight with rotation at 4°. The next day Dynabeads Protein G (Invitrogen) were added to the antibody lysate mixture and rotated for 1 h. Bead/lysate mixture was then washed once with low salt wash buffer (0.1% SDS, 1% Triton X-100, 2 mM EDTA, 20 mM Tris-HCl pH 8, 150 mM NaCl), then high salt buffer (0.1% SDS, 1% Triton X-100, 2 mM EDTA, 20 mM Tris-HCl pH 8, 500 mM NaCl), lithium chloride wash buffer (0.25 M lithium chloride, 1% NP40, 1% sodium deoxycholate, 1 mM EDTA, 10 mM Tris-HCl pH 8), and finally two washes with Tris-HCl EDTA buffer (10 mM Tris-HCl pH 8, 1 mM EDTA). DNA was eluted by incubating beads for 30 min at room temperature with SDS elution buffer (1% SDS, 0.1 M sodium bicarbonate), followed by 1.25 M NaCl and 2.5 mg/mL RNAse A at 95° for 15 min shaking followed by addition of proteinase K buffer (1 μL 10 mg/mL proteinase K, 5 μL 0.5 μM EDTA, 10 μL 1 M Tris pH 7.5) shaking at 60° for 15 min. DNA was then isolated using phenol:chloroform:isoamyl alcohol extraction following the general protocol as mentioned above. DNA was diluted by five and used for qPCR. The % input calculations were determined by comparing CT values from input DNA and ChIP DNA for the TOP2A target promoter region using the following equation: % Input=% of starting input fraction×$2^{[CT(input)-CT(Chlp)]}$ Primer sequences are available in TABLE 5.

BrU-Labeled RNA Pull Down

Full-length RNA probes and fragmented RAMS11 probes were made using the Promega Riboprobe in vitro transcription kit from 2.5 μg of linearized DNA in the pGEM-3Z vector (Madison, WI). Antisense probes were made by in vitro transcription from the SP6 promoter. RAMS11 RNA pull-down experiments were performed in LoVo and SW620 nuclear lysates following the RiboTrap Kit manufacturer's protocol (MBL, Woburn, MA). Truncated RAMS11 probes consisted of fragments 1-250, 200-450, 400-650, and 600-959 basepairs of RAMS11. RAMS11 probes were synthesized and subcloned at Gene Universal (Newark, DE).

Nuclear Cytoplasmic Isolations

Nuclear and cytoplasmic isolations were conducted using the PARIS Kit (Thermo Fisher) following the manufacturer's protocol. Total RNA was also collected as described above. Nuclear and cytoplasmic isolations were calculated by normalizing respective gene to total RNA expression.

Transwell Assays

Cell lines were seeded at 300,000 cells in a six-well dish. The next day cells were transfected with siRNAs targeting RAMS11, TOP2α, CBX4, or overexpression plasmids. Seventy-two hours later cells were harvested and reseeded at 200,000 cells on a transwell 8.0 μM permeable membrane support (Corning, Corning, NY) in 24-well plates for a modified Boyden chamber assay. A serum gradient was established with cells plated in serum-free media and complete media (10% FBS) added to the bottom of the well. For invasion assays, transwells were precoated with 200 μg/mL Matrigel (Corning) before addition of cells. Cells were allowed to migrate or invade overnight and then fixed with 4% paraformaldehyde (Electron Microscopy Sciences, Hatfield, PA), and nuclei were stained with DAPI (Sigma, 1

µg/µL). A cotton swab was used to remove cells from the top of the membrane. Migrated DAPI-stained cells were imaged with Q-Capture Pro software on an Olympus IX70 microscope, quantified using ImageJ software, and statistical significance was determined by a Student's two-tailed t-test. Four to seven images were taken per transwell membrane at ×20 magnification. Assays were repeated two to three times.

Soft Agar Assays

HT29 cells overexpressing RAMS11 and LoVo RAMS11 CRISPR KO cell lines were resuspended at 75,000 cells in 0.4% Difco soft agar (BD Bioscience, Franklin Lakes, NJ) and seeded onto a 5% Difco base agar. Cells were given fresh media every 3 days for around 2 weeks, and once colonies were visible by eye, cells were stained with 0.5% Crystal Violet (Sigma) for 3 h. Plates were then imaged using the ChemiDoc XRS+(Bio-Rad) and counted with ImageJ software. Average cell counts were used for comparison and statistical significance was determined by a Student's two-tailed t-test. Assays were repeated three times.

Drug Treatments

The NIH approved oncology library of 119 drugs (AOD6 plate 4825-1 and AOD6 plate 4826) was received from the NIH National Cancer Institute DTP Developmental Therapeutics Program. Drugs were diluted in DMSO to 1 mM and the well assignments were rearranged so drugs were confined to the inner 60 wells of 96-well plates. HT29 RAMS11 overexpressing Clone1 and Clone2 cell lines were seeded at 5000 cells per well in a 96-well plate. The next day serial diluted drug was added to pre-seeded plates in media containing 1% DMSO vehicle, using a Robbins Hydra 96 micro dispenser. Two 96-well plates of cells were used as vehicle controls. The plates were incubated for 3 days. Percent viability was scored by incubating cells for 3 h with resazurin sodium (0.023 mg/mL, Sigma R7017). The reaction was stopped by the addition of SDS (1% final concentration). Fluorescence Ex/Em 540/590 was read in a Biotek Synergy H1 plate reader (Winooski, VT). The fluorescence values for the vehicle plates were averaged and percent viability was determined by the formula: Percent viability= (average vehicle−value)/(average vehicle−average resazurin in media blank)×100. We removed drugs that were undetectable, or out of range, by resazurin assay, leaving 118 drugs to assess in the study (TABLE 3). Values with more than a 1.5-fold change in both RAMS11 Clone1 and Clone2 overexpressing cell lines were used to determine significance. Individual drug $IC_{50}$ assays were done in a similar manner as described above with CRISPR KO cells. Assays were repeated more than three times.

In Vivo Models

The animal studies were reviewed and approved by Washington University's Institutional Animal Care and Use Committee protocol. For subcutaneous injections, 2e6 LoVo wild-type, RAMS11 CRISPR1, or RAMS11 CRISPR2 luciferase-tagged cells were injected subcutaneously in ten NOD/SCID mice per group. Weekly tumor size was determined by caliper measurements comparing length×width×height×0.5. For post analysis lung tissues and subcutaneous tumors tissues were removed and formalin fixed and paraffin embedded. This experiment was repeated two times.

In the lung metastasis mouse model, 2e6 LoVo wild-type and CRISPR luciferase-tagged cell models were injected into the lateral tail vein of twelve 5-week-old NOD/SCID mice (Jackson Laboratories, Bar Harbor, MA) per group using 30-gauge needles. In weekly intervals, mice were imaged with the Olympus OV100 Small Animal Imaging System (IVIS Spectrum, Caliper, Hopkinton, MA) in conjunction with the Small Animal Imaging Core (SAIC) at Washington University. Mice were imaged for 1 min with sequential 5-s exposures. Luminescence was quantified using the Living Image Software 3.2 (Caliper). All micrometastasis were imaged at day 0 (30 min to 1 h) post operation and weekly for 12 weeks. At the conclusion of the study, mice were sacrificed and examined visually and with bioluminescence for lung metastases in vivo and ex vivo. Lungs were dissected and formalin fixed and paraffin embedded for histological analysis with H&E and Ki67 staining. This experiment was repeated twice.

For the hemisplenectomy mouse model[38], 2e6 LoVo wild-type and CRISPR luciferase-tagged cells in 50 µL of PBS were injected into the spleen of 6-8-week-old NGS mice (Jackson Laboratories) (WT n=18, CRISPR1 n=11, CRISPR2 n=11) using 30-gauge needles during open laparotomy. Cell injections were followed with a 50 µL PBS flush. Incisions were closed with sutures and surgical clips. In weekly intervals mice were imaged with the Olympus OV100 Small Animal Imaging System (IVIS Spectrum) in conjunction with SAIC. Mice were imaged for 10 s to 1 min exposures. Luminescence was quantified using the Living Image Software 3.2 (Caliper). All micrometastasis were imaged at day 7, day 14, and day 21 post operation. At the conclusion of the study, mice were sacrificed and examined visually and by bioluminescence for liver metastases in vivo and ex vivo. Livers were dissected, weighed, and formalin fixed and paraffin embedded for histological analysis with H&E and Ki67 staining. This experiment was repeated three times.

Data Availability

The RNA-Seq data generated in this study (WUSTL cohort) have been deposited in the dbGaP database under the accession code phs001722. The Kim et al.'s data[29] referenced during the study are available in a public repository from the NCBI Gene Expression Omnibus under the accession code GSE50760.

What is claimed is:

1. A method of treating a subject having cancer expressing RAMS11, the method comprising:
providing a biological sample from the subject, the biological sample comprising long noncoding RNA associated with metastasis (RAMS);
measuring a level of RAMS11 (SEQ ID NO: 1) in the biological sample;
administering to the subject, when the measured level of RAMS11 is overexpressed compared to a control sample, a treatment comprising at least one antisense oligonucleotide (ASO) selected from CAACTTCCAGCAAGAT (SEQ ID NO: 41) and AGAACTGCTAAAAGTG (SEQ ID NO: 42); and
wherein the cancer expressing RAMS11 is selected from the group consisting of colorectal cancer (CRC), lung cancer, head or neck cancer, and kidney cancer.

2. The method of claim 1, wherein the subject is not treated with a topoisomerase inhibitor.

3. The method of claim 1, wherein the subject is further administered a therapeutically effective amount of: a kinase inhibitor, an alkylating agent, an antineoplastic antibiotic, or an anthracycline antibiotic.

4. The method of claim 1, wherein the ASO reduces expression of one or more RAMS11 exons selected from the group consisting of:

(SEQ ID NO: 2)
AGAATGCCAAAGAGCAGCAGGATGGATCCAGCATCCTCTCCTGATAAAAG

AGGGCTAGAAGACGGGAGGCTCCGGGAAGTCTACTGG;

(SEQ ID NO: 3)
AGTCATGAAGACACTGAAAAGTGATGAATCCACATAACCATGACACTGGA

AATGAAGTTTGAGTGGCAGTCAGAATCTGGGAGGAAGCATTGCTAAGTGA

AAATCTTATGGAGCTTGACTAAAAATCCCTGTCAGGAACCGTCAAAAGCT

GTGTCCCTGACATGAAAAATCTTGCTGGAAGTTGAGAGAGGTTTATGCCT

ACTCCGTGATCCGGAACACAAGACCTTTACCAACCAAAAAAGTGGATAG

CTGTTCTTCTGCTGTGAAGGTTAATAAAG;

(SEQ ID NO: 4)
AACGCCAGAAGTGCCAAGCAATTAACAACCCCAGAAGCAACCCTTAACCA

ATGATTAAATAAAGTGGATGATTACATACCCAAGCTCCTTCAACTCCCAG

GGACATAATTCTGAG;

(SEQ ID NO: 5)
GGATGGAAAACAAACTGAAACTGGCTCAAGTGAATGCTCACTGGAAGGCT

TACTGGAAAACTTACTGGAAGGATGTGAGGACATGTTCGGGAATCTATTT

GCAGAAAACATATTCAG;
and (SEQ ID NO: 6)
CCCTGTCCACCACAGCCAGCTGGCTGAAGAGCTCAAAAGGCAAGAAATCA

GCAAGAGAGAGAGATGAAGCATGAGAAATGAGCAAAAAACACCCAGCACA

TCATAATCTTGGACAGTTTAGCAGTACATGAAAATAGATGGTCCTCGCCC

CAAGGGACTGCAGTAACCCTGAATAAACAGGATGTCTCTCACTTTTAGCA

GTTCTTTCTGTGCTAGTATTGGGGAAATATATTTTTGGCTGCATGCAAAA

TGGTAAAAGACATCTATTAAGAAAATGAAAACAATGCTTCTGTTTTAGAC

GAAGCTTTTGAAGGTTTAAGGATCACCTATTTATTGACAAAATTGTTTCC

GTGGCTTAAAA.

5. The method of claim 1, wherein the biological sample comprises tumor cells, circulating tumor cells (CTCs), or formalin-fixed paraffin-embedded (FFPE) tissue, or frozen tissue.

6. The method of claim 1, wherein the biological sample comprises tumor long noncoding RNAs (lncRNAs).

7. The method of claim 1, wherein the biological sample is tumor tissue.

8. The method of claim 1, wherein the biological sample is a biopsy sample.

9. The method of claim 1, wherein the cancer is selected from the group consisting of: colorectal adenocarcinoma, lung adenocarcinoma, lung squamous cell carcinoma, head and neck squamous cell carcinoma (HNSC), and kidney renal papillary cell carcinoma (KIRP).

10. The method of claim 1, wherein overexpressed RAMS11, indicates a bad outcome.

11. The method of claim 1, wherein overexpressed RAMS11 indicates aggressive CRC.

12. The method of claim 1, wherein overexpressed RAMS11 indicates a poor prognosis.

13. The method of claim 1, wherein RAMS11 is detected by qPCR.

* * * * *